United States Patent
Lee et al.

(10) Patent No.: US 9,780,312 B2
(45) Date of Patent: *Oct. 3, 2017

(54) CARBAZOLE-BASED COMPOUND AND ORGANIC LIGHT EMITTING DEVICE INCLUDING THE SAME

(71) Applicant: SAMSUNG ELECTRONICS CO., LTD., Suwon-si, Gyeonggi-do (KR)

(72) Inventors: Kumhee Lee, Suwon-si (KR); Jiyoun Lee, Incheon (KR); Yoonhyun Kwak, Seoul (KR); Hyun Koo, Seoul (KR); Daeyoung Chung, Seoul (KR)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 173 days.

This patent is subject to a terminal disclaimer.

(21) Appl. No.: 14/676,103

(22) Filed: Apr. 1, 2015

(65) Prior Publication Data

US 2016/0111657 A1    Apr. 21, 2016

(30) Foreign Application Priority Data

Oct. 17, 2014    (KR) ........................ 10-2014-0141207

(51) Int. Cl.
H01L 51/50    (2006.01)
H01L 51/00    (2006.01)
(Continued)

(52) U.S. Cl.
CPC ........ H01L 51/0072 (2013.01); C07D 405/14 (2013.01); C07D 491/048 (2013.01);
(Continued)

(58) Field of Classification Search
None
See application file for complete search history.

(56) References Cited

U.S. PATENT DOCUMENTS 7,651,791 B2    1/2010    Nakano et al.
8,367,224 B2    2/2013    Katakura et al.
(Continued)

FOREIGN PATENT DOCUMENTS

JP    2009267255    11/2009
JP    201249518    3/2012
(Continued)

*Primary Examiner* — Gregory Clark
(74) *Attorney, Agent, or Firm* — Cantor Colburn LLP

(57) ABSTRACT

A carbazole compound represented by Formula 1:

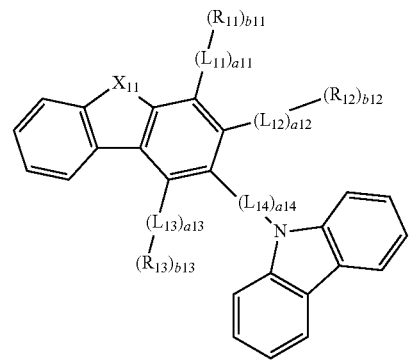

Formula 1 wherein in Formula 1, groups and variables are the same as described in the specification.

18 Claims, 1 Drawing Sheet

(51) Int. Cl.
*C07D 405/14* (2006.01)
*C07D 495/04* (2006.01)
*C07D 491/048* (2006.01)

(52) U.S. Cl.
CPC ........ *C07D 495/04* (2013.01); *H01L 51/0067* (2013.01); *H01L 51/0073* (2013.01); *H01L 51/0059* (2013.01); *H01L 51/0071* (2013.01); *H01L 51/0085* (2013.01); *H01L 51/5016* (2013.01)

(56) References Cited

U.S. PATENT DOCUMENTS

| | | | |
|---|---|---|---|
| 2007/0141387 A1* | 6/2007 | Nakano | C09K 11/06 428/690 |
| 2011/0006670 A1 | 1/2011 | Katakura et al. | |
| 2012/0007063 A1 | 1/2012 | Langer et al. | |
| 2013/0062597 A1 | 3/2013 | Yoshida et al. | |
| 2013/0341602 A1 | 12/2013 | Hikime et al. | |
| 2013/0341612 A1 | 12/2013 | Oohisa et al. | |
| 2015/0336937 A1 | 11/2015 | Lee et al. | |

FOREIGN PATENT DOCUMENTS

| | | |
|---|---|---|
| JP | 2012138585 | 7/2012 |
| JP | 2012169325 | 9/2012 |
| JP | 201316717 | 1/2013 |
| JP | 201369905 | 4/2013 |
| JP | 2013242988 | 12/2013 |
| JP | 2013243236 | 12/2013 |
| KR | 1020120096493 | 8/2012 |
| KR | 1020120096568 | 8/2012 |
| KR | 1020130118858 | 10/2013 |
| KR | 1020130130236 | 12/2013 |
| KR | 101423174 | 7/2014 |
| KR | 101474796 | 12/2014 |
| KR | 10-2015-0134248 A | 12/2015 |
| WO | 2012172482 | 12/2012 |
| WO | 2013168534 | 11/2013 |
| WO | 2014009317 | 1/2014 |

* cited by examiner

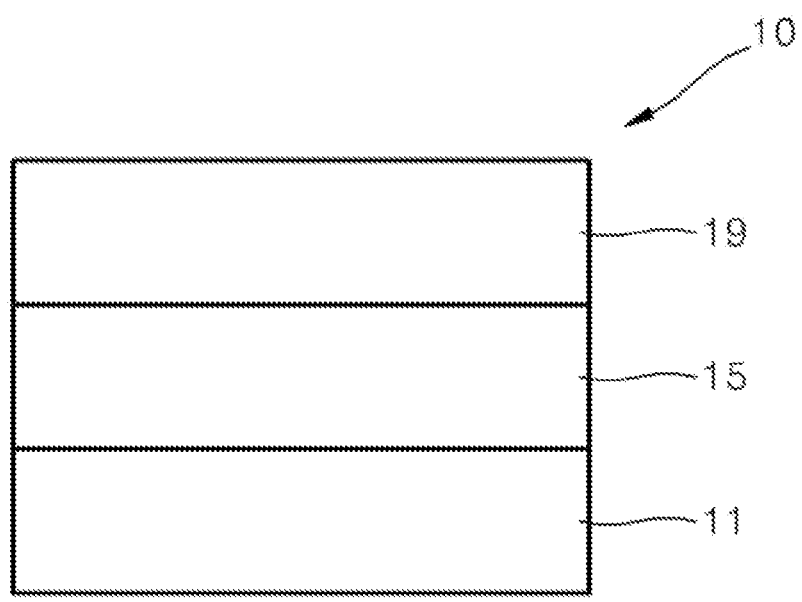

CARBAZOLE-BASED COMPOUND AND ORGANIC LIGHT EMITTING DEVICE INCLUDING THE SAME

CROSS-REFERENCE TO RELATED APPLICATION

This application claims priority to Korean Patent Application No. 10-2014-0141207, filed on Oct. 17, 2014, in the Korean Intellectual Property Office, and all the benefits accruing therefrom under 35 U.S.C. §119, the content of which is incorporated herein in its entirety by reference.

BACKGROUND

1. Field

The present disclosure relates a carbazole compound and an organic light-emitting device including the same.

2. Description of the Related Art

Organic light emitting devices (OLEDs) are self-emission devices that have wide viewing angles, high contrast ratios, and short response times. In addition, the OLEDs exhibit excellent luminance, driving voltage, and response speed characteristics, and produce full-color images.

A typical organic light-emitting device includes an anode, a cathode, and an organic layer that is disposed between the anode and the cathode and includes an emission layer. A hole transport region may be disposed between the anode and the emission layer, and an electron transport region may be disposed between the emission layer and the cathode. Holes provided from the anode may move toward the emission layer through the hole transport region, and electrons provided from the cathode may move toward the emission layer through the electron transport region. The holes and the electrons are recombined in the emission layer to produce excitons. These excitons change from an excited state to a ground state, thereby generating light.

Various types of organic light emitting devices are known. However, there still remains a need in OLEDs having low driving voltage, high efficiency, high brightness, and long lifespan.

SUMMARY

Provided are a carbazole compound and an organic light-emitting device including the same.

Additional aspects will be set forth in part in the description which follows and, in part, will be apparent from the description, or may be learned by practice of the presented exemplary embodiments.

According to an aspect of an exemplary embodiment, a carbazole compound is represented by Formula 1:

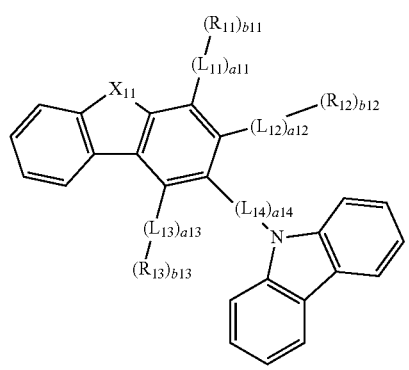

Formula 1

$X_{11}$ is selected from O and S;

$L_{11}$ to $L_{14}$ are each independently selected from a substituted or unsubstituted $C_1$-$C_{60}$ alkylene group, a substituted or unsubstituted $C_2$-$C_{60}$ alkenylene group, a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, and a substituted or unsubstituted $C_1$-$C_{60}$ heteroarylene group;

a11 to a14 are each independently selected from 0, 1, 2, 3, 4, and 5;

$R_{11}$ to $R_{13}$ are each independently selected from $R_{ET}$, a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —N($Q_1$)($Q_2$), —Si($Q_3$)($Q_4$)($Q_5$), and —B($Q_6$)($Q_7$);

at least one selected from $R_{11}$ to $R_{13}$ is $R_{ET}$;

b11 to b13 are each independently selected from 0, 1, 2, 3, and 4;

$R_{ET}$ is selected from Formulae 9-1 to 9-52;

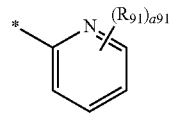

9-1

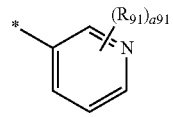

9-2

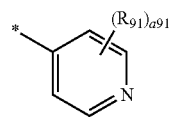

9-3

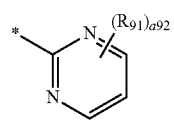

9-4

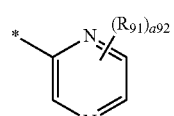

9-5

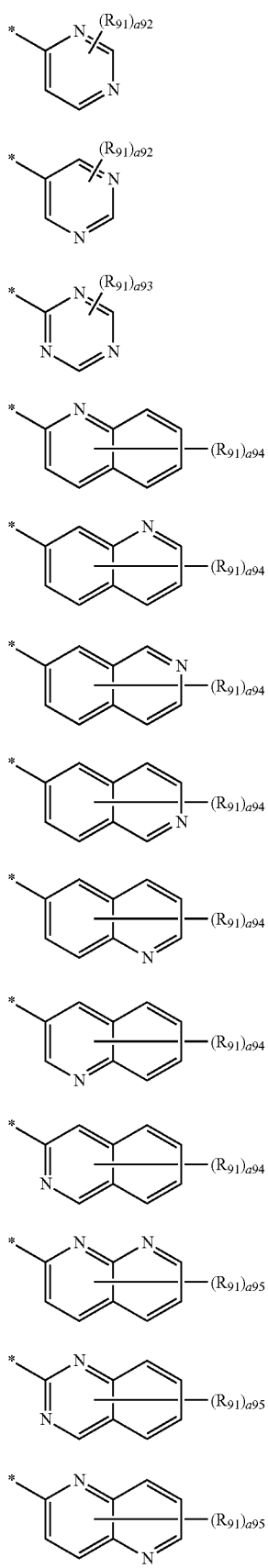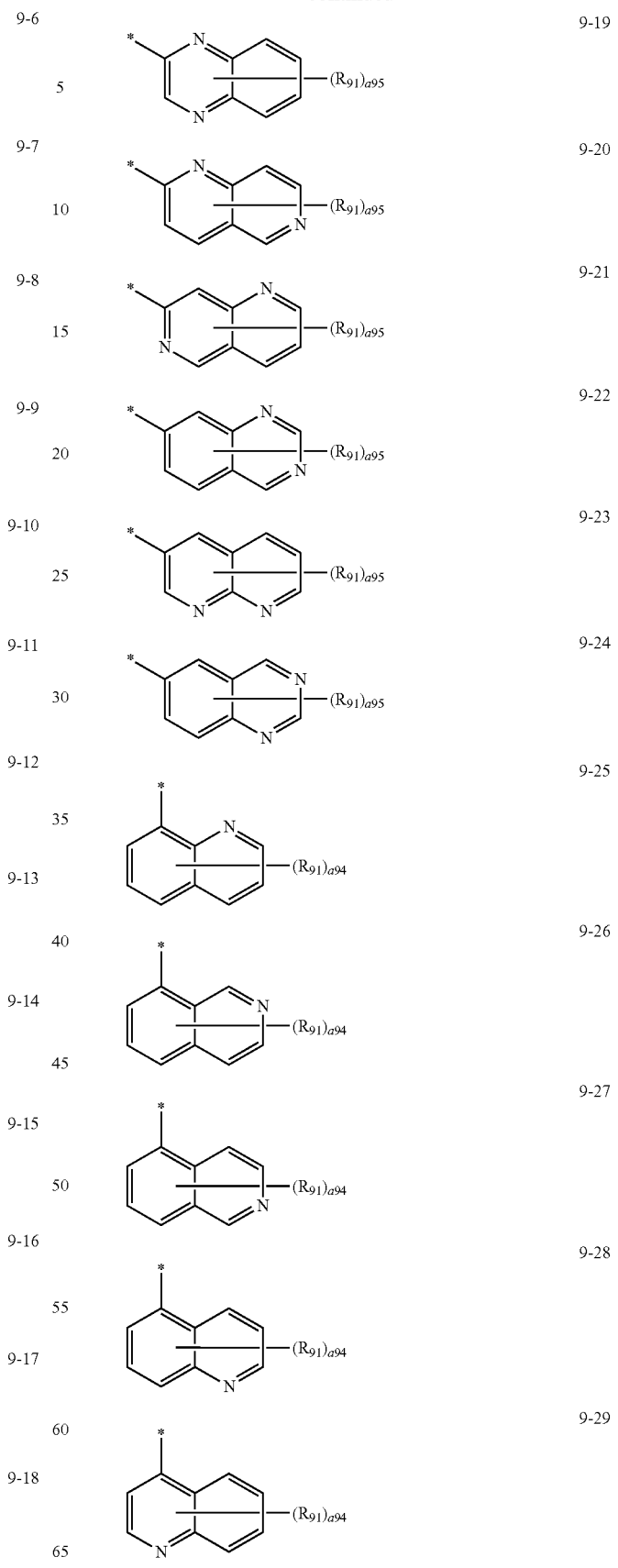

| | |
|---|---|
| 9-30 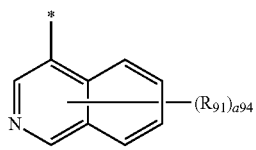 | 9-40 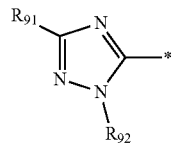 |
| 9-31 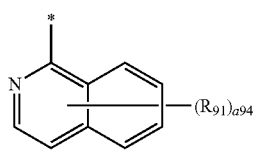 | 9-41 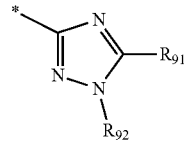 |
| 9-32 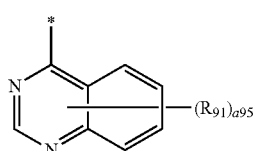 | 9-42 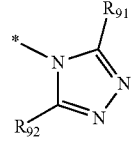 |
| 9-33 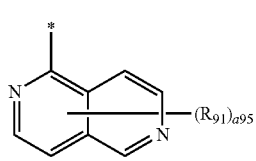 | 9-43  |
| 9-34 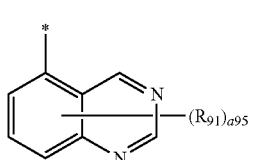 | 9-44 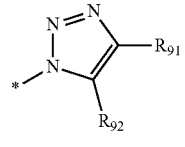 |
| 9-35 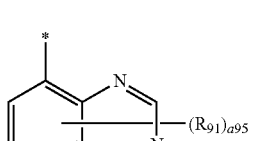 | 9-45 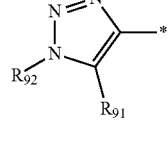 |
| 9-36 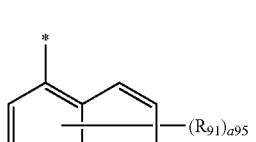 | 9-46 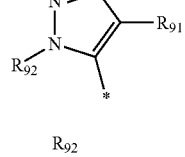 |
| 9-37 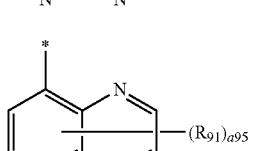 | 9-47 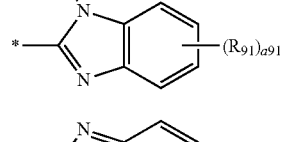 |
| 9-38 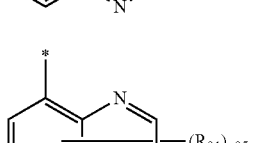 | 9-48 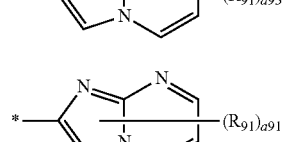 |
| 9-39 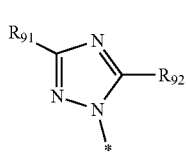 | 9-49 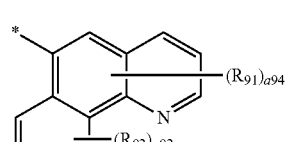 |
| | 9-50 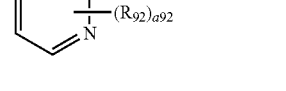 |

-continued

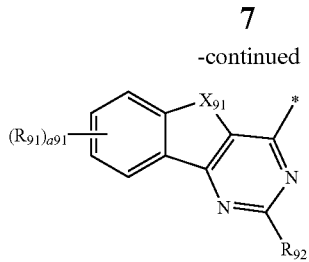

9-51

9-52 wherein in Formulae 9-1 to 9-52, $X_{91}$ is selected from O and S;

$R_{91}$ and $R_{92}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_1$-$C_{60}$ alkoxy group, a $C_6$-$C_{60}$ aryl group, a $C_6$-$C_{60}$ aryloxy group, a $C_6$-$C_{60}$ arylthio group, and a $C_1$-$C_{60}$ heteroaryl group;

a91 is selected from 1, 2, 3, and 4;
a92 is selected from 1, 2, and 3;
a93 is selected from 1 and 2;
a94 is selected from 1, 2, 3, 4, 5, and 6;
a95 is selected from 1, 2, 3, 4, and 5; and
* indicates a binding site to a neighboring atom;

at least one substituent of the substituted $C_1$-$C_{60}$ alkylene group, substituted $C_2$-$C_{60}$ alkenylene group, substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group is selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), and —B($Q_{16}$)($Q_{17}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_1$-$C_{60}$ alkenyl group, a $C_1$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), and —B($Q_{26}$)($Q_{27}$); and —N($Q_{31}$)($Q_{32}$), —Si($Q_{33}$)($Q_{34}$)($Q_{35}$), and —B($Q_{36}$)($Q_{37}$);

wherein $Q_1$ to $Q_7$, $Q_{11}$ to $Q_{17}$, $Q_{21}$ to $Q_{27}$, and $Q_{31}$ to $Q_{37}$ are each independently selected from a hydrogen, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

According to another exemplary embodiment, an organic light-emitting device includes:
a first electrode;
a second electrode; and
an organic layer disposed between the first electrode and the second electrode, wherein the organic layer includes an emission layer and at least one carbazole compound represented by Formula 1.

BRIEF DESCRIPTION OF THE DRAWINGS

These and/or other aspects will become apparent and more readily appreciated from the following description of the exemplary embodiments, taken in conjunction with the accompanying drawings in which:

FIG. 1 is a schematic cross-sectional view of an organic light-emitting device according to an embodiment.

DETAILED DESCRIPTION

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects. As used herein, the term "and/or" includes any and all combinations of one or more of the associated listed items. Expressions such as "at least one of," when preceding a list of elements, modify the entire list of elements and do not modify the individual elements of the list.

It will be understood that when an element is referred to as being "on" another element, it can be directly in contact with the other element or intervening elements may be present therebetween. In contrast, when an element is referred to as being "directly on" another element, there are no intervening elements present.

It will be understood that, although the terms first, second, third etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present embodiments.

The terminology used herein is for the purpose of describing particular embodiments only and is not intended to be limiting. As used herein, the singular forms "a," "an," and "the" are intended to include the plural forms as well, unless the context clearly indicates otherwise.

It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10%, 5% of the stated value.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

A carbazole compound may be represented by Formula 1:

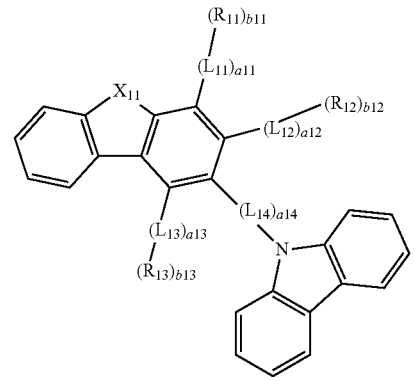

Formula 1 wherein in Formula 1, $X_{11}$ may be selected from an oxygen (O) atom and a sulfur (S) atom.

In Formula 1, $L_{11}$ to $L_{14}$ may be each independently selected from a substituted or unsubstituted $C_1$-$C_{60}$ alkylene group, a substituted or unsubstituted $C_2$-$C_{60}$ alkenylene group, a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, and a substituted or unsubstituted $C_1$-$C_{60}$ heteroarylene group;

at least one substituent of the substituted $C_1$-$C_{60}$ alkylene group, substituted $C_2$-$C_{60}$ alkenylene group, substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, and substituted $C_1$-$C_{60}$ heteroarylene group may be selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), and —B($Q_{16}$)($Q_{17}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_1$-$C_{60}$ alkenyl group, a $C_1$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), and —B($Q_{26}$)($Q_{27}$); and —N($Q_{31}$)($Q_{32}$), —Si($Q_{33}$)($Q_{34}$)($Q_{35}$), and —B($Q_{36}$)($Q_{37}$);

wherein $Q_1$ to $Q_7$, $Q_{11}$ to $Q_{17}$, $Q_{21}$ to $Q_{27}$, and $Q_{31}$ to $Q_{37}$ may be each independently selected from a hydrogen, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

In some embodiments, in Formula 1, $L_{11}$ to $L_{14}$ may be each independently selected from a phenylene group, a naphthylene group, a phenanthrenylene group, an anthracenylene group, a triphenylenylene group, a pyrenylene group, a chrysenylene group, a perylenylene group, a pyrrolylene group, an imidazolylene group, a pyridinylene group, a pyrazinylene group, a pyrimidinylene group, an indolylene group, a quinolinylene group, an isoquinolinylene group, a benzoquinolinylene group, a quinoxalinylene group, a quinazolinylene group, a phenanthridinylene group, an acridinylene group, a phenanthrolinylene group, a phenazinylene group, a furanylene group, a benzofuranylene group, a thiophenylene group, a benzothiophenylene group, a triazolylene group, an imidazopyridinylene group, and an imidazopyrimidinylene group; and a phenylene group, a naphthylene group, a phenanthrenylene group, an anthracenylene group, a triphenylenylene group, a pyrenylene group, a chrysenylene group, a perylenylene group, a pyrrolylene group, an imidazolylene group, a pyridinylene group, a pyrazinylene group, a pyrimidinylene group, an indolylene group, a quinolinylene group, an isoquinolinylene group, a benzoquinolinylene group, a quinoxalinylene group, a quinazolinylene group, a phenanthridinylene group, an acridinylene group, a phenanthrolinylene group, a phenazinylene group, a furanylene group, a benzofuranylene group, a thiophenylene group, a benzothiophenylene group, a triazolylene group, an imidazopyridinylene group, and an imidazopyrimidinylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a $C_6$-$C_{20}$ aryl group, a phenyl group-substituted with a phenyl group, a $C_1$-$C_{20}$ heteroaryl group, a monovalent non-aromatic condensed polycyclic group, a monovalent non-aromatic condensed heteropolycyclic group, and —Si($Q_{33}$)($Q_{34}$)($Q_{35}$);

$Q_{33}$ to $Q_{35}$ may be each independently selected from a hydrogen, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group a phthalazinyl group, a quinoxalinyl group, a cinnolinyl group, and a quinazolinyl group, but they are not limited thereto.

In some embodiments, in Formula 1, $L_{11}$ to $L_{14}$ may be each independently selected from Formulae 2-1 to 2-28, but they are not limited thereto:

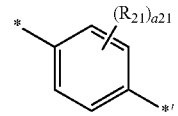

2-1

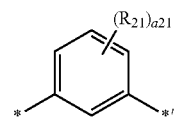

2-2

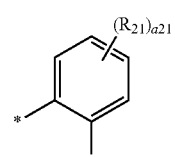

2-3

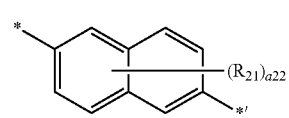

2-4

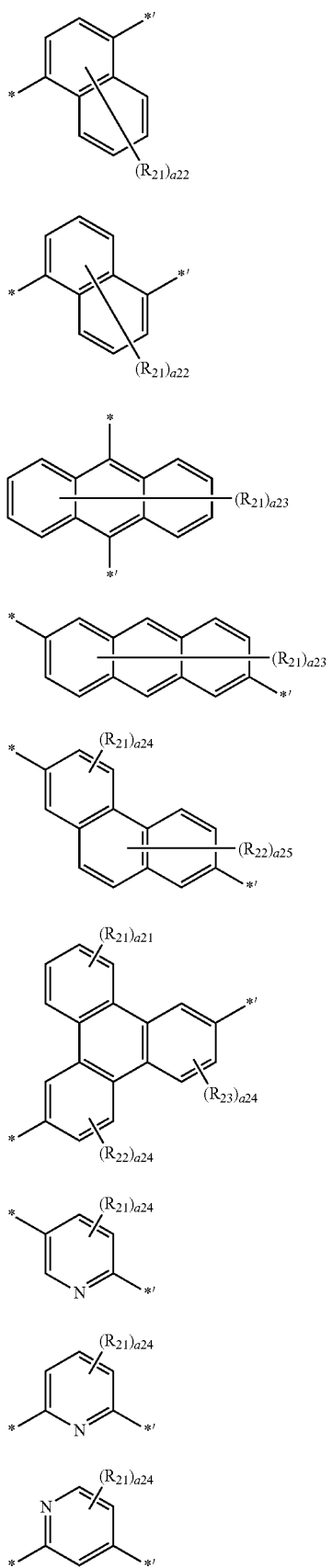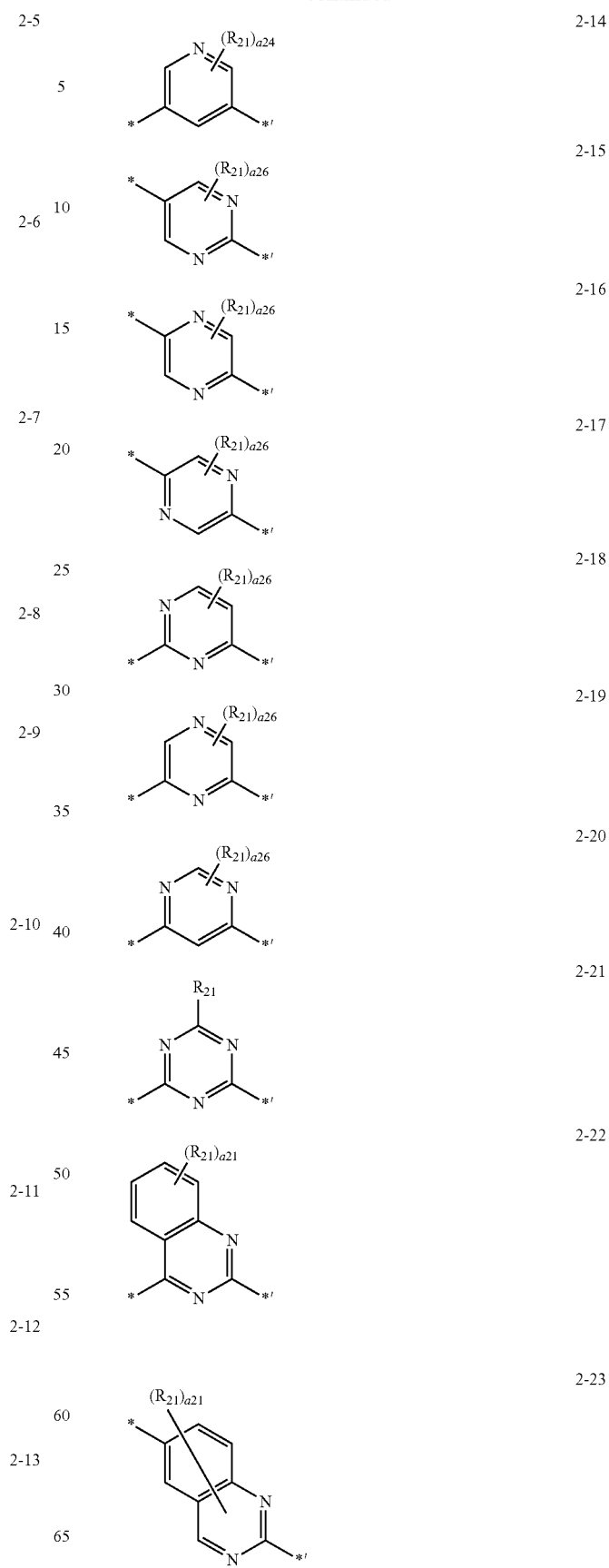

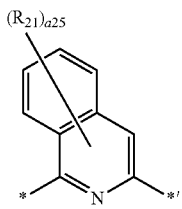
2-24

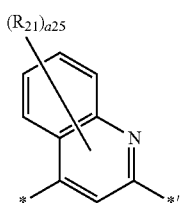
2-25

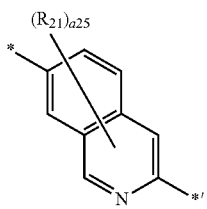
2-26

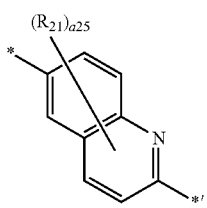
2-27

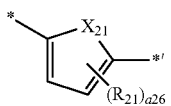
2-28 wherein in Formulae 2-1 to 2-28, $X_{21}$ may be selected from O and S;

$R_{21}$ to $R_{23}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a phenyl group-substituted with a phenyl group, a naphthyl group, an anthracenyl group, a triphenylenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, a quinoxalinyl group, and —Si($Q_{33}$)($Q_{34}$)($Q_{45}$);

wherein $Q_{33}$ to $Q_{45}$ may be each independently selected from a hydrogen, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group a phthalazinyl group, a quinoxalinyl group, a cinnolinyl group, and a quinazolinyl group;

a21 may be selected from 1, 2, 3, and 4;

a22 may be selected from 1, 2, 3, 4, 5, and 6;

a23 may be selected from 1, 2, 3, 4, 5, 6, 7, and 8;

a24 may be selected from 1, 2, and 3;

a25 may be selected from 1, 2, 3, 4, and 5;

a26 may be selected from 1 and 2;

* and *' each independently indicates a binding site to a neighboring atom.

In some embodiments, in Formula 1, $L_{11}$ to $L_{14}$ may be each independently selected from a phenylene group, a naphthylene group, a pyridinylene group, a pyrimidinylene group, a triazinylene group, a quinazolinylene group, a quinolinylene group, and an isoquinolinylene group; and a phenylene group, a naphthylene group, a pyridinylene group, a pyrimidinylene group, a triazinylene group, a quinazolinylene group, a quinolinylene group, and an isoquinolinylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a phenyl group-substituted with a phenyl group, a naphthyl group, an anthracenyl group, a triphenylenyl group, and a phenanthrenyl group; but they are not limited thereto.

In some embodiments, in Formula 1, $L_{11}$ to $L_{14}$ may be each independently selected from Formulae 3-1 to 3-14, but they are not limited thereto:

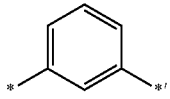
3-1

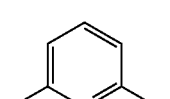
3-2

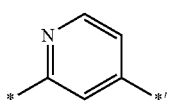
3-3

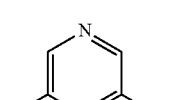
3-4

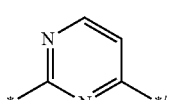
3-5

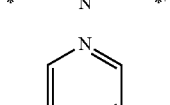
3-6

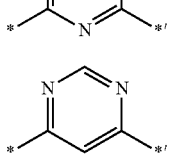
3-7

3-8
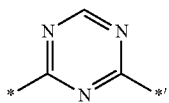

3-9
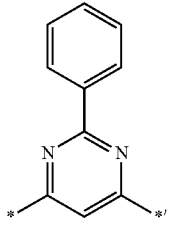

3-10
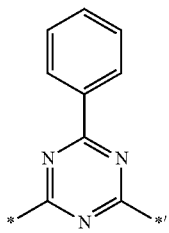

3-11
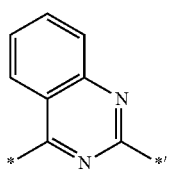

3-12
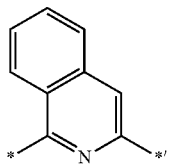

3-13
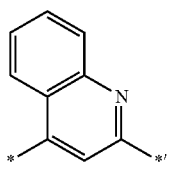

3-14
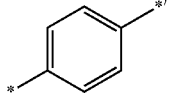

wherein in Formulae 3-1 to 3-14, and

\* and \*' each independently indicates a binding site to a neighboring atom.

In Formula 1, a11 indicates the number of $L_{11}$, and a11 may be selected from 0, 1, 2, 3, 4, and 5. In some embodiments, a11 in Formula 1 may be selected from 0, 1, and 2, but is not limited thereto. When a11 is 0, $(L_{11})_{a11}$ may be a single bond. When a11 is 2 or more, groups $L_{11}$ may be identical or different. a12 to a14 may be understood by referring to the descriptions for a11 and a structure of Formula 1. In Formula 1, a12 to a14 may be each independently selected from 0, 1, 2, 3, 4, and 5.

In some embodiments, in Formula 1, a12 to a14 may be selected from 0, 1, and 2, but it is not limited thereto.

In some embodiments, in Formula 1, a11 to a13 may be each independently selected from 0 and 1, but they are not limited thereto.

In some embodiments, in Formula 1, a14 may be 0, but it is not limited thereto.

In Formula 1, $R_{11}$ to $R_{13}$ may be each independently selected from $R_{ET}$, a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —N($Q_1$)($Q_2$), —Si($Q_3$)($Q_4$)($Q_5$), and —B($Q_6$)($Q_7$);

at least one selected from $R_{11}$ to $R_{13}$ may be $R_{ET}$;

at least one substituent of the substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group may be selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), and —B($Q_{16}$)($Q_{17}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_1$-$C_{60}$ alkenyl group, a $C_1$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$N(Q_{21})(Q_{22})$, —$Si(Q_{23})(Q_{24})(Q_{25})$, and —$B(Q_{26})(Q_{27})$; and —$N(Q_{31})(Q_{32})$, —$Si(Q_{33})(Q_{34})(Q_{35})$, and —$B(Q_{36})(Q_{37})$;

wherein $Q_1$ to $Q_7$, $Q_{11}$ to $Q_{17}$, $Q_{21}$ to $Q_{27}$, and $Q_{31}$ to $Q_{37}$ may be each independently selected from a hydrogen, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group, and the descriptions for $R_{ET}$ will be described below.

In some embodiments, in Formula 1, $R_{11}$ to $R_{13}$ may be each independently selected from $R_{ET}$, a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{20}$ alkyl group, a substituted or unsubstituted $C_1$-$C_{20}$ alkoxy group, a substituted or unsubstituted $C_6$-$C_{20}$ aryl group, a substituted or unsubstituted $C_1$-$C_{20}$ heteroaryl group, a substituted or unsubstituted monovalent non-aromatic condensed polycyclic group, and a substituted or unsubstituted monovalent non-aromatic condensed heteropolycyclic group;

at least one of $R_{11}$ to $R_{13}$ may be $R_{ET}$, but they are not limited thereto.

In some embodiments, $R_{11}$ to $R_{13}$ may be each independently selected from $R_{ET}$, a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a $C_1$-$C_{20}$ alkyl group, and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof;

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, an imidazopyrimidinyl group, a pyridobenzofuranyl group, a pyrimidobenzofuranyl group, a pyridobenzothiophenyl group, and a pyrimidobenzothiophenyl group;

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, phenanthridinyl, an acridinyl group, phenanthrolinyl, phenazinyl, a benzoimidazolyl group, a benzofuranyl group, a benzothiophenyl group, an isobenzothiazolyl group, a benzoxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, an imidazopyrimidinyl group, a pyridobenzofuranyl group, a pyrimidobenzofuranyl group, a pyridobenzothiophenyl group, and a pyrimidobenzothiophenyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a phenyl group- substituted with a $C_1$-$C_{20}$ alkyl group, a phenyl group-substituted with a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, an imidazopyrimidinyl group, and —Si($Q_{33}$)($Q_{34}$)($Q_{35}$); and —Si($Q_3$)($Q_4$)($Q_5$);

wherein $Q_3$ to $Q_5$ and $Q_{33}$ to $Q_{35}$ may be each independently selected from a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, and a quinoxalinyl group;

at least one of $R_{11}$ to $R_{13}$ may be $R_{ET}$, but they are not limited thereto.

In some embodiments, $R_{11}$ to $R_{13}$ may be each independently selected from $R_{ET}$, a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof; and —Si($Q_3$)($Q_4$)($Q_5$);

wherein $Q_3$ to $Q_5$ may be each independently selected from a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, and a quinoxalinyl group, at least one of $R_{11}$ to $R_{13}$ may be $R_{ET}$, but they are not limited thereto.

In some embodiments, in Formula 1, $R_{14}$ and $R_{15}$ may be a hydrogen, but they are not limited thereto.

In Formula 1, b11 indicates the number of groups $R_{11}$, and b 11 may be selected from 1, 2, 3, and 4. When b11 is 2 or more, groups $R_{11}$ may be identical or different. b12 and b13 may be understood by referring to the descriptions for b11 and the structure of Formula 1.

In Formula 1, b12 and b13 may be each independently selected from 1, 2, 3, and 4.

In Formula 1, $R_{ET}$ may be selected from Formulae 9-1 to 9-52:

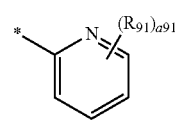

9-1

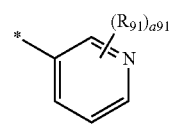

9-2

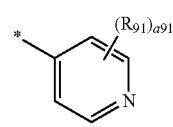

9-3

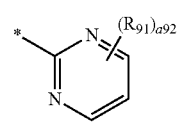

9-4

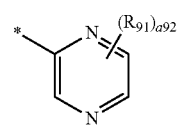

9-5

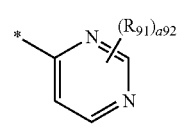

9-6

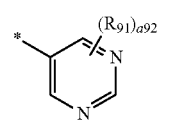

9-7

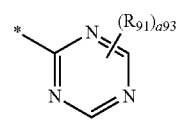

9-8

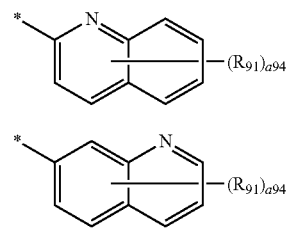

9-9

9-10

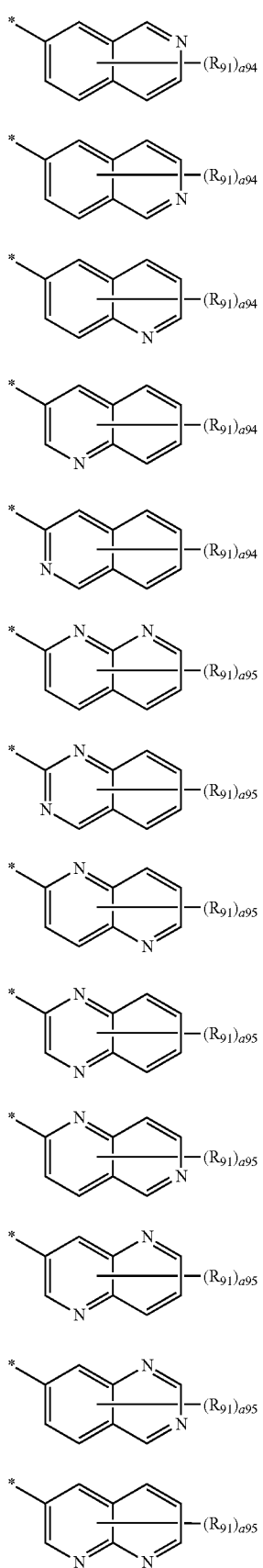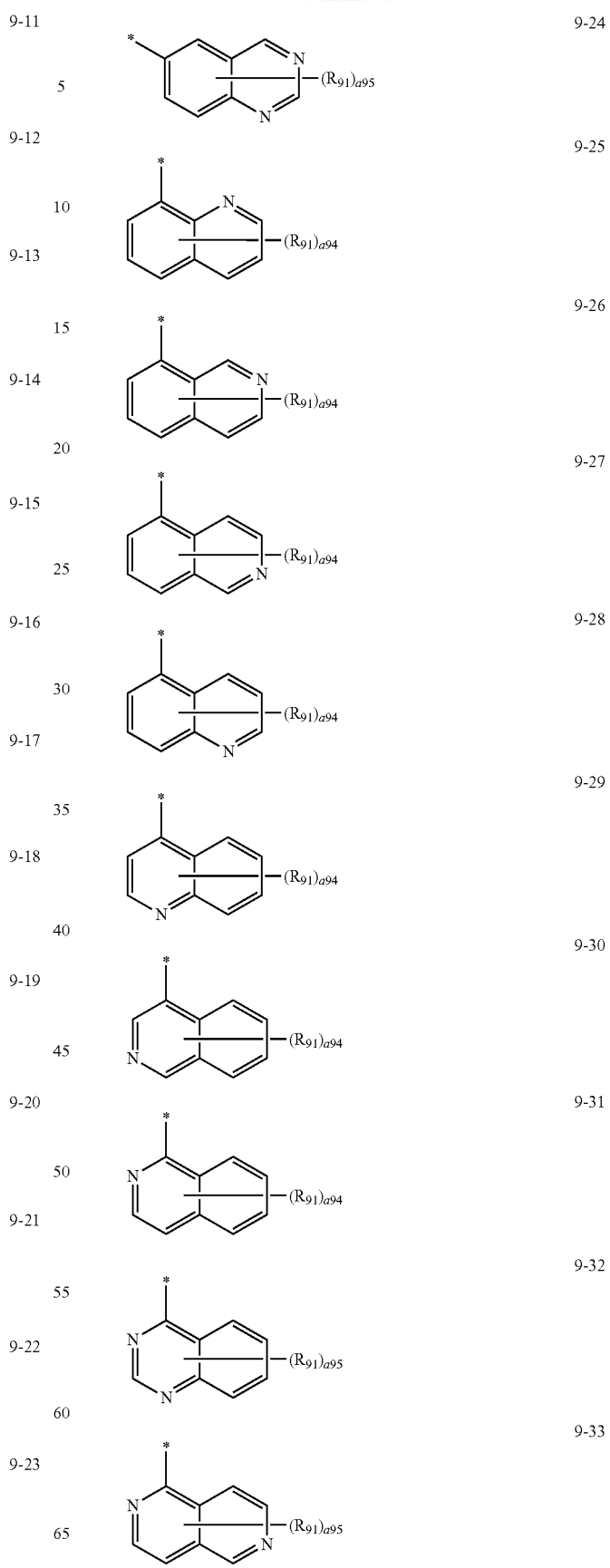

-continued 9-34 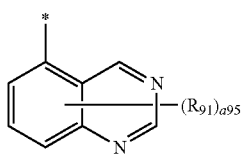

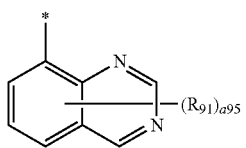  9-35

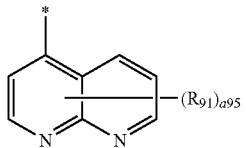  9-36

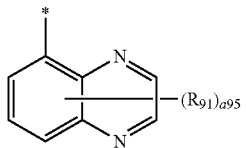

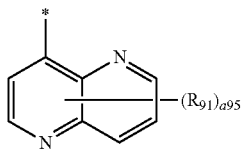

9-37

9-38

9-39 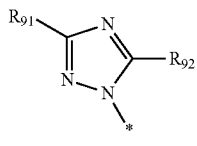

9-40 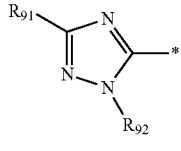

9-41 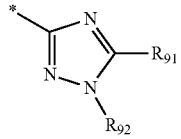

9-42 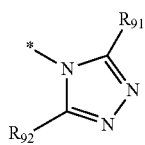

9-43 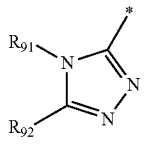

-continued 9-44 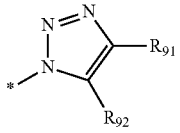

9-45 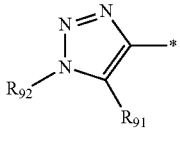

9-46 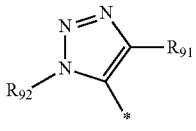

9-47 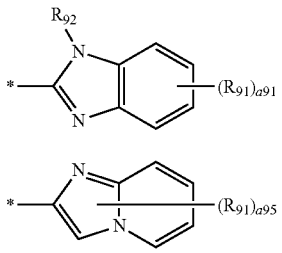

9-48

9-49

9-50

9-51 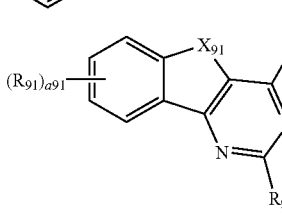

9-52 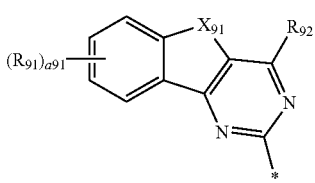

wherein in Formulae 9-1 to 9-52, $X_{91}$ may be selected from O and S;

$R_{91}$ and $R_{92}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_1$-$C_{60}$ alkoxy group, a $C_6$-$C_{60}$ aryl group, a $C_6$-$C_{60}$ aryloxy group, a $C_6$-$C_{60}$ arylthio group, and a $C_1$-$C_{60}$ heteroaryl group;

a91 may be selected from 1, 2, 3, and 4;
a92 may be selected from 1, 2, and 3;
a93 may be selected from 1 and 2;
a94 may be selected from 1, 2, 3, 4, 5, and 6; and
a95 may be selected from 1, 2, 3, 4, and 5; and
* indicates a binding site to a neighboring atom.
In some embodiments, in Formula 1, at least one of $R_{11}$ to $R_{13}$ may be $R_{ET}$, and $R_{ET}$ may be selected from Formulae 9-1 to 9-52, but they are not limited thereto:
9-1
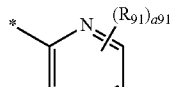
9-2
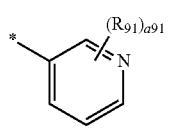
9-3
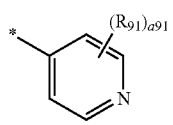
9-4
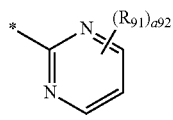
9-5
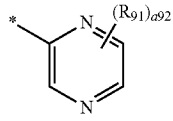
9-6
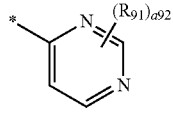
9-7
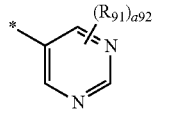
9-8
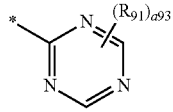
9-9
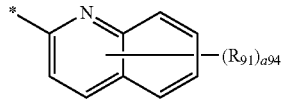
9-10
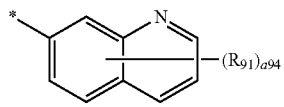
9-11
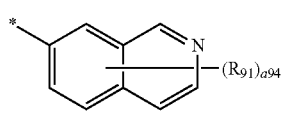
-continued
9-12
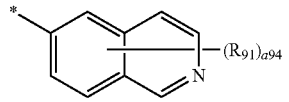
9-13
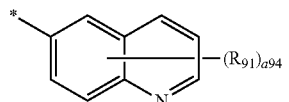
9-14
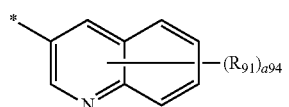
9-15
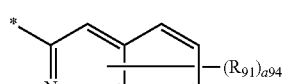
9-16
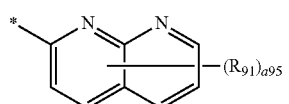
9-17
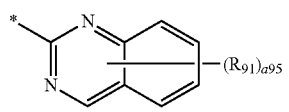
9-18
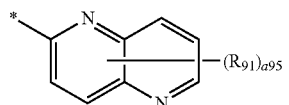
9-19
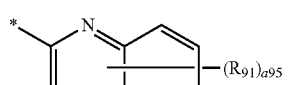
9-20
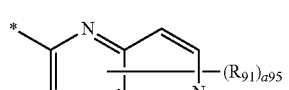
9-21
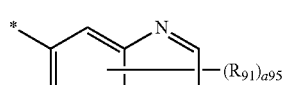
9-22
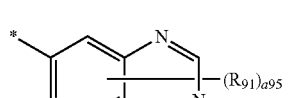
9-23
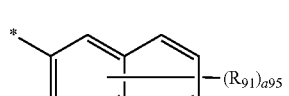
9-24
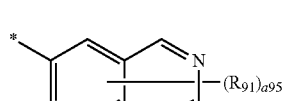

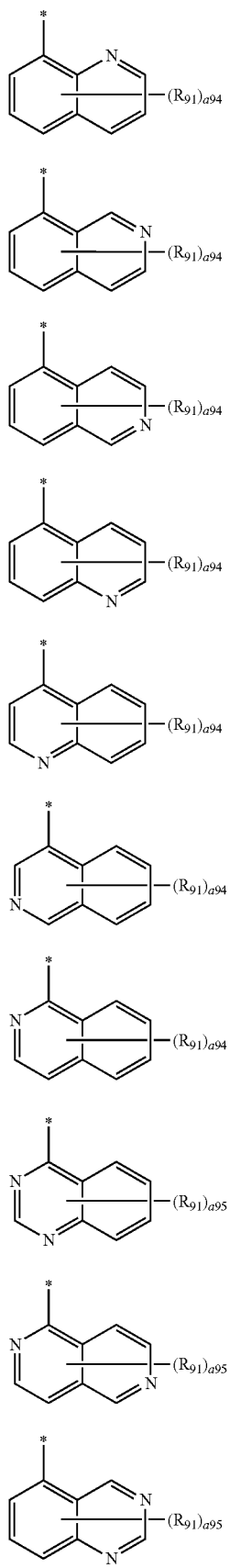
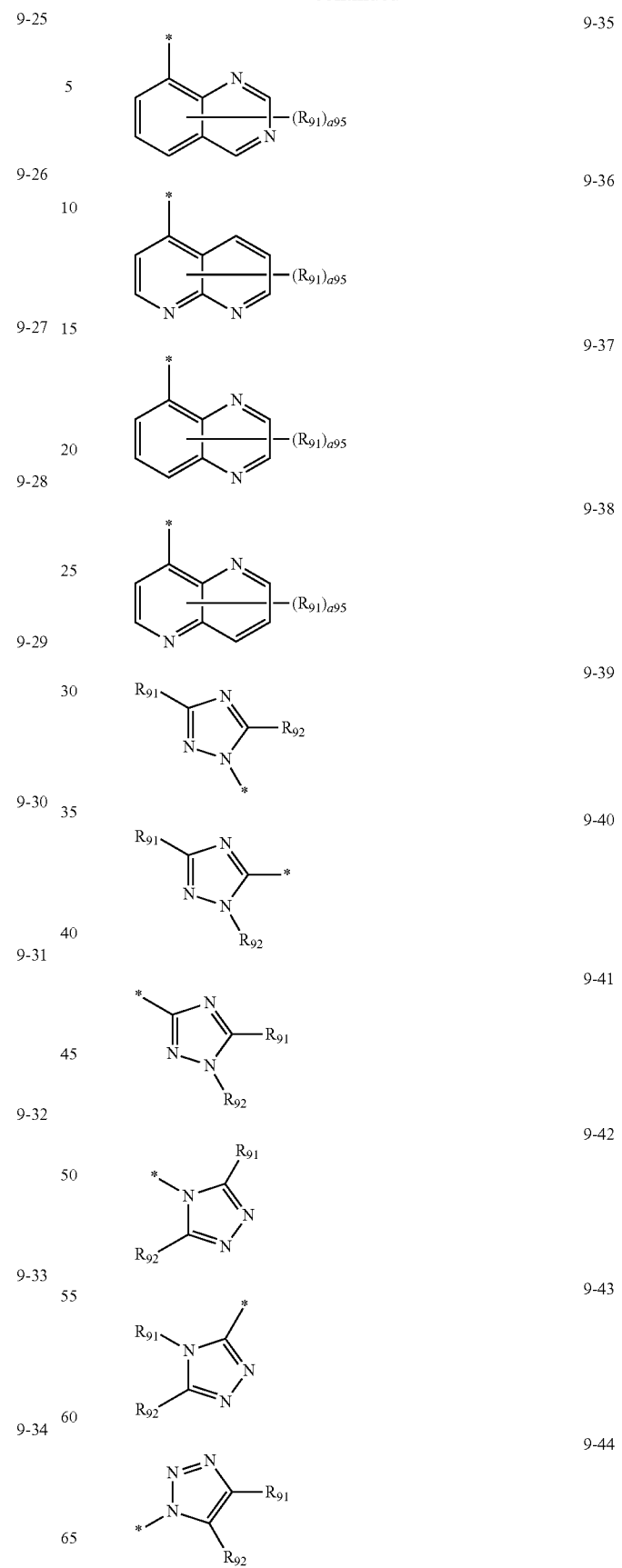

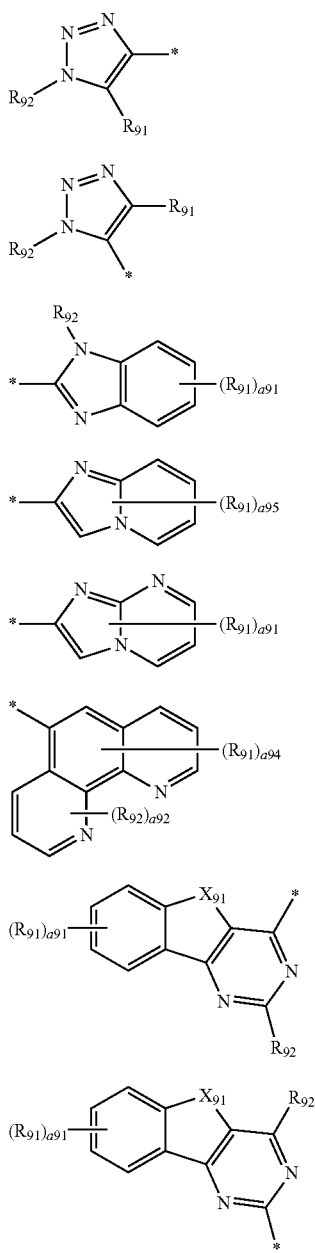
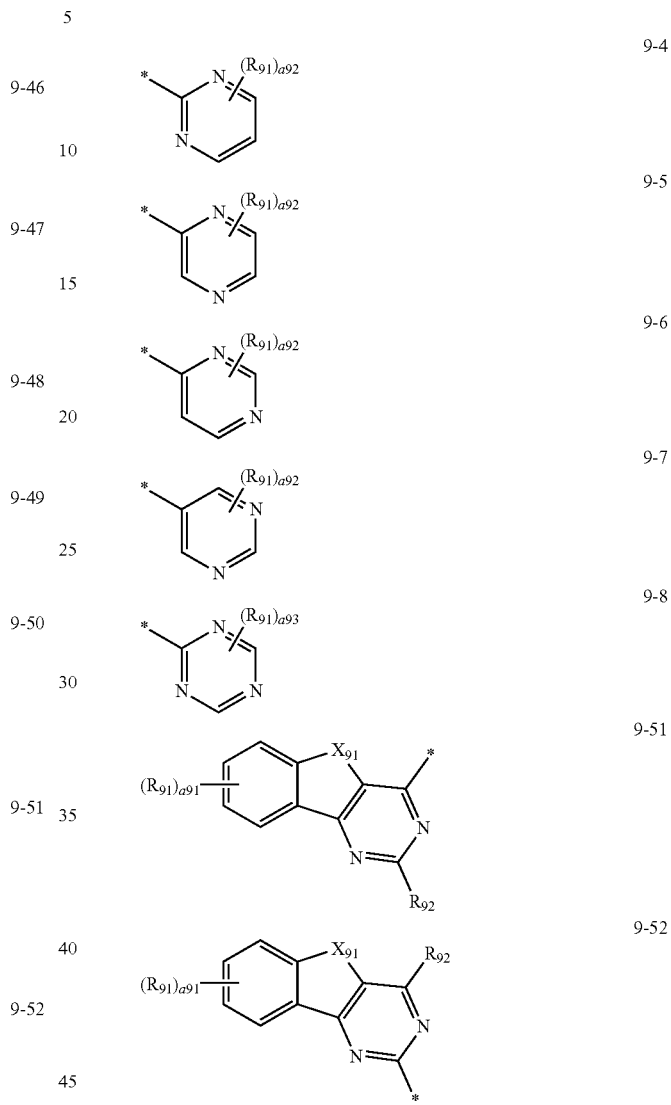

wherein in Formulae 9-1 to 9-52, $X_{91}$ may be selected from O and S;

$R_{91}$ and $R_{92}$ may be each independently selected from a hydrogen, a deuterium, —F, —Cl, —Br, —I, a cyano group, a nitro group, a $C_1$-$C_{20}$ alkyl group, a $C_1$-$C_{20}$ alkoxy group, a phenyl group, a biphenyl group, a naphthyl group, an anthracenyl group, a pyrenyl group, a phenanthrenyl group, a pyridinyl group, a pyrimidinyl group, a triazinyl group, a quinolinyl group, an isoquinolinyl group, and a quinazolinyl group;

a91 may be selected from 1, 2, 3, and 4;
a92 may be selected from 1, 2, and 3;
a93 may be selected from 1 and 2;
a94 may be selected from 1, 2, 3, 4, 5, and 6;
a95 may be selected from 1, 2, 3, 4, and 5; and
* indicates a binding site to a neighboring atom.

In some embodiments, in Formula 1, at least one of $R_{11}$ to $R_{13}$ may be $R_{ET}$, and $R_{ET}$ may be selected from Formulae 9-4 to 9-8, 9-51, and 9-52, but they are not limited thereto:

wherein in Formulae 9-4 to 9-8, 9-51, and 9-52, $X_{91}$ may be selected from O and S;

$R_{91}$ and $R_{92}$ may be each independently selected from a hydrogen, a deuterium, F, —Cl, —Br, —I, a cyano group, a nitro group, a $C_1$-$C_{20}$ alkyl group, a $C_1$-$C_{20}$ alkoxy group, a phenyl group, a biphenyl group, a naphthyl group, an anthracenyl group, a pyrenyl group, a phenanthrenyl group, a pyridinyl group, a pyrimidinyl group, a triazinyl group, a quinolinyl group, an isoquinolinyl group, and a quinazolinyl group;

a91 may be selected from 1, 2, 3, and 4;
a92 may be selected from 1, 2, and 3;
a93 may be selected from 1 and 2; and
* indicates a binding site to a neighboring atom.

In some embodiments, in Formula 1, at least one of $R_{11}$ to $R_{13}$ may be $R_{ET}$, and $R_{ET}$ may be selected from Formulae 10-1 to 10-7, but they are not limited thereto.

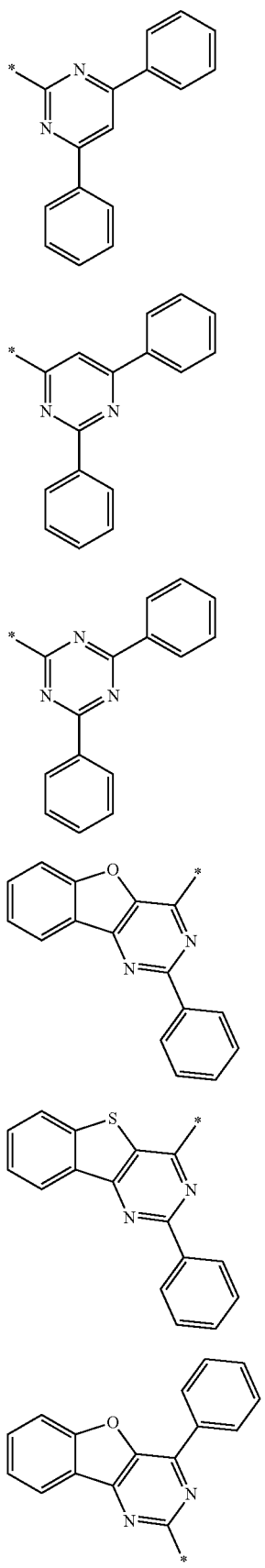

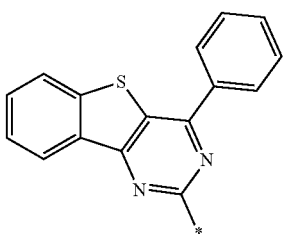

-continued wherein in Formulae 10-1 to 10-7,
* indicates a binding site to a neighboring atom.

In some embodiments, the carbazole compound may be selected from a group represented by one of Formulae 1-1 to 1-3:

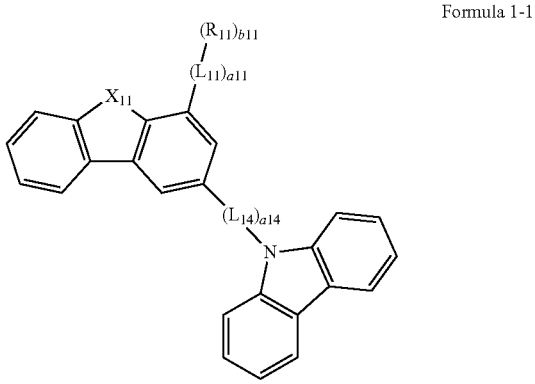

Formula 1-1

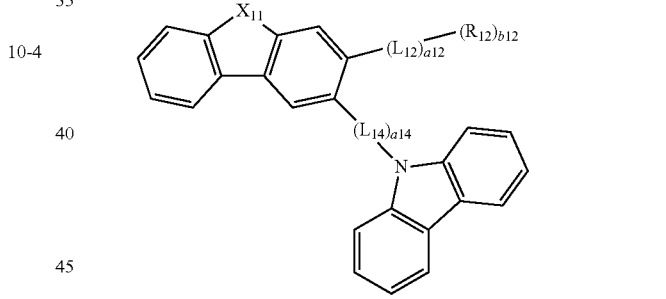

Formula 1-2

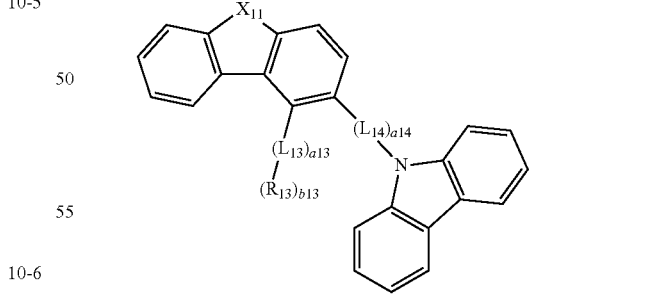

Formula 1-3 wherein in Formulae 1-1 to 1-3, $X_{11}$, $L_{11}$ to $L_{14}$, a11 to a14, $R_{11}$ to $R_{13}$, and b11 to b13 may be the same as in Formula 1;

$R_{11}$ in Formula 1-1, $R_{12}$ in Formula 1-2, and $R_{13}$ in Formula 1-3 may be each independently $R_{ET}$.

In some embodiments, in Formulae 1-1 to 1-3, $X_{11}$ may be selected from O and S;

$L_{11}$ to $L_{14}$ may be each independently selected from Formula 2-1 to 2-28;

a11 to a14 may be each independently selected from 0 and 1;

$R_{11}$ to $R_{13}$ may be each independently selected from $R_{ET}$, a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof; and —Si($Q_3$)($Q_4$)($Q_5$);

wherein $Q_3$ to $Q_5$ may be each independently selected from a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, and a quinoxalinyl group, at least one selected from $R_{11}$ to $R_{13}$ may be $R_{ET}$;

b11 to b13 may be each independently selected from 1, 2, 3, and 4;

$R_{ET}$ may be selected from Formulae 9-1 to 9-52, but they are not limited thereto.

In some embodiments, the carbazole compound may be selected from a group represented by one of Formulae 1-1A, 1-2A, and 1-3A:

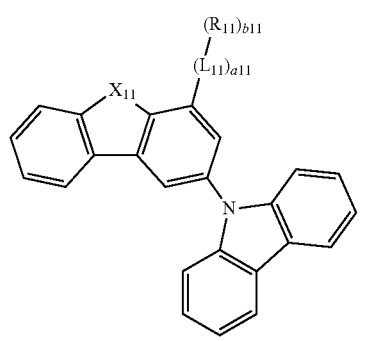

Formula 1-1A

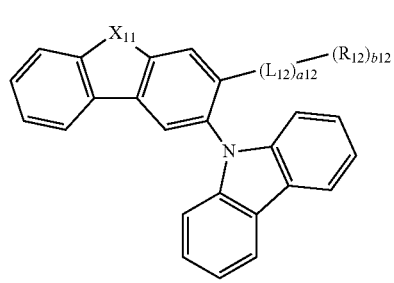

Formula 1-2A

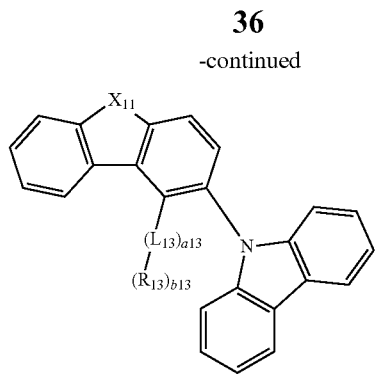

Formula 1-3A wherein in Formulae 1-1A, 1-2A, and 1-3A, $X_{11}$, $L_{11}$ to $L_{13}$, a11 to a13, $R_{11}$ to $R_{13}$, and b11 to b13 may be the same as in Formula 1, and $R_{11}$ in Formula 1-1A, $R_{12}$ in Formula 1-2A, and $R_{13}$ in Formula 1-3A may be each independently $R_{ET}$.

In some embodiments, the carbazole compound may be represented by Formula 1-1B:

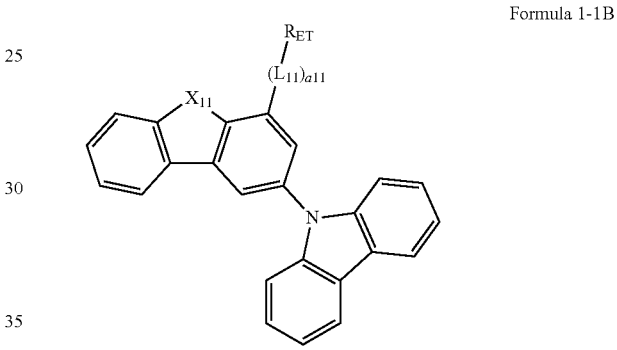

Formula 1-1B wherein in Formula 1-1B, $X_{11}$, $L_{11}$, and a11 may be understood by referring to the descriptions above, and $R_{ET}$ may be selected from Formulae 10-1 to 10-7:

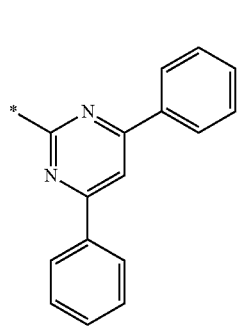

10-1

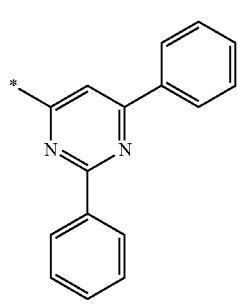

10-2

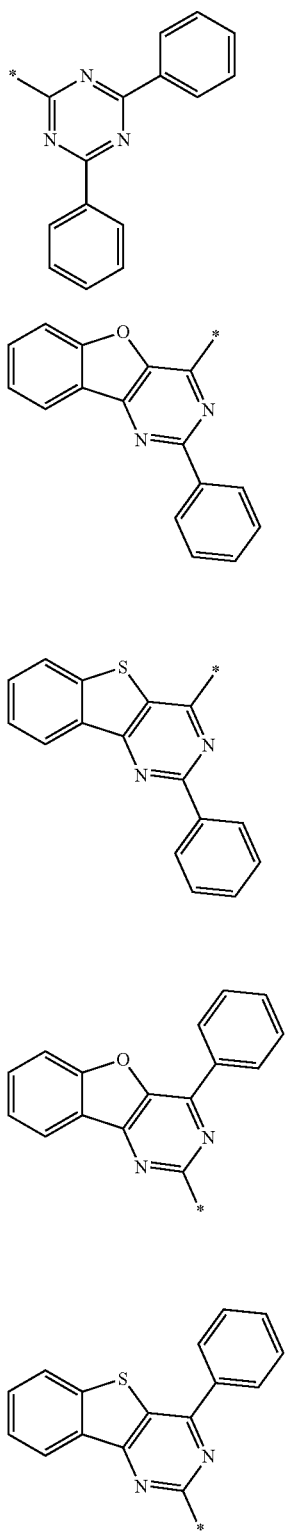
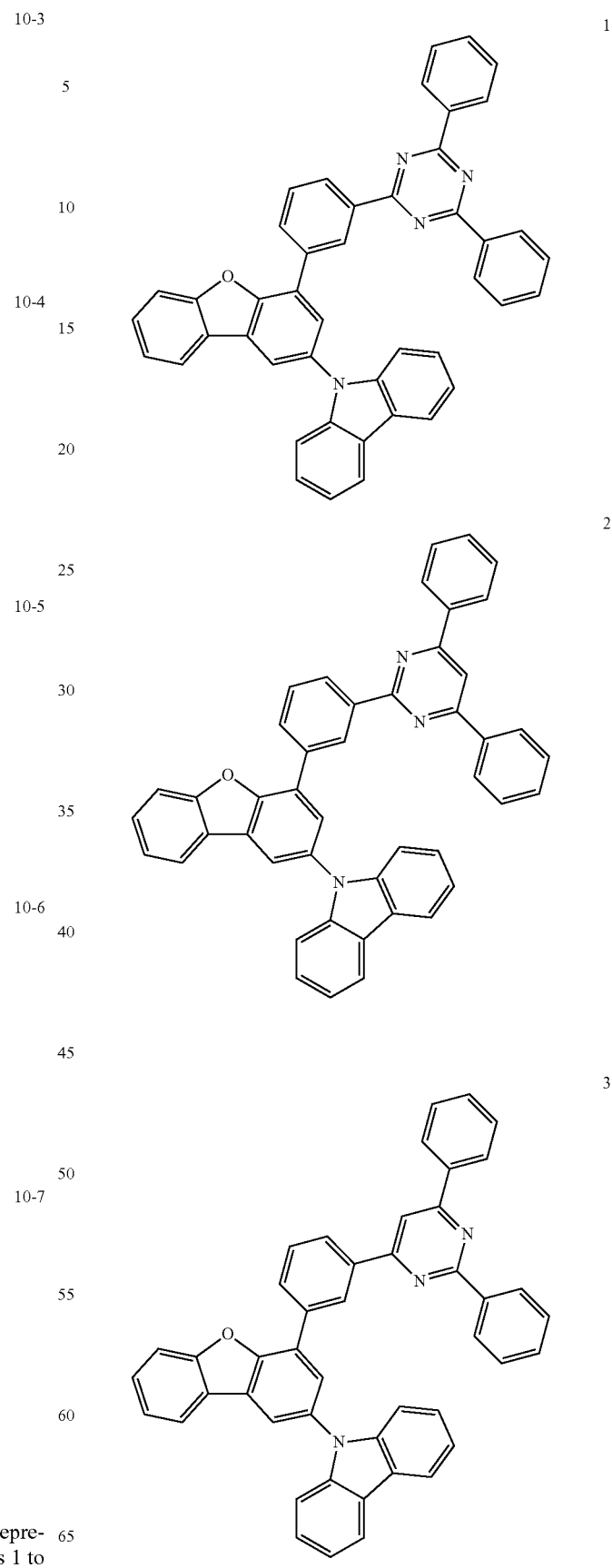
wherein in Formulae 10-1 to 10-7,
* indicates a binding site to a neighboring atom.
In some embodiments, the carbazole compound represented by Formula 1 may be selected from Compounds 1 to 20 below, but it is not limited thereto:

4
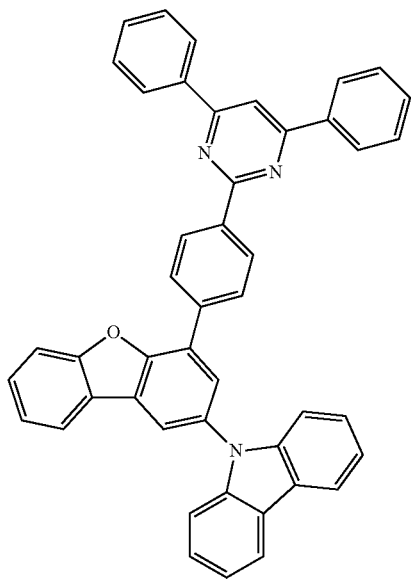
5
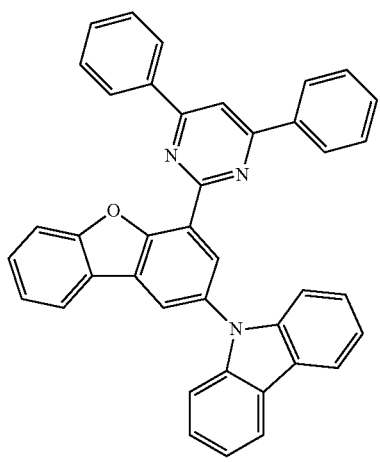
6
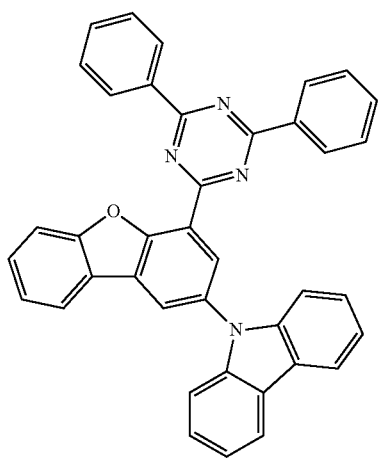
7
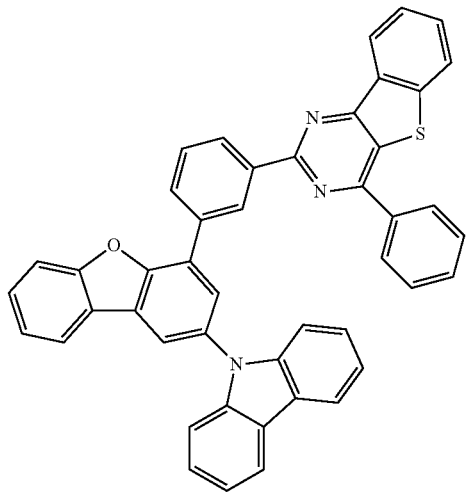
8
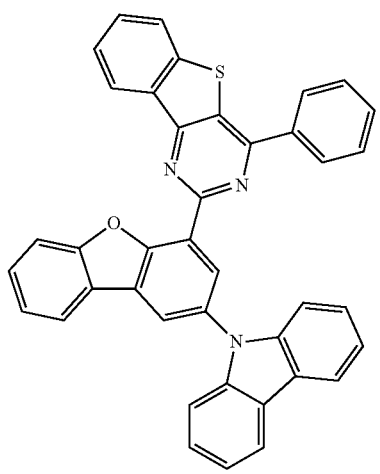
9
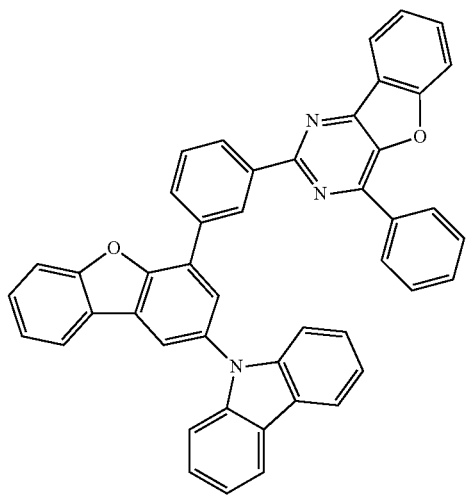

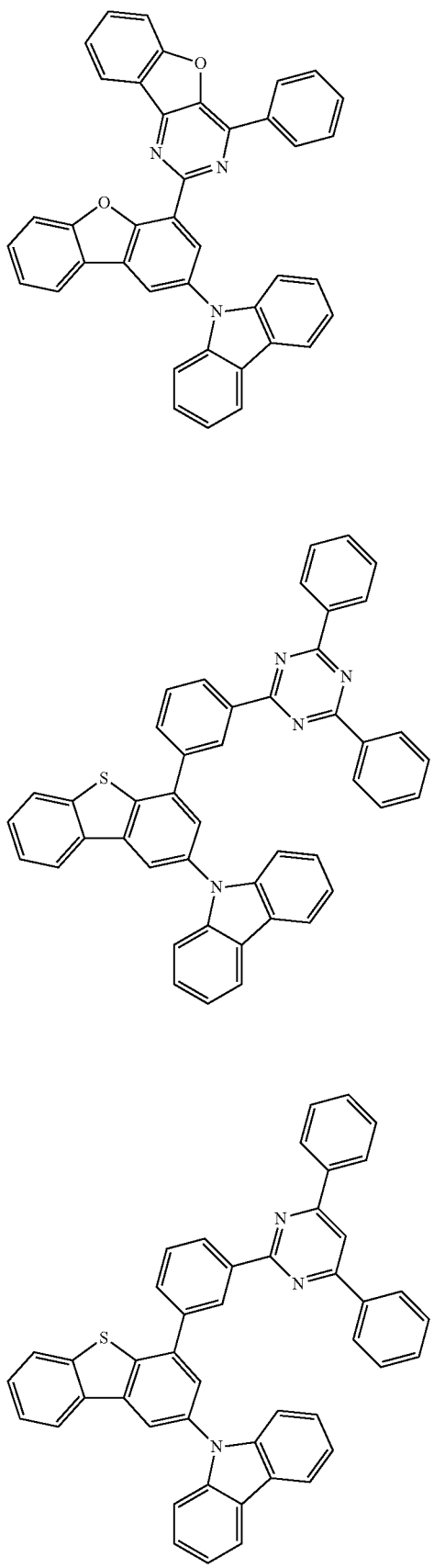
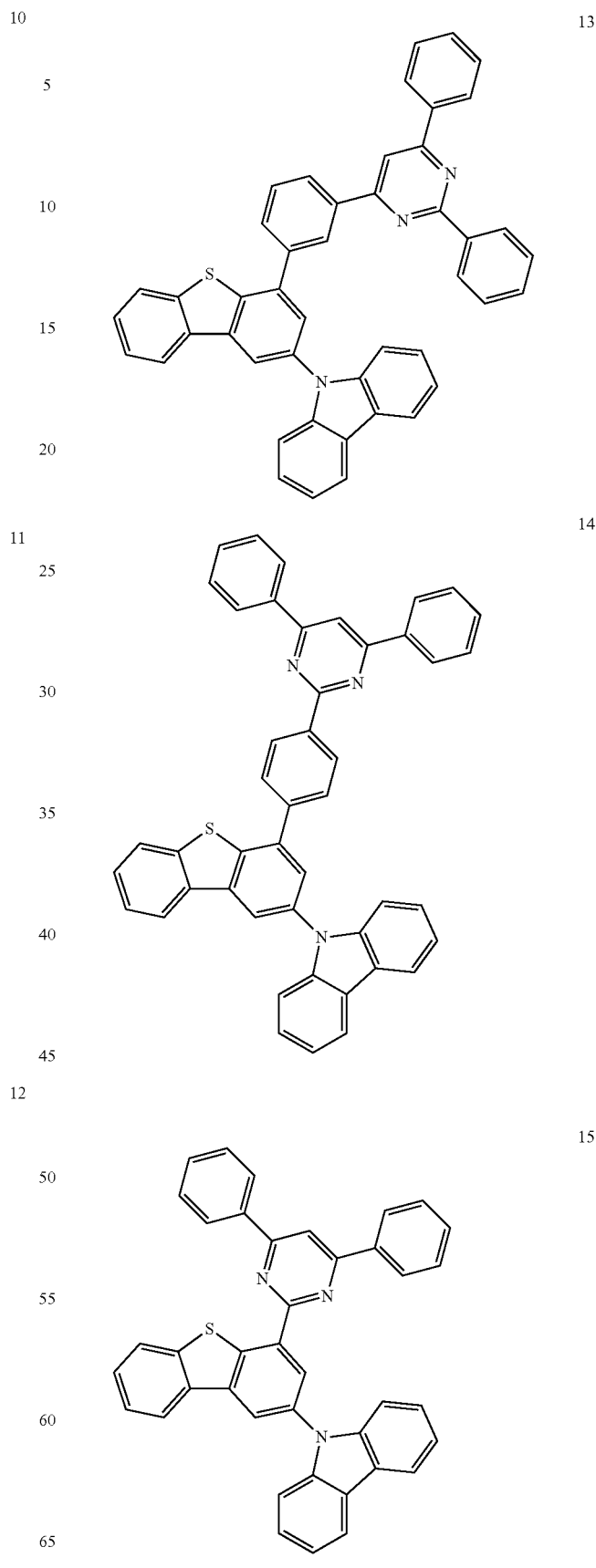

16
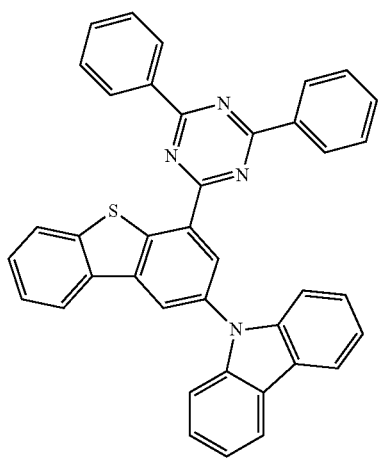

19
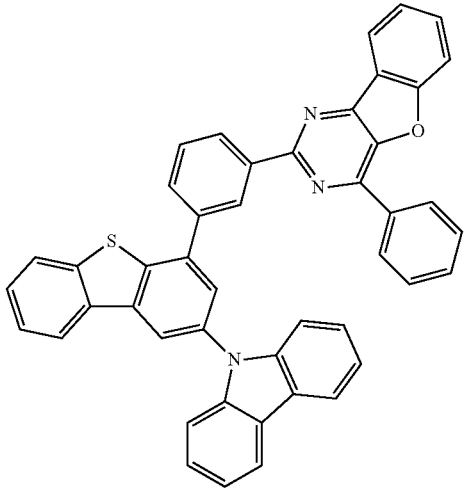

17
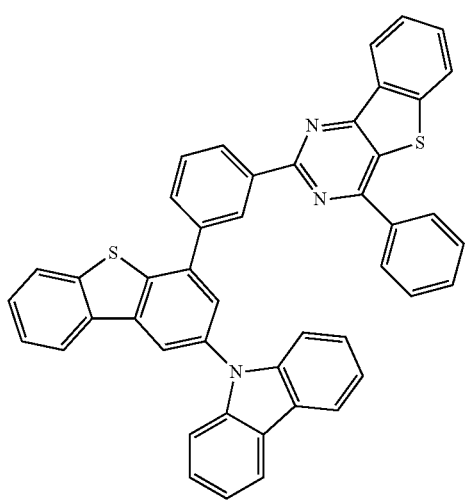

20
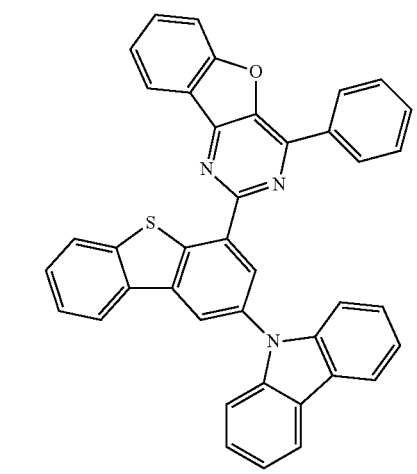

18
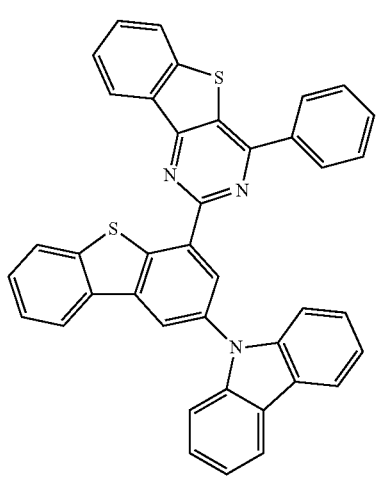

The carbazole compound represented by Formula 1 may have 1) "a carbazole ring" that is bound to "No. 2 carbon" of "ring A", optionally having "-$(L_{14})_{a14}$-" therebetween (referring to Formula 1' below) and 2) at least one of $R_{11}$ to $R_{13}$ may be each independently selected from Formulae 9-1 to 9-52. Accordingly, an electron density of "ring A" in Formula 1' may be effectively varied, and a charge transporting ability of the carbazole compound represented by Formula 1' may be easily controlled by varying a substituent of $R_{11}$ to $R_{13}$.

In addition, the carbazole compound represented by Formula 1 includes a carbazolyl group having an excellent hole transporting ability and $R_{ET}$ having an excellent electron transporting ability in one molecule, thereby achieving a bipolar character of the carbazole compound.

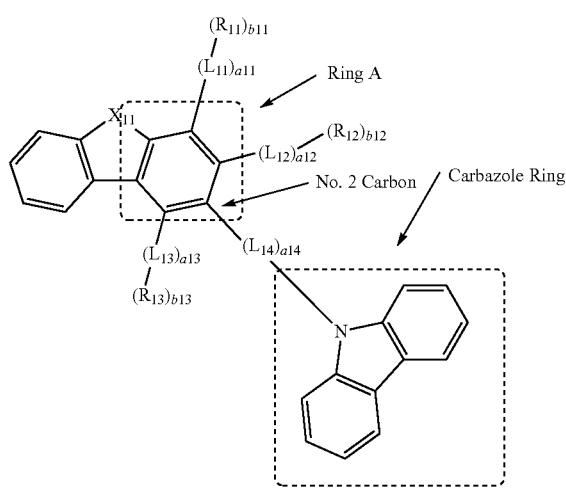

As an example, the highest occupied molecular orbital (HOMO) energy level, the lowest unoccupied molecular orbital (LUMO) energy level, a S1 energy level, and a T1 energy level of the carbazole compounds represented by Formula 1 were evaluated by using Gaussian 09 which performs molecular structure optimizations by using density functional theory (DFT) based on the B3LYP. The results thereof are shown in Table 1 below.

TABLE 1

|  | HOMO (eV) | LUMO (eV) | $S_1$ (eV) | $T_1$ (eV) |
|---|---|---|---|---|
| Compound 1 | −5.297 | −1.881 | 3.050 | 2.926 |
| Compound 2 | −5.284 | −1.729 | 3.184 | 2.873 |
| Compound 4 | −5.288 | −1.701 | 3.161 | 2.832 |
| Compound 5 | −5.259 | −1.769 | 3.020 | 2.795 |
| Compound 6 | −5.347 | −2.042 | 2.801 | 2.635 |
| Compound 7 | −5.314 | −1.834 | 3.148 | 2.829 |
| Compound 8 | −5.254 | −1.858 | 3.009 | 2.771 |
| Compound 9 | −5.298 | −1.923 | 3.045 | 2.828 |
| Compound 10 | −5.241 | −1.951 | 2.904 | 2.800 |
| Compound 11 | −5.322 | −1.912 | 3.047 | 2.952 |
| Compound 12 | −5.265 | −1.730 | 3.186 | 2.934 |
| Compound 13 | −5.376 | −1.749 | 3.181 | 2.936 |
| Compound 14 | −5.281 | −1.727 | 3.183 | 2.798 |
| Compound 15 | −5.233 | −1.819 | 2.981 | 2.708 |
| Compound 16 | −5.330 | −2.080 | 2.750 | 2.560 |
| Compound 17 | −5.224 | −1.891 | 3.005 | 2.850 |
| Compound 18 | −5.226 | −1.947 | 2.882 | 2.698 |
| Compound 19 | −5.224 | −1.976 | 2.922 | 2.843 |
| Compound 20 | −5.222 | −2.045 | 2.780 | 2.701 |
| Compound A | −5.303 | −1.506 | 3.340 | 3.061 |
| Compound B | −5.329 | −1.536 | 3.282 | 2.979 |

A method of synthesizing the carbazole compound represented by Formula 1 may be apparent to one of ordinary skill in the art by referring to Synthesis Examples described below.

Therefore, it may be appropriate to use the carbazole compound represented by Formula 1 in an organic layer of an organic light-emitting device, for example as a host in an emission layer of the organic layer. Thus, according to another aspect, an organic light-emitting device is provided that may include:
a first electrode;
a second electrode; and
an organic layer that is disposed between the first electrode and the second electrode,
wherein the organic layer includes an emission layer and at least one carbazole compound represented by Formula 1.

The organic light-emitting device including the carbazole compound may have excellent power consumption, efficiency, luminance, and lifespan characteristics.

The carbazole compound represented by Formula 1 may be included in between a pair of electrodes of the organic light-emitting device. In some embodiments, the carbazole compound may be included in at least one selected from the emission layer, a hole transport region (for example, including at least one selected from a hole injection layer, a hole transport layer, and an electron blocking layer) disposed between the first electrode and the emission layer, and an electron transport region (for example, including at least one selected from a hole blocking layer, an electron transport layer, and an electron injection layer) disposed between the emission layer and the second electrode. In some embodiments, the carbazole compound represented by Formula 1 may be included in the emission layer. Here, the emission layer may further include a dopant, and the carbazole compound included in the emission layer may serve as a host. The emission layer may be a green emission layer that emits green light or a red emission layer that emits red light, and the dopant may be a phosphorescent dopant.

As used herein, the expression the "(organic layer) includes at least one carbazole compound" may be construed as meaning the "(organic layer) may include one carbazole compound represented by Formula 1 or two different carbazole compounds represented by Formula 1".

For example, the organic layer may include only Compound 1 as the carbazole compound. In this regard, Compound 1 may be included in the emission layer of the organic light-emitting device. Alternatively, the organic layer may include Compound 1 and Compound 2 as the carbazole compounds. In this regard, Compound 1 and Compound 2 may be included in the same layer (for example, both Compound 1 and Compound 2 may be included in the emission layer) or in different layers, respectively.

The first electrode may be an anode, which is a hole injection electrode, and the second electrode may be a cathode, which is an electron injection electrode. Alternatively, the first electrode may be a cathode, which is an electron injection electrode, and the second electrode may be an anode, which is a hole injection electrode.

For example, the first electrode may be an anode, the second electrode may be a cathode, and the organic layer may include i) a hole-transport region disposed between the first electrode and the emission layer, wherein the hole-transport region includes at least one selected from a hole injection layer, a hole-transport layer, and an electron blocking layer; and ii) an electron transport region disposed between the emission layer and the second electrode, wherein the electron-transporting region includes at least one selected from a hole blocking layer, an electron transport layer, and an electron injection layer.

As used herein, the term the "organic layer" refers to a single and/or a plurality of layers disposed between the first electrode and the second electrode in an organic light-emitting device. The "organic layer" may include not only organic compounds but also organometallic complexes including metals.

FIG. 1 is a schematic view of an organic light-emitting device 10 according to an embodiment. Hereinafter, a structure and a method of manufacturing the organic light-emitting device according to an embodiment will be described with reference to FIG. 1. The organic light-emitting device 10 includes a first electrode 11, an organic layer 15, and a second electrode 19, which are sequentially layered in the stated order.

A substrate may be additionally disposed under the first electrode 11 or on the second electrode 19. The substrate may be a conventional substrate that is used in an organic light-emitting device, such as glass substrate or a transparent plastic substrate, each having excellent mechanical strength, thermal stability, transparency, surface smoothness, ease of handling, and water repellency.

The first electrode 11 may be formed by depositing or sputtering a material for forming the first electrode on the substrate. The first electrode 11 may be an anode. The material for the first electrode 11 may be selected from materials with a high work function for an easy hole injection. The first electrode 11 may be a reflective electrode, a semi-transmissive electrode, or a transmissive electrode. The material for the first electrode 110 may be selected from indium tin oxide (ITO), indium zinc oxide (IZO), tin oxide ($SnO_2$), and zinc oxide (ZnO). Alternatively, a metal such as magnesium (Mg), aluminum (Al), aluminum-lithium (Al—Li), calcium (Ca), magnesium-indium (Mg—In), and magnesium-silver (Mg—Ag).

The first electrode 11 may have a single layer structure or a multi-layer structure including two or more layers. For example, the first electrode 11 may have a triple-layer structure of ITO/Ag/ITO, but it is not limited thereto.

The organic layer 15 is disposed on the first electrode 11.

The organic layer 15 may include a hole transport region, an emission layer, and an electron transport region.

The hole transport region may be disposed between the first electrode 11 and the emission layer.

The hole transport region may include at least one selected from a hole injection layer, hole transport layer, electron blocking layer, and buffer layer.

The hole transport region may only include a hole injection layer or a hole transport layer. Alternatively, the hole transport region may include a structure in which a hole injection layer/a hole transport layer or a hole injection layer/a hole transport layer/an electron blocking layer are sequentially layered on the first electrode 11.

When the hole transport region includes a hole injection layer, the hole injection layer (HIL) may be formed on the first electrode 11 by using various methods such as vacuum deposition, spin coating, casting, and Langmuir-Blodgett (LB) method.

When a hole injection layer is formed by vacuum deposition, for example, the vacuum deposition may be performed at a deposition temperature in a range of about 100 to about 500° C., at a vacuum degree in a range of about $10^{-8}$ to about $10^{-3}$ torr, and at a deposition rate in a range of about 0.01 Å/sec to about 100 Å/sec, though the conditions may vary depending on a compound that is used as a hole injection material and a structure and thermal properties of a desired hole injection layer, but is not limited thereto.

When a hole injection layer is formed by spin coating, the spin coating may be performed at a coating rate in a range of about 2,000 revolutions per minute (rpm) to about 5,000 rpm, and at a temperature in a range of about 80° C. to 200° C. for removing a solvent after the spin coating, though the conditions may vary depending on a compound that is used as a hole injection material and a structure and thermal properties of a desired HIL, but is not limited thereto.

The conditions for forming a hole transport layer and an electron blocking layer may be inferred based on the conditions for forming the hole injection layer.

The hole transport region may include at least one selected from m-MTDATA, TDATA, 2-TNATA, NPB, β—NPB, TPD, a spiro-TPD, a spiro-NPB, a methylated NPB, TAPC, HMTPD, 4,4',4"-tris(N-carbazolyl)triphenylamine (TCTA), polyaniline/dodecylbenzenesulfonic acid (Pani/DBSA), poly(3,4-ethylenedioxythiophene)/poly(4-styrenesulfonate) (PEDOT/PSS), polyaniline/camphor sulfonic acid (Pani/CSA), (polyaniline)/poly(4-styrenesulfonate) (PANI/PSS), a compound represented by Formula 201 below, and a compound represented by Formula 202 below:

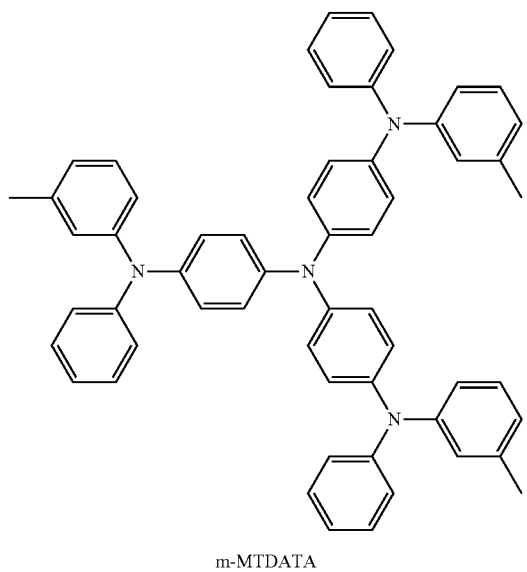

m-MTDATA

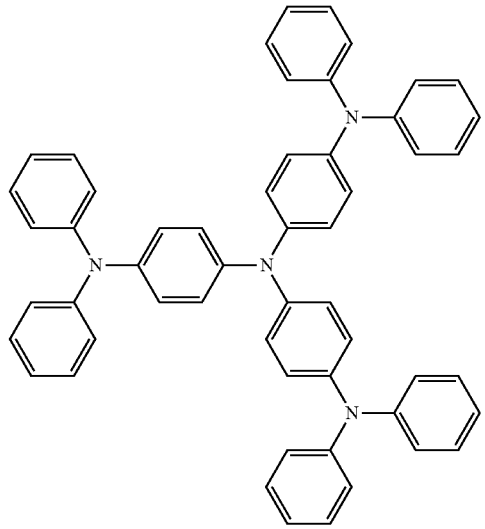

TDATA

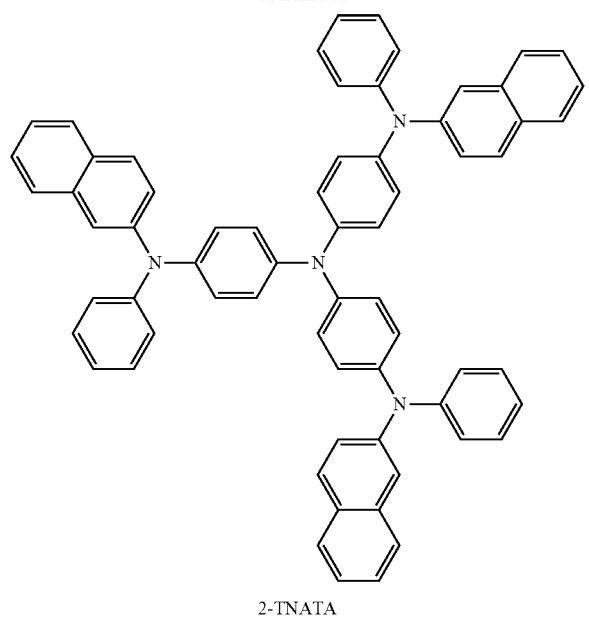
2-TNATA
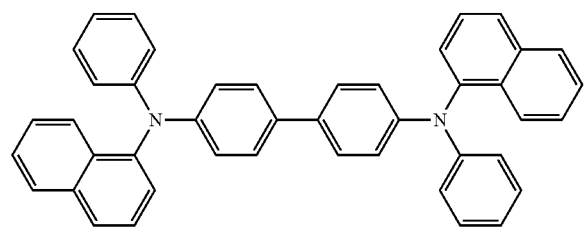
NPB
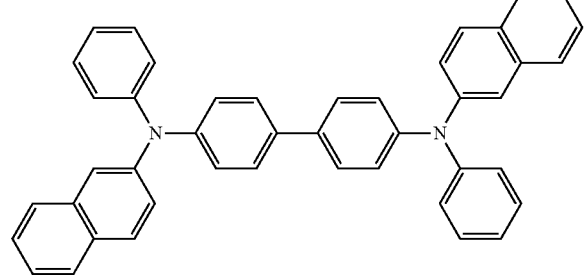
β-NPB
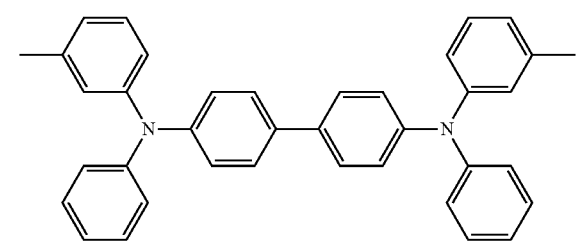
TPD
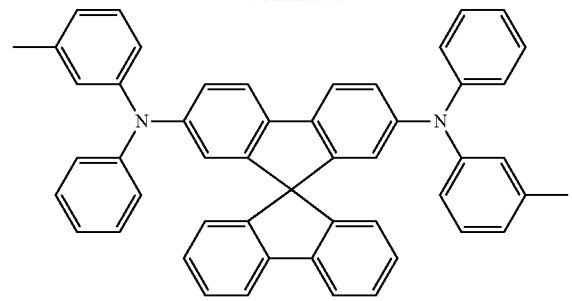
Spiro-TPB
Spiro-NPB
methylated NPB
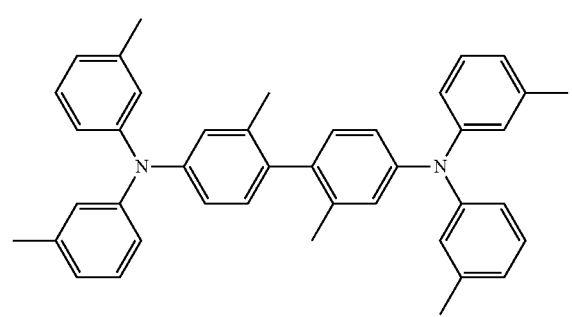
TAPC
HMTPD Formula 201

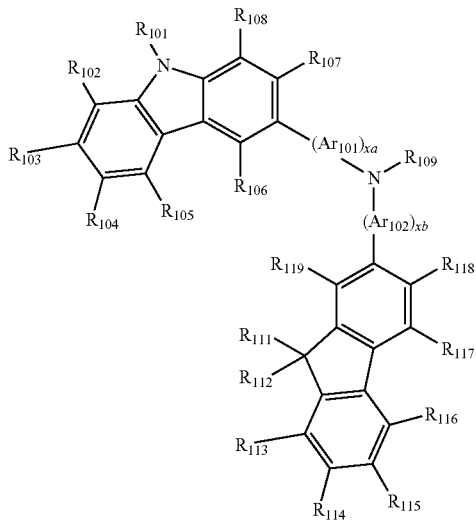

Formula 202

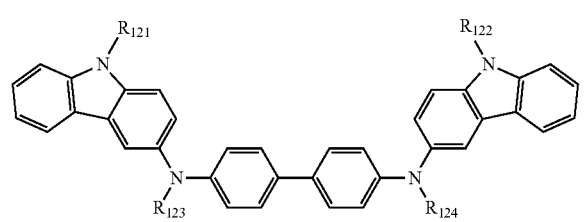

$Ar_{101}$ and $Ar_{102}$ in Formula 201 may be each independently selected from a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group and a pentacenylene group; and a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, and a pentacenylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_1$-$C_{10}$ heterocycloalkyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group.

In Formula 201, xa and xb may be each independently an integer of 0 to 5, or 0, 1, or 2. In some embodiments, xa may be 1 and xb may be 0, but they are not limited thereto.

In Formulae 201 and 202, $R_{101}$ to $R_{108}$, $R_{111}$ to $R_{119}$ and $R_{121}$ to $R_{124}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group (for example, a methyl group, an ethyl group, a propyl group, a butyl group, a pentyl group, or a hexyl group), and a $C_1$-$C_{10}$ alkoxy group (for example, a methoxy group, an ethoxy group, a propoxy group, a butoxy group, or a pentoxy group);

a $C_1$-$C_{10}$ alkyl group and a $C_1$-$C_{10}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof;

a phenyl group, a naphthyl group, an anthracenyl group, a fluorenyl group, and a pyrenyl group; and a phenyl group, a naphthyl group, an anthracenyl group, a fluorenyl group, and a pyrenyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, and a $C_1$-$C_{10}$ alkoxy group, but they are not limited thereto.

In Formula 201, $R_{109}$ may be selected from a phenyl group, a naphthyl group, an anthracenyl group, and a pyridinyl group; and a phenyl group, a naphthyl group, an anthracenyl group, and a pyridinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group.

According to an embodiment, the compound represented by Formula 201 may be represented by Formula 201A, but it is not limited thereto:

Formula 201A

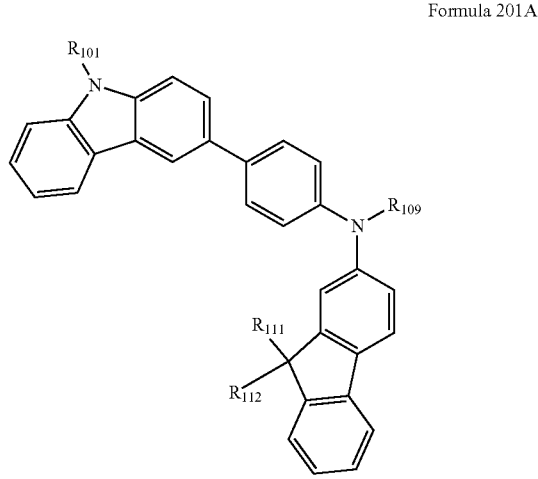

Descriptions of $R_{101}$, $R_{111}$, $R_{112}$, and $R_{109}$ in Formula 201A are the same as described above.
For example, the compound represented by Formula 201 and the compound represented by Formula 202 may include Compounds HT1 to HT20, but they are not limited thereto:
HT1
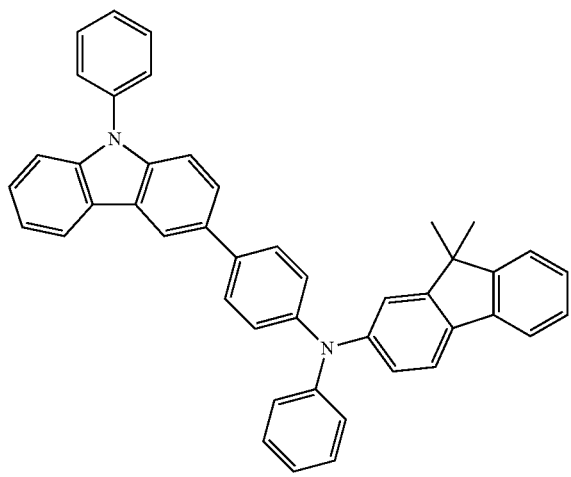
HT2
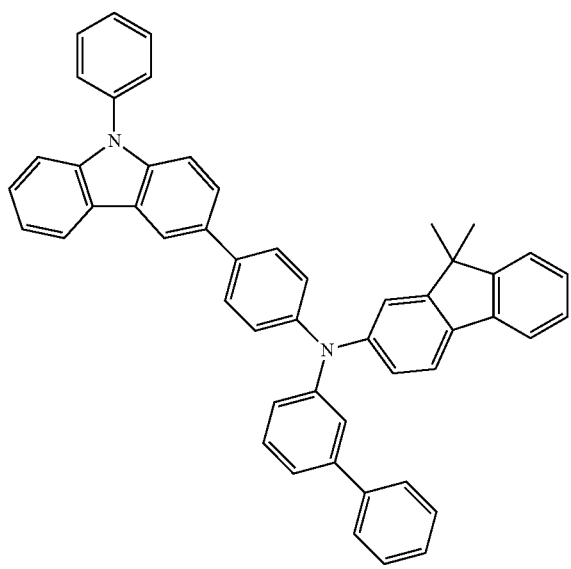
HT3
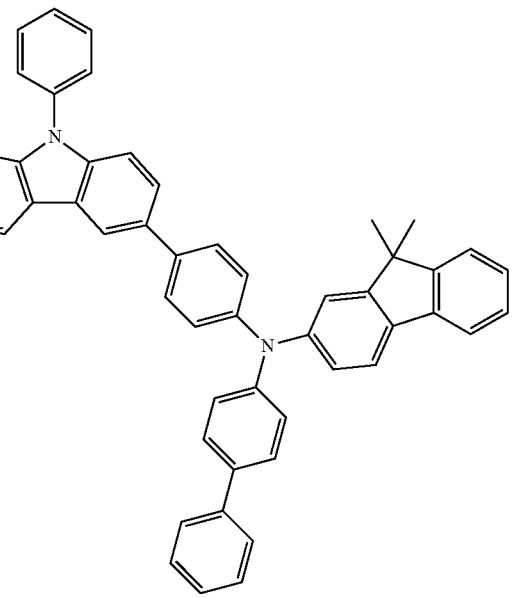
HT4
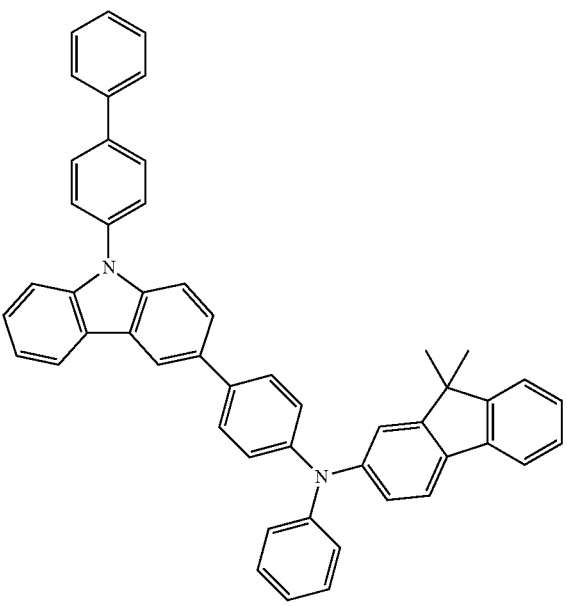

HT5
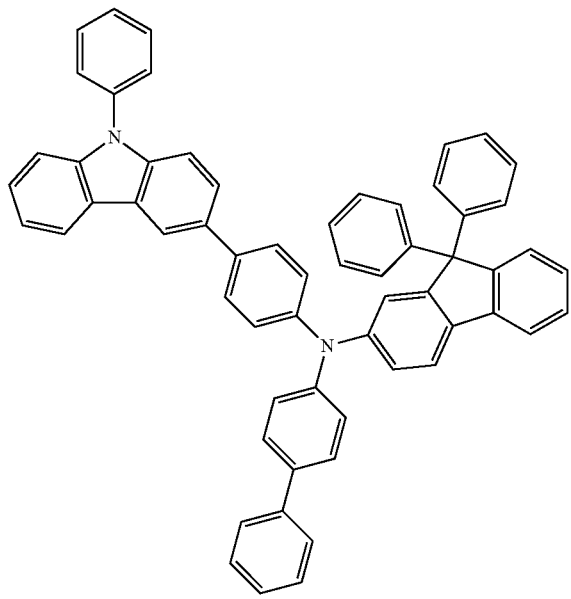
HT6
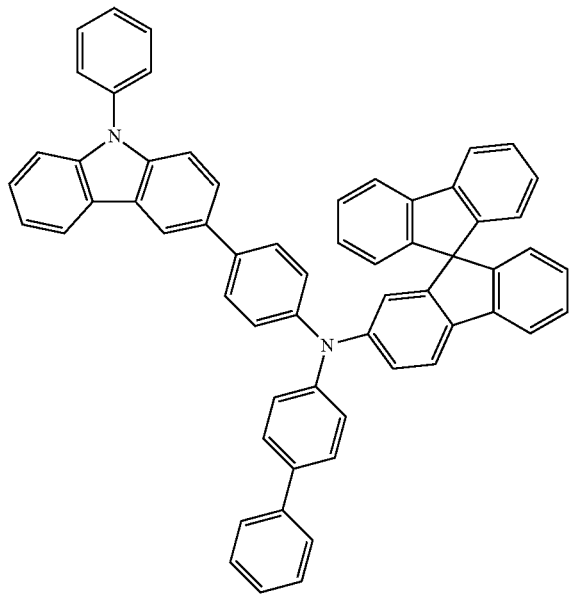
HT7
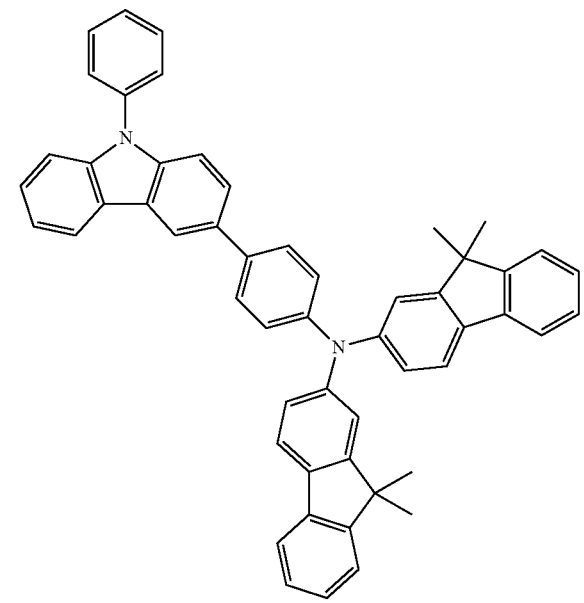
HT8
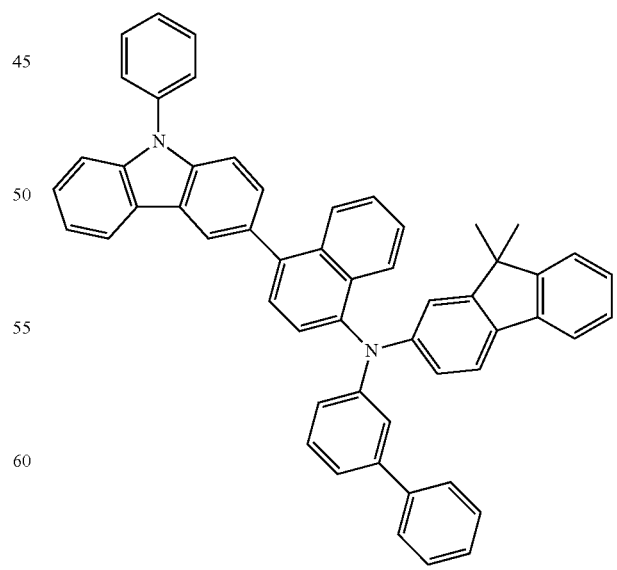

HT9
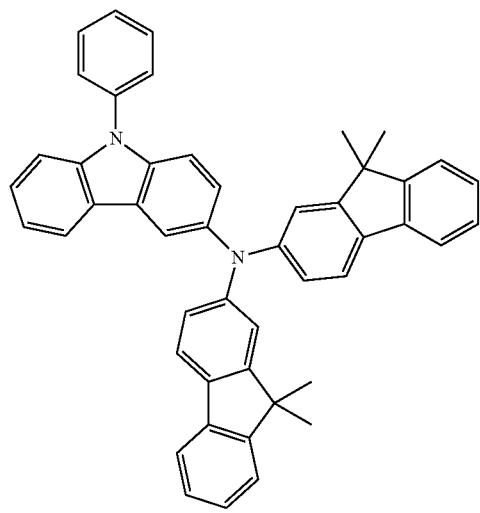
HT10
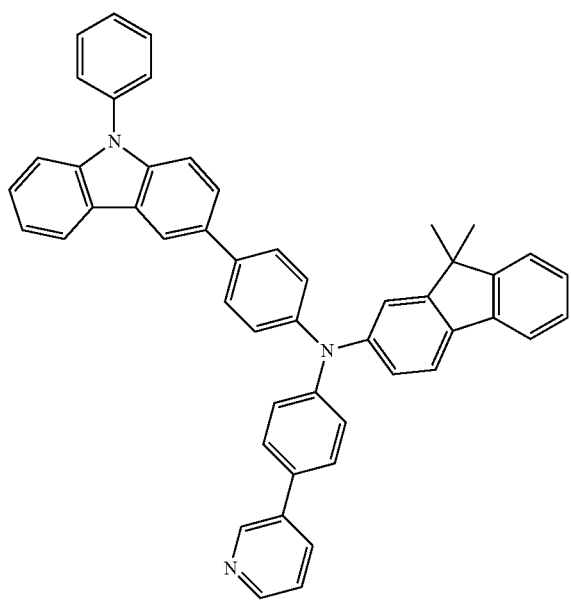
HT11
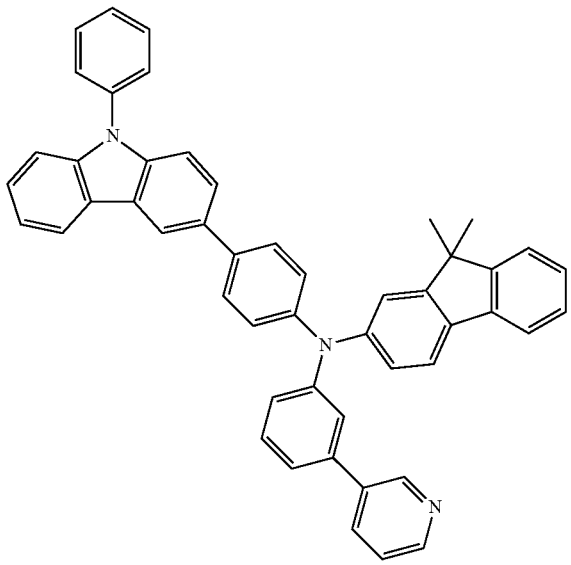
HT12
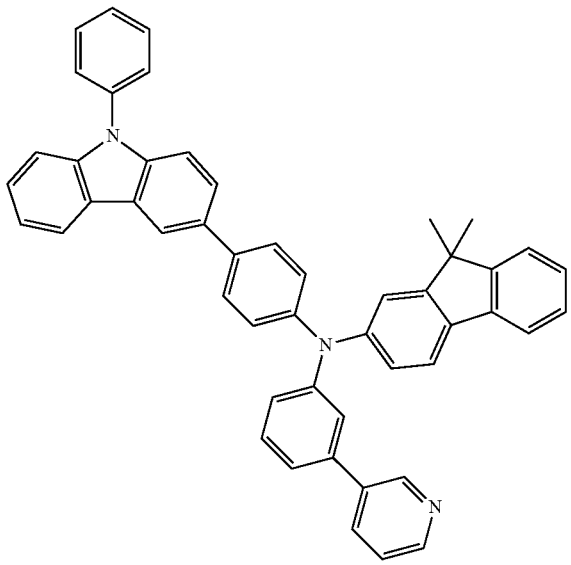
HT13
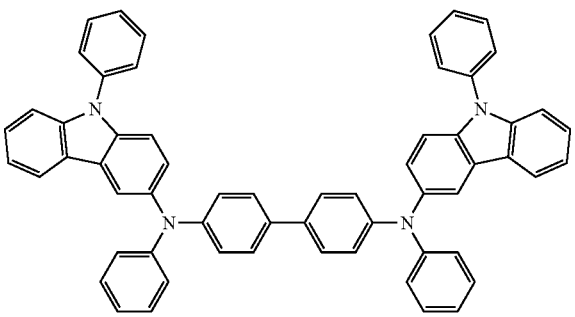

HT14
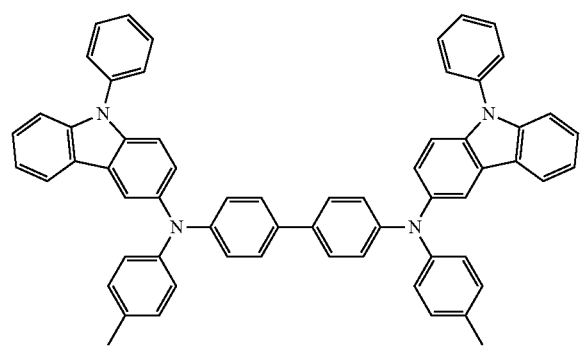

HT15
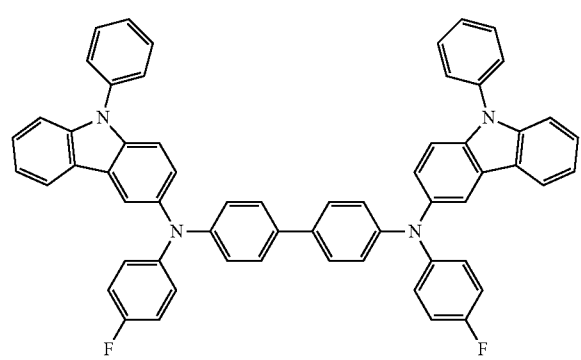

HT16
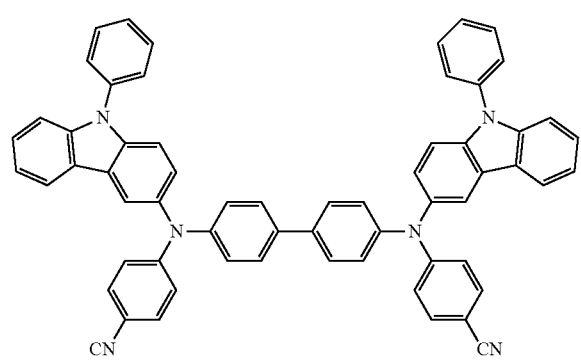

HT17
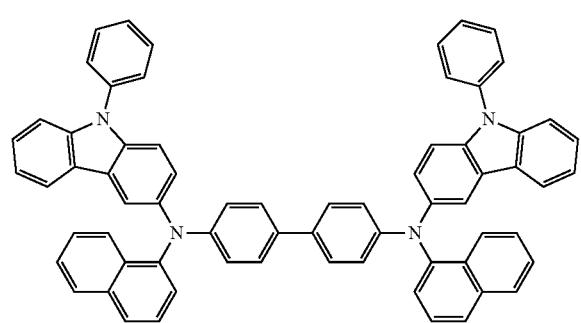

HT18
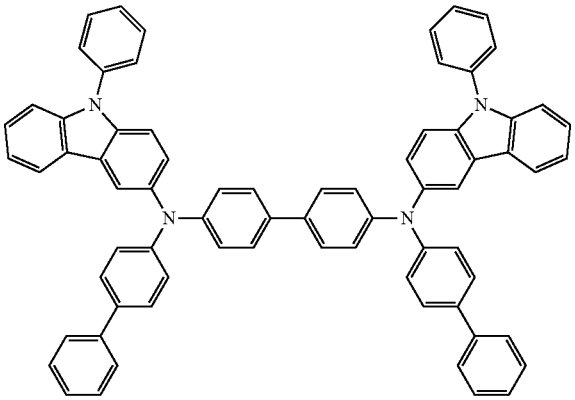

HT19
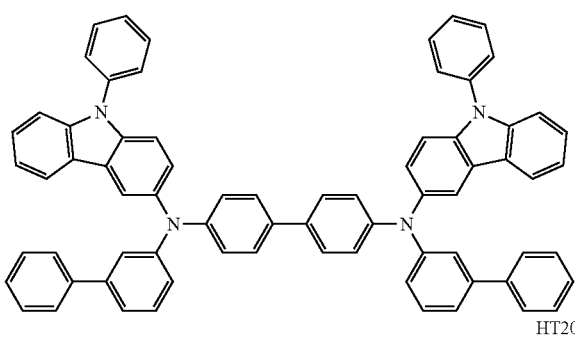

HT20
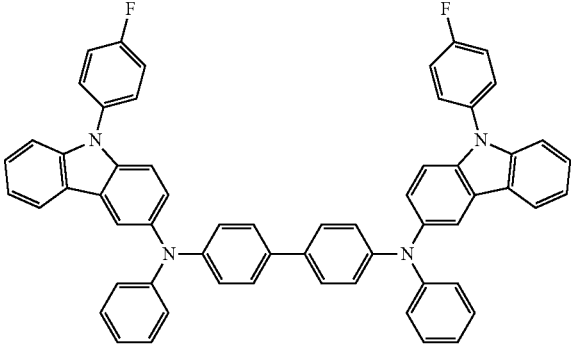

A thickness of the hole transport region may be in a range of about 100 Angstroms (Å) to about 10,000 Å, for example, about 100 Å to about 1,000 Å. When the hole transport region includes the a hole injection layer and a hole transport layer, a thickness of the hole injection layer may be in a range of about 100 Å to about 10,000 Å, for example, about 100 Å to about 1,000 Å, a thickness of the hole transport layer may be in a range of about 50 Å to about 2,000 Å, for example, about 100 Å to about 1,500 Å. When the thicknesses of the hole transport region, the hole injection layer, and the hole transport layer are within these ranges, excellent hole transport characteristics may be obtained without a substantial increase in driving voltage.

The hole transport region may further include, in addition to the mentioned materials above, a charge-generating material to improve conductive properties. The charge-generating material may be homogeneously or non-homogeneously dispersed throughout the hole transport region.

The charge-generating material may be, for example, a p-dopant. The p-dopant may be one selected from a quinone derivative, a metal oxide, and a cyano group-containing compound, but is not limited thereto. For example, non-limiting examples of the p-dopant are a quinone derivative, such as tetracyanoquinonedimethane (TCNQ) or 2,3,5,6-tetrafluoro-tetracyano-1,4-benzoquinonedimethane (F4-TCNQ); a metal oxide, such as a tungsten oxide or a molybdenum oxide; and a compound containing a cyano group, such as Compound HT-D1 illustrated below, but they are not limited thereto.

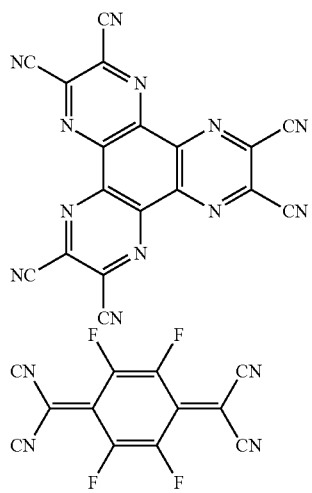

F4-TCNQ

The hole transport region may further include a buffer layer.

The buffer layer may compensate for an optical resonance distance according to a wavelength of light emitted from the emission layer to improve the efficiency of an organic light-emitting device.

An emission layer (EML) may be formed on the hole transport region by using various methods, such as vacuum deposition, spin coating, casting, or an LB method. When the emission layer is formed by vacuum deposition or spin coating, deposition and coating conditions for the emission layer may be generally similar to the conditions for forming a hole injection layer, though the conditions may vary depending on the compound used.

When the organic light-emitting device is a full color organic light-emitting device, the emission layer may be patterned into a red emission layer, a green emission layer, and a blue emission layer. Alternatively, the emission layer may have a structure in which the red emission layer, the green emission layer, and/or the blue emission layer are layered to emit white light or other various embodiments are possible.

The emission layer may include the carbazole compound represented by Formula 1. The emission layer may further include a dopant. The dopant may include at least one selected from a fluorescent dopant and a phosphorescent dopant.

The emission layer may include a host and a dopant, and the host may include at least one selected from the carbazole compounds represented by Formula 1.

In some embodiments, the emission layer may include a first host and a second host, the first host and the second host may be different from each other, and the first host and the second host may be each independently selected from the carbazole compound represented by Formula 1.

As described above, the emission layer may include the first host and the second host, so that balance of a hole and electron transportation into the emission layer may be achieved, thereby improving efficiency, luminance, and lifespan of the organic light-emitting device.

In some embodiments, the emission layer may include Host 1 and Host 2,

Host 1 and Host 2 may be different from each other, and
Host 1 may be selected from the carbazole compounds represented by Formula 1;
Host 2 may be selected from the first compound represented by Formula 4 and the second compound represented by Formula 5:

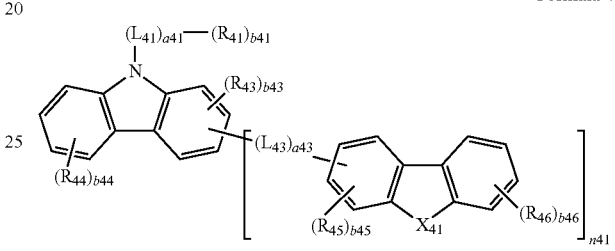

Formula 4

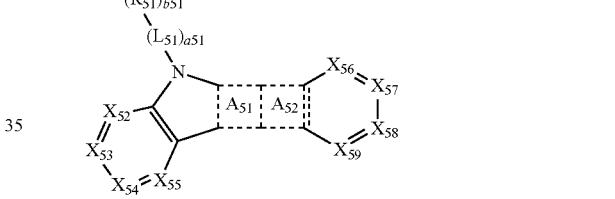

Formula 5

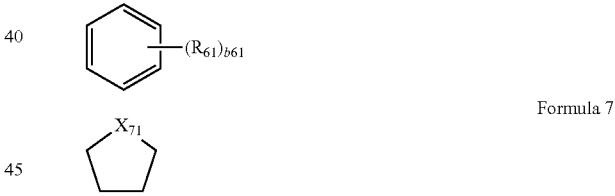

Formula 6

Formula 7 wherein in Formulae 4 to 7, $X_{41}$ may be selected from N-[$(L_{42})_{a42}$-$(R_{42})_{b42}$], S, O, S(=O), S(=O)$_2$, C(=O), C($R_{47}$)($R_{48}$), Si($R_{47}$)($R_{48}$), P($R_{43}$), P(=O)($R_{47}$), and C=N($R_{47}$);

ring $A_{51}$ in Formula 5 may be represented by Formula 6;
ring $A_{52}$ in Formula 5 may be represented by Formula 7;
$X_{71}$ may be selected from N-[$(L_{71})_{a71}$-$(R_{71})_{b71}$], S, O, S(=O), S(=O)$_2$, C(=O), C($R_{72}$)($R_{73}$), Si($R_{72}$)($R_{73}$), P($R_{71}$), P(=O)($R_{71}$), and C=N($R_{71}$);

$X_{52}$ may be C($R_{52}$) or nitrogen (N) atom, $X_{53}$ may be C($R_{53}$) or N, $X_{54}$ may be C($R_{54}$) or N, $X_{55}$ may be C($R_{55}$) or N, $X_{56}$ may be C($R_{56}$) or N, $X_{57}$ may be C($R_{57}$) or N, $X_{58}$ may be C($R_{58}$) or N, and $X_{59}$ may be C($R_{59}$) or N;

$L_{41}$ to $L_{43}$, $L_{51}$, and $L_{71}$ may be each independently selected from a substituted or unsubstituted $C_3$-$C_{10}$ cycloalkylene group, a substituted or unsubstituted $C_1$-$C_{10}$ heterocycloalkylene group, a substituted or unsubstituted $C_1$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group;

n41, a41 to a43, a51, and a71 may be each independently selected from 0, 1, 2, and 3;

$R_{41}$ to $R_{48}$, $R_{51}$ to $R_{59}$, $R_{61}$, and $R_{71}$ to $R_{73}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —N($Q_1$)($Q_2$), —Si($Q_3$)($Q_4$)($Q_5$), and —B($Q_6$)($Q_7$);

b41 to b46, b51, and b71 may be each independently an integer selected from 1 to 3;

at least one substituent of the substituted $C_1$-$C_{60}$ alkylene group, substituted $C_2$-$C_{60}$ alkenylene group, substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, substituted divalent non-aromatic condensed polycyclic group, substituted divalent non-aromatic condensed heteropolycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group may be selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), and —B($Q_{16}$)($Q_{17}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_1$-$C_{60}$ alkenyl group, a $C_1$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), and —B($Q_{26}$)($Q_{27}$); and —N($Q_{31}$)($Q_{32}$), —Si($Q_{33}$)($Q_{34}$)($Q_{35}$), and —B($Q_{36}$)($Q_{37}$);

wherein $Q_1$ to $Q_7$, $Q_{11}$ to $Q_{17}$, $Q_{21}$ to $Q_{27}$, and $Q_{31}$ to $Q_{37}$ may be each independently selected from a hydrogen, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

In some embodiments, in Formula 4 and 5, at least one of $R_{41}$, $R_{42}$, and $R_{43}$ and at least one of $R_{51}$ and $R_{71}$ may be each independently selected from a thiophenyl group, a furanyl group, a carbazolyl group, an acridinyl group, a dibenzofuranyl group, a dibenzothiophenyl group, a benzocarbazolyl group, a dibenzocarbazolyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, and an ovalenyl group; and a thiophenyl group, a furanyl group, a carbazolyl group, an acridinyl group, a dibenzofuranyl group, a dibenzothiophenyl group, a benzocarbazolyl group, a dibenzocarbazolyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, and an ovalenyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a phenyl group-substituted with a $C_1$-$C_{20}$ alkyl group, a phenyl group-substituted with a phenyl group, a naphthyl group, a phenalenyl group, a phenanthrenyl group, an anthracenyl group, a triphenylenyl group, a pyrenyl group, a chrysenyl group, a pyridinyl group, a pyrazinyl group, a pyrimidinyl group, a pyridazinyl group, a naphthyridinyl group, a quinoxalinyl group, a quinazolinyl group, and —Si($Q_{33}$)($Q_{34}$)($Q_{35}$);

wherein $Q_{33}$ to $Q_{35}$ may be each independently selected from a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, and a quinoxalinyl group, but they are not limited thereto.

In some embodiments, the first compound may be selected from a group represented by one of Formulae 4-1 to 4-12, and the second compound may be selected from a group represented by one of Formulae 5-1 to 5-6:

4-1

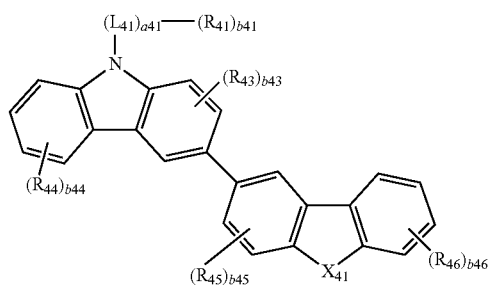

-continued 4-3

4-4

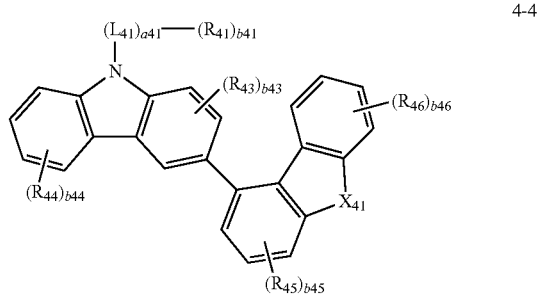

4-5

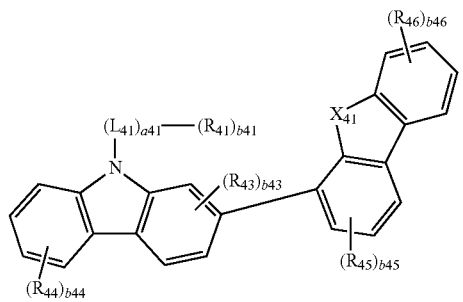

4-2

4-6

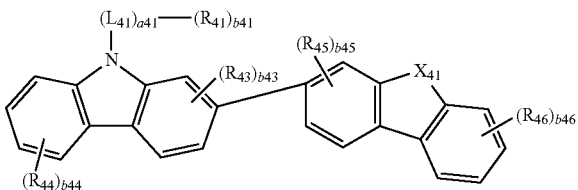

4-7

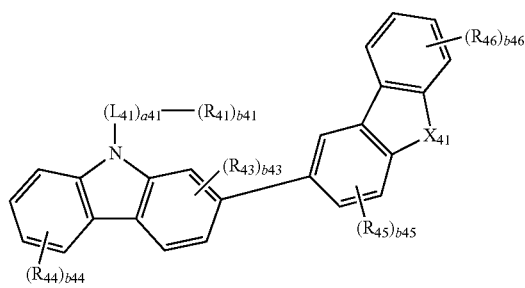

4-8
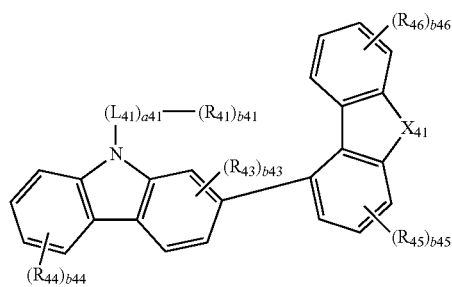
4-9
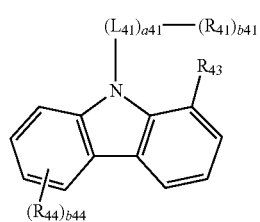
4-10
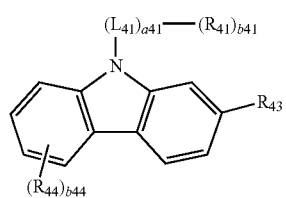
4-11
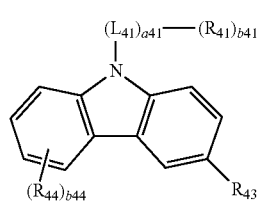
4-12
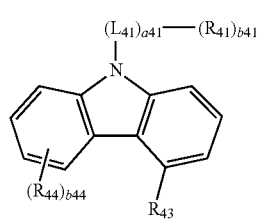
5-1
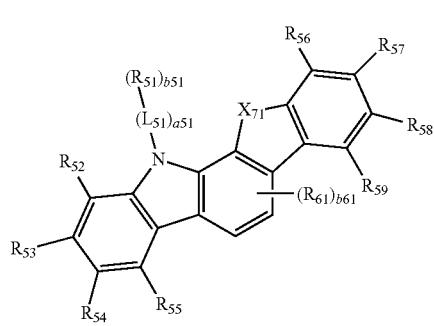
5-2
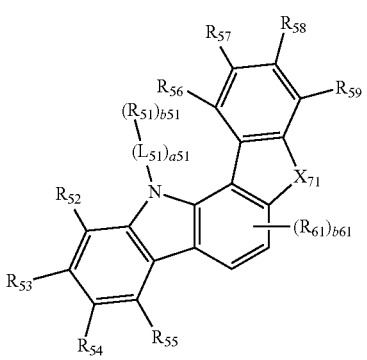
5-3
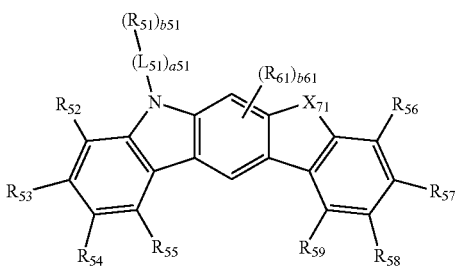
5-4
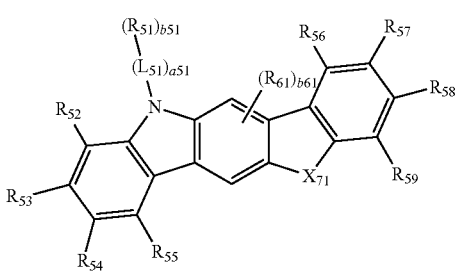
5-5
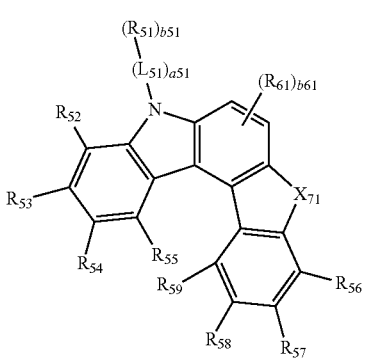
5-6
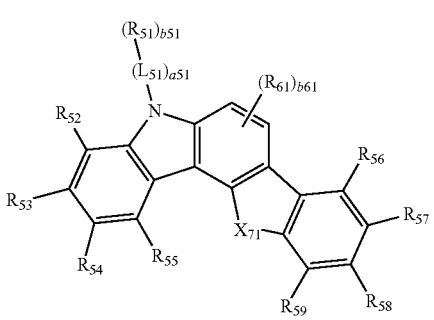
wherein in Formulae 4-1 to 4-12 and 5-1 to 5-6, $X_{41}$, $L_{41}$, a41, $R_{41}$, $R_{43}$ to $R_{46}$, b41, b43 to b46, $X_{71}$, $L_{51}$, a51, $R_{51}$ to $R_{59}$, $R_{61}$, and b61 may be understood by referring to the descriptions above.

In some embodiments, the first compound represented by Formula 4 may include at least one selected from Compounds A1 to A83, and the second compound represented by Formula 5 may include at least one selected from Compounds B1 to B20, but they are not limited thereto:

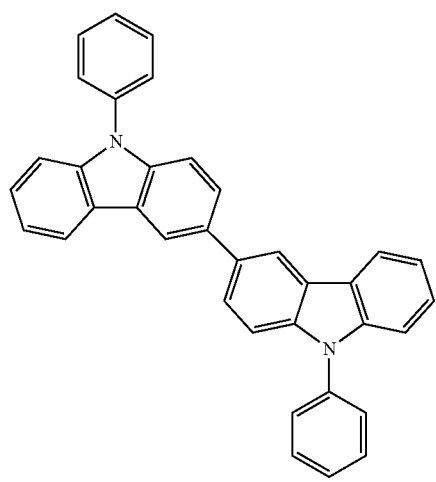

A1

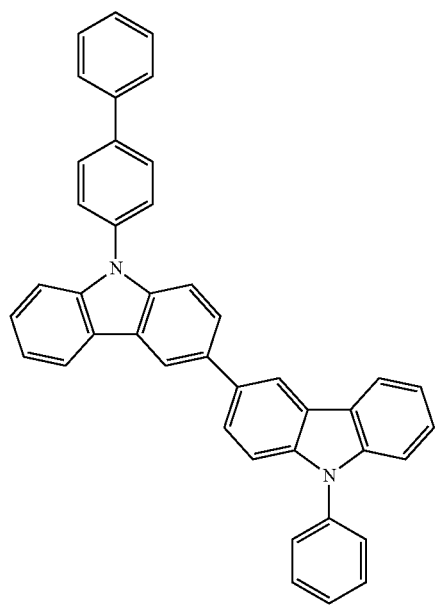

A2

-continued

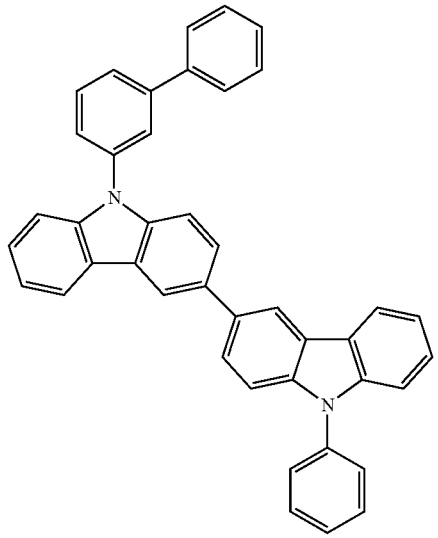

A3

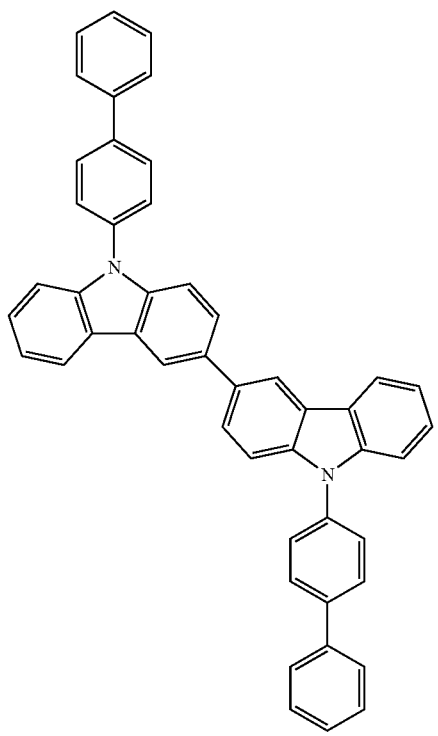

A4

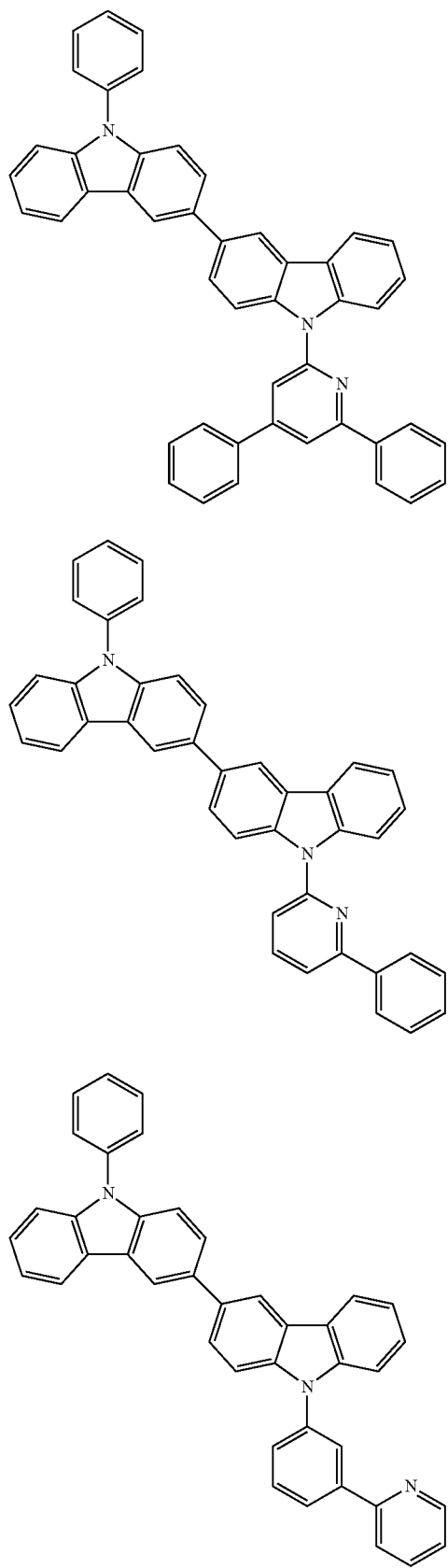
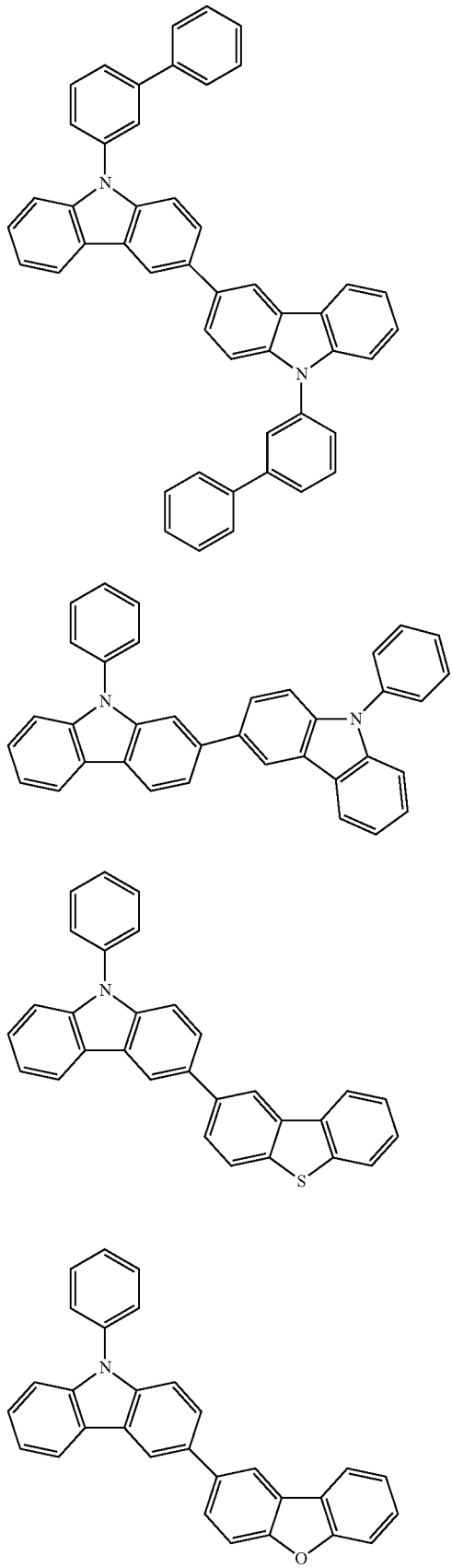

A12
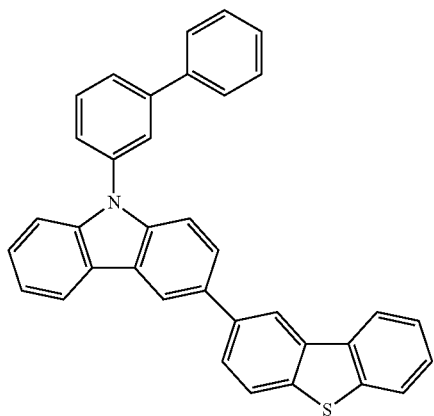
A13
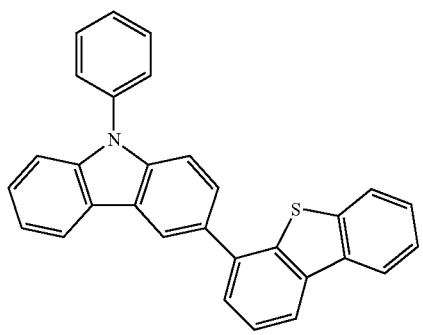
A14
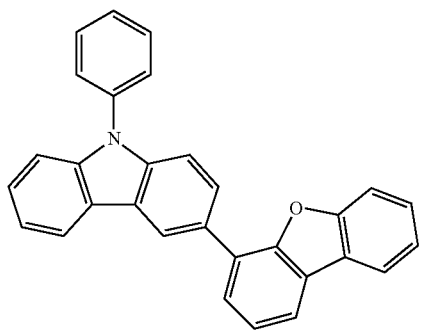
A15
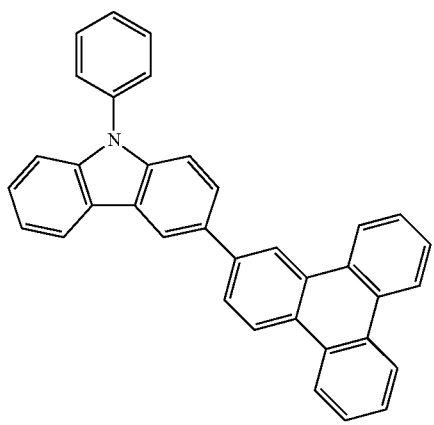
A16
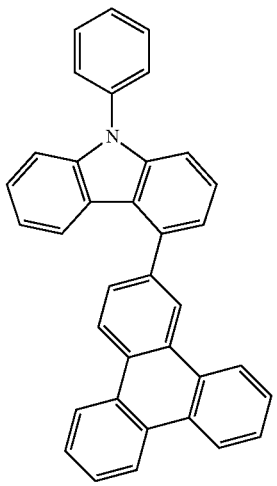
A17
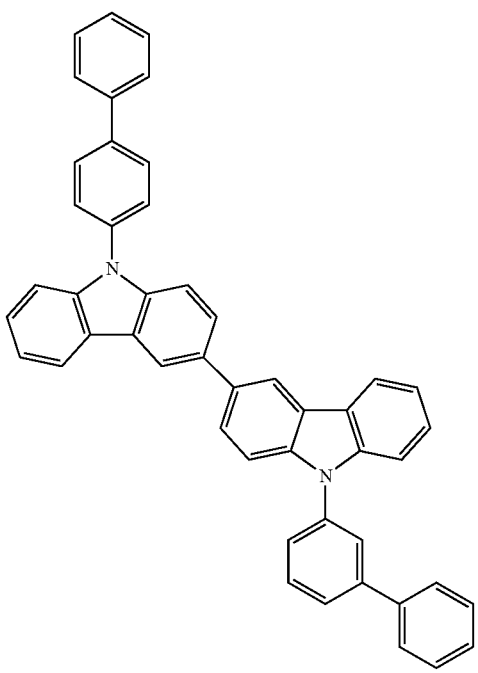
A18
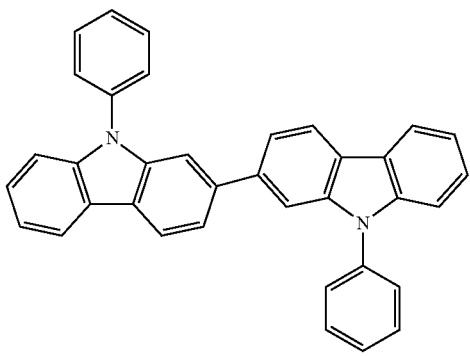

A19
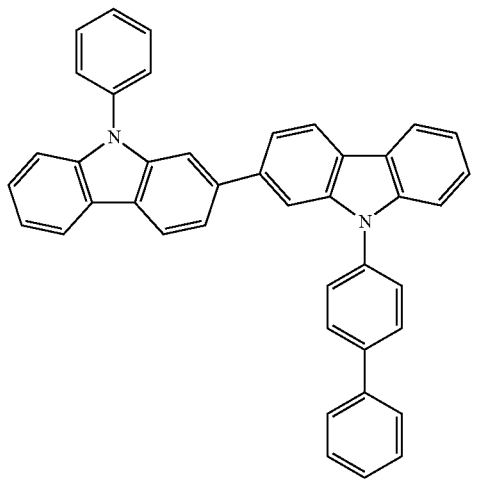
A20
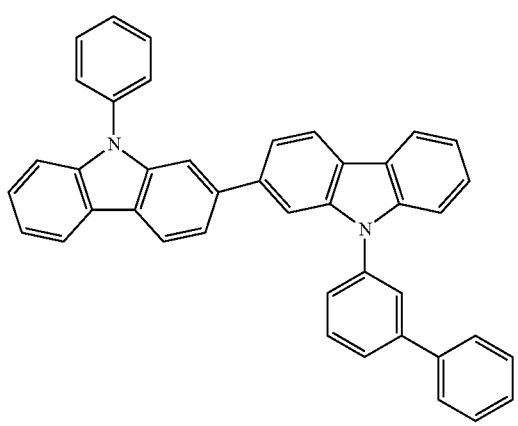
A21
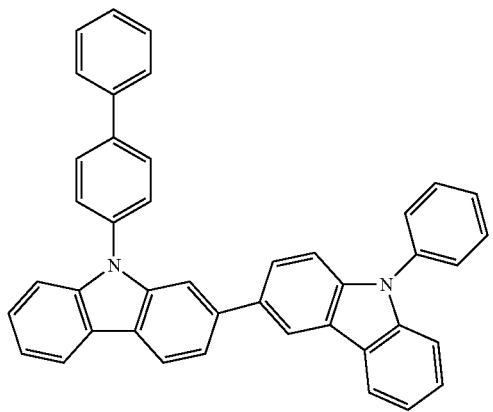
A22
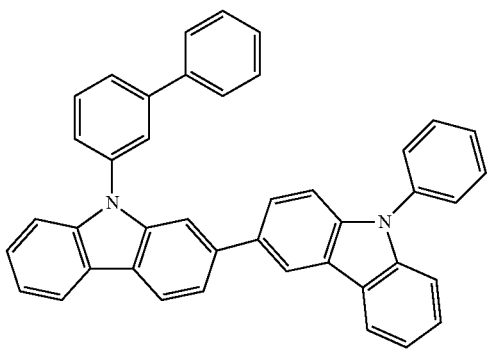
A23
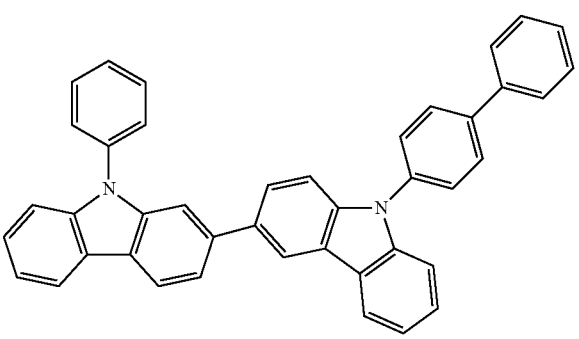
A24
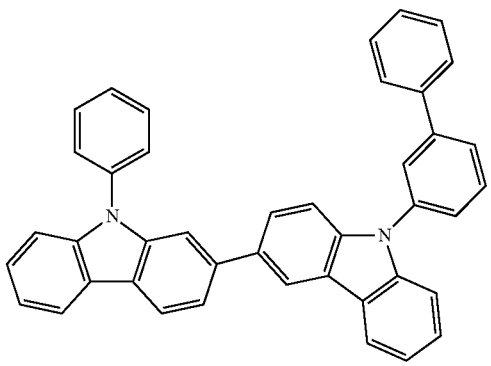
A25
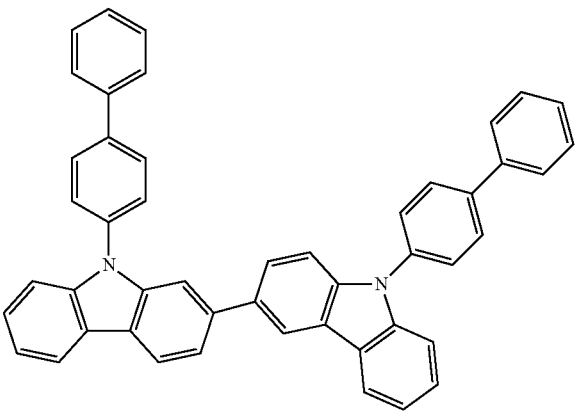

A26
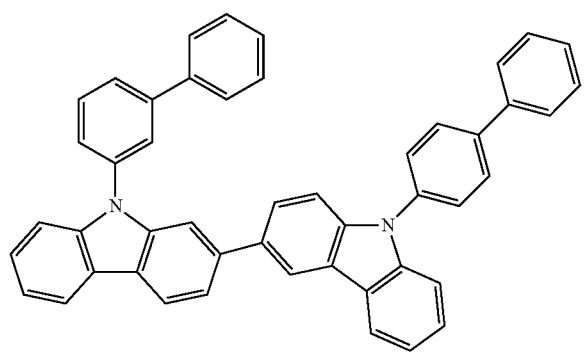
A29
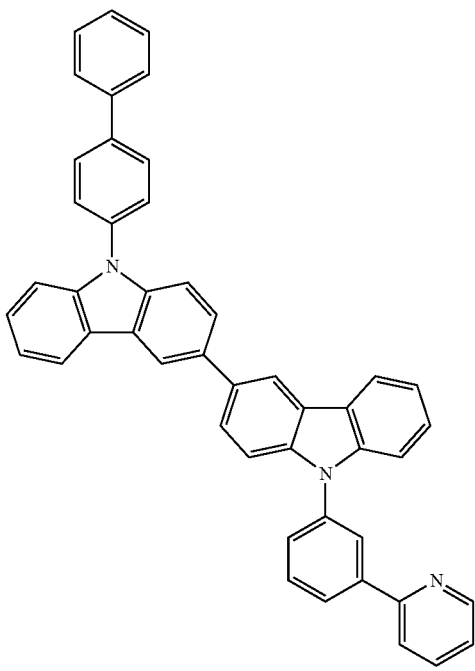
A27
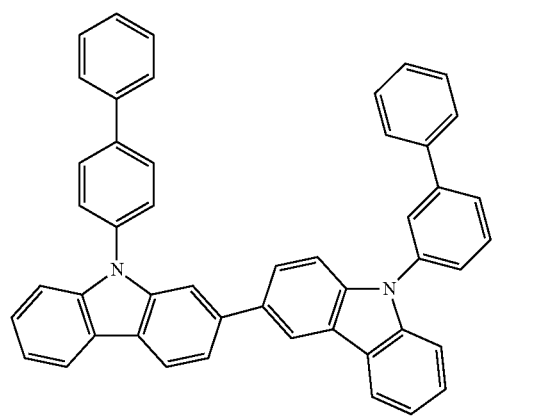
A28
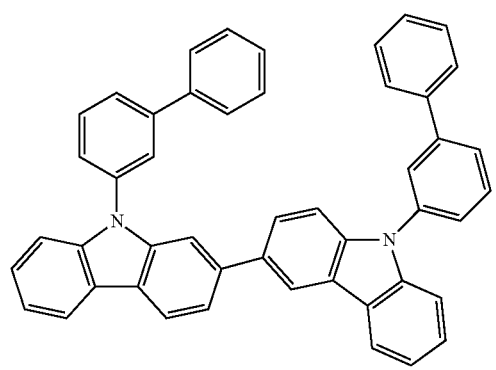
A30
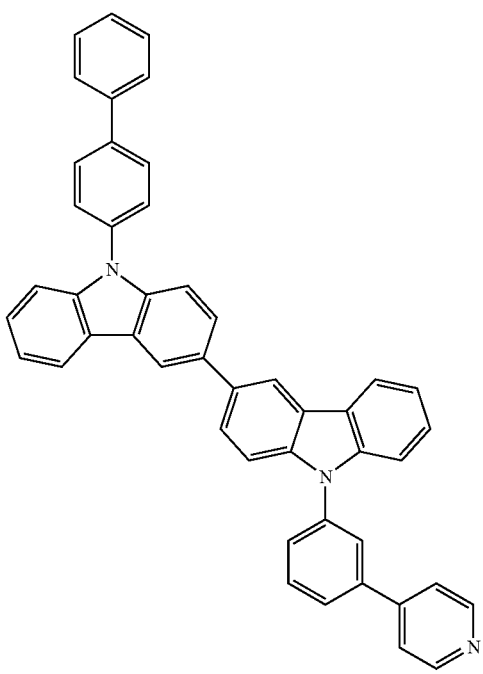

A31
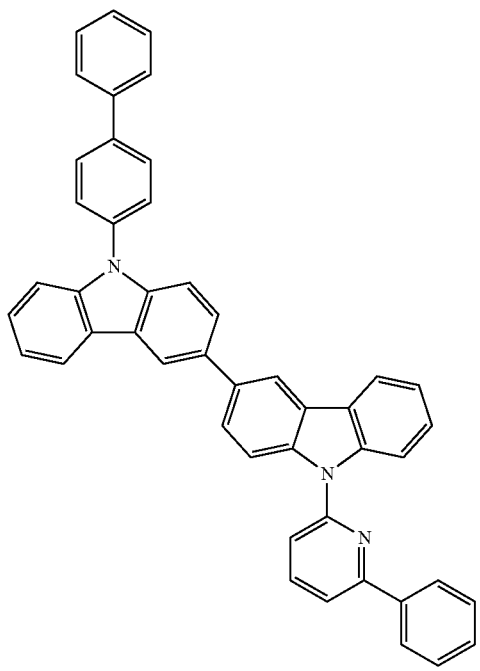
A32
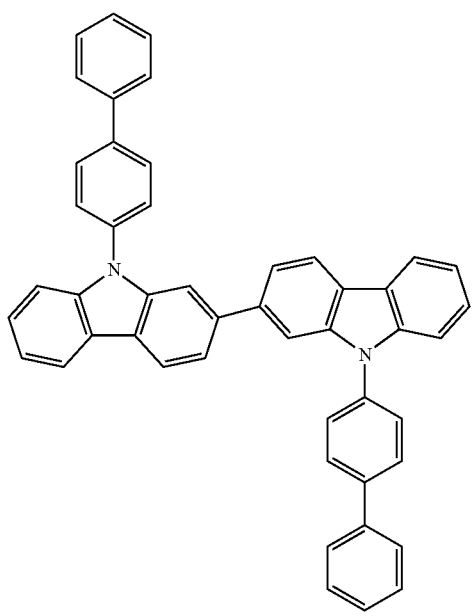
A33
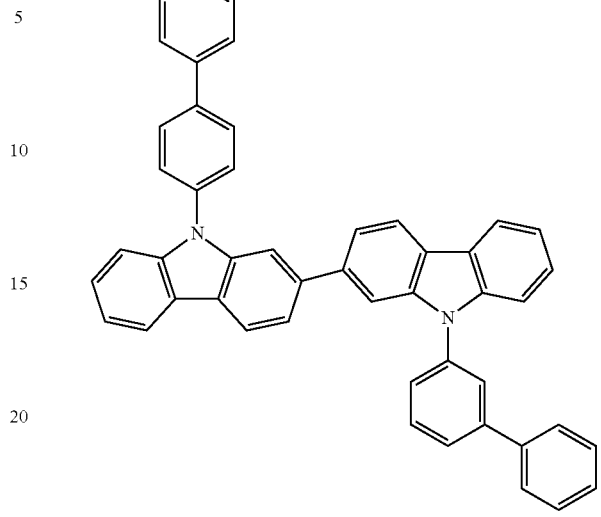
A34
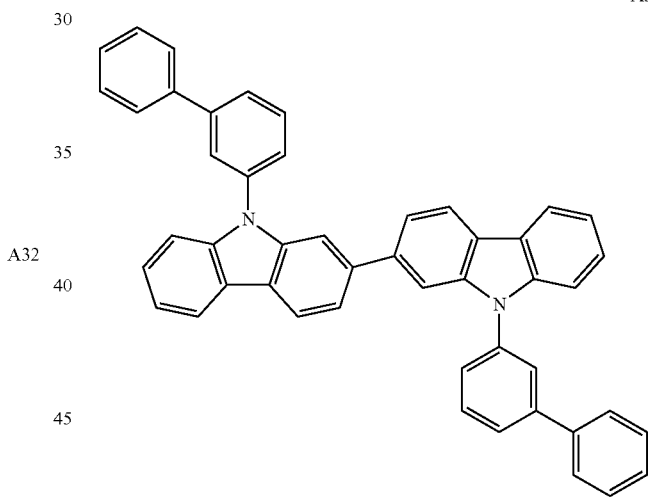
A35
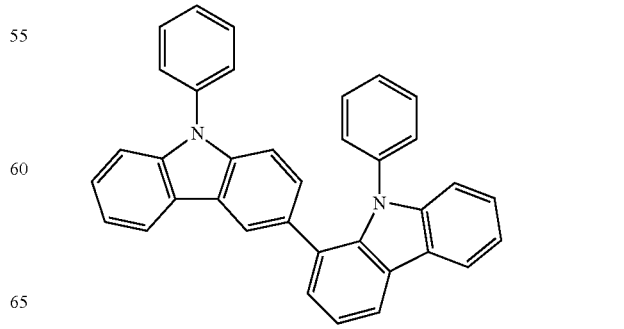

A36
A37
A38
A39
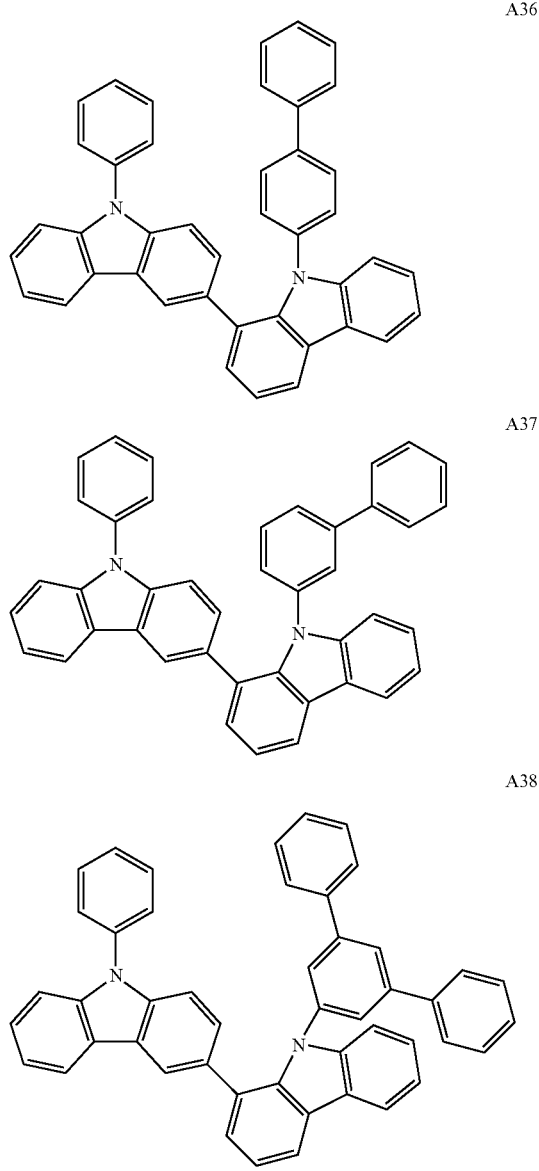
A40
A41
A42
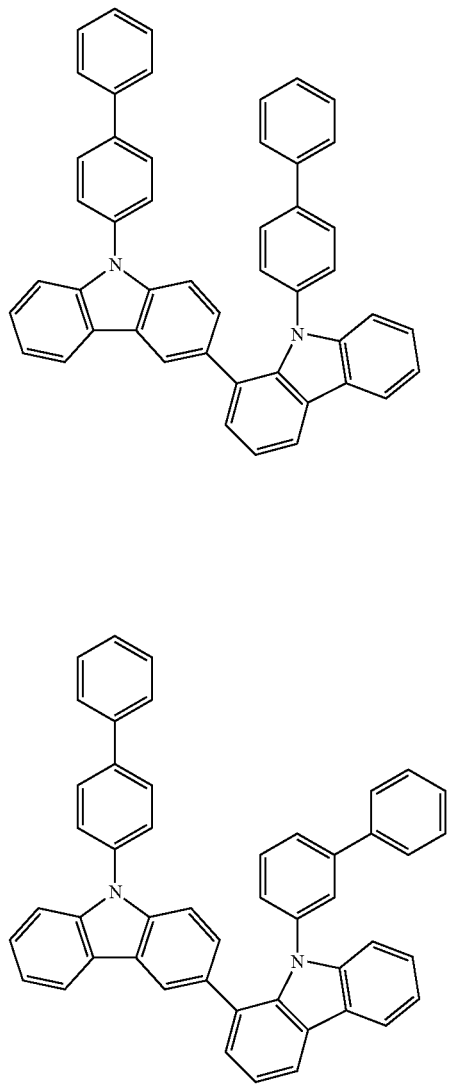

-continued
A43
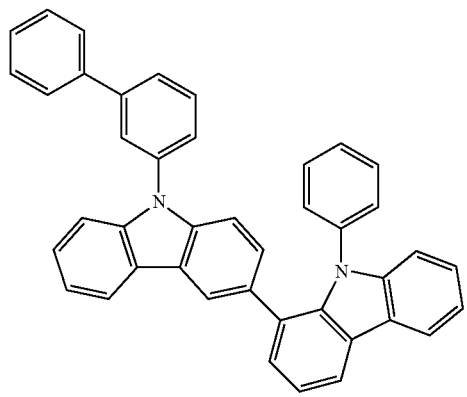
A44
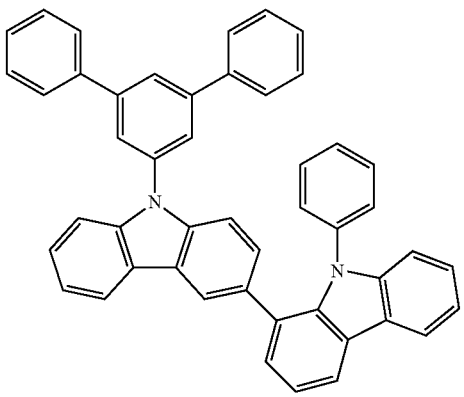
A45
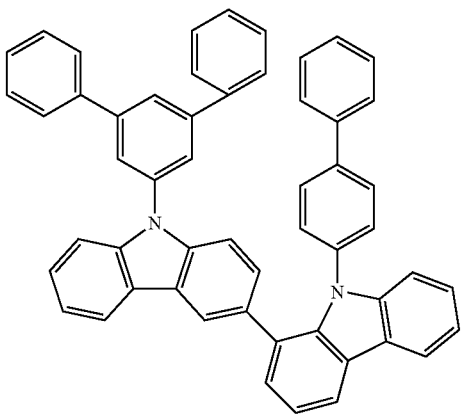
A46
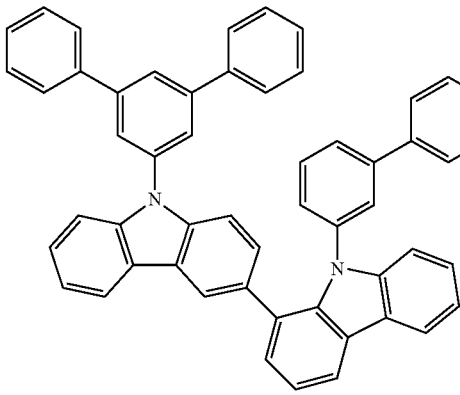
A47
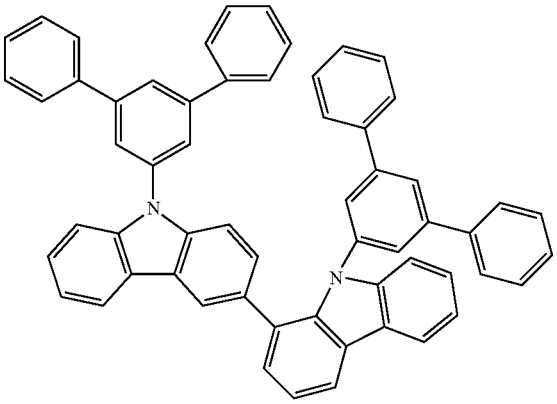
A48
A49
A50

-continued
A51
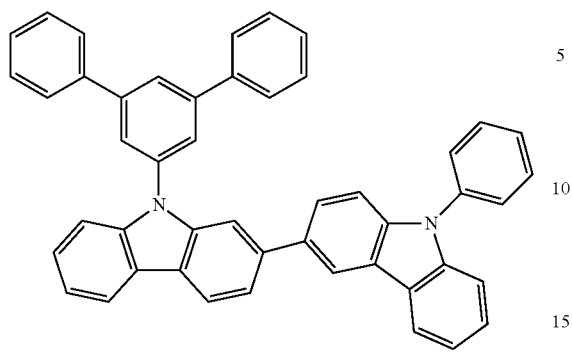
A52
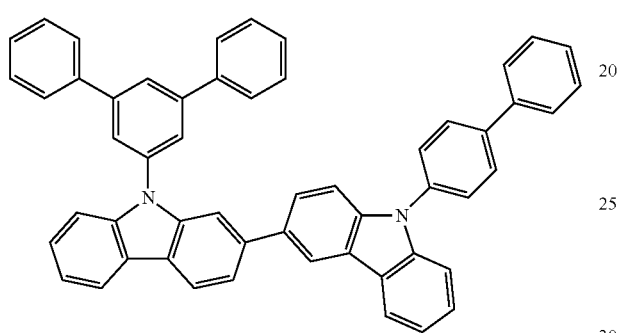
A53
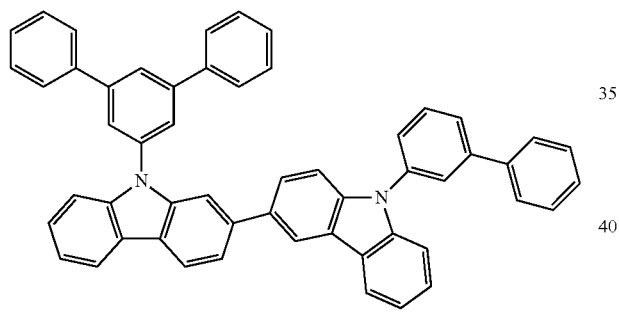
A54
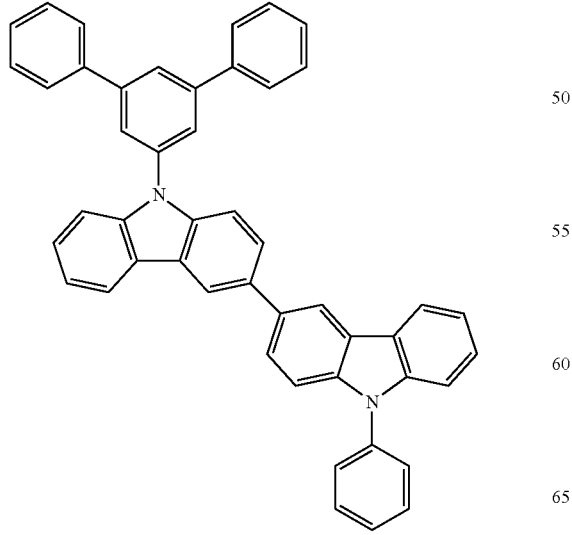
-continued
A55
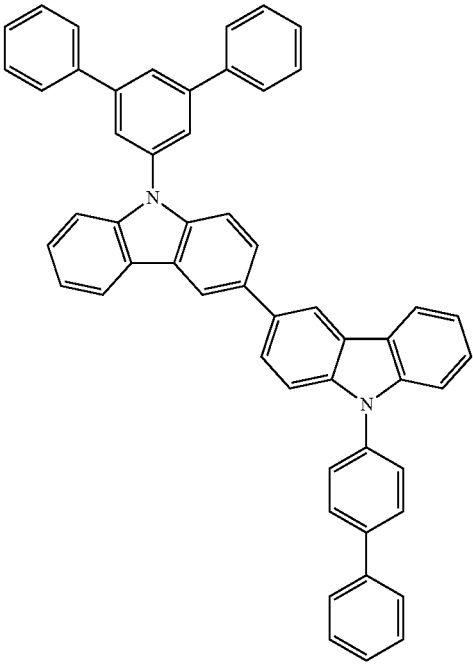
A56
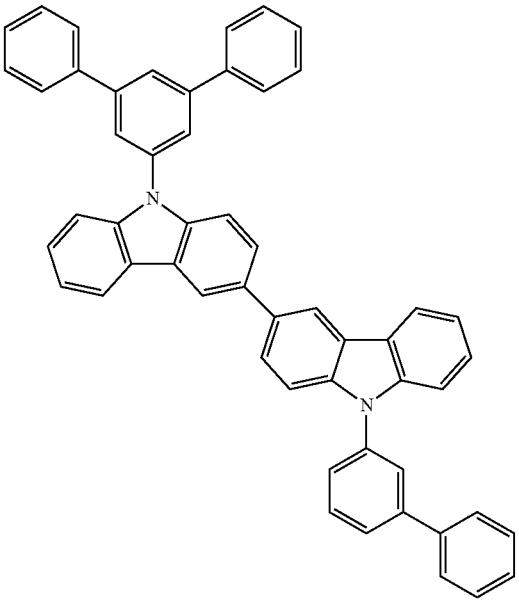

A57
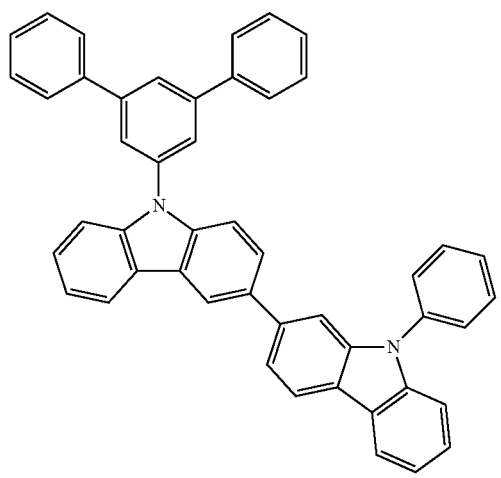
A58
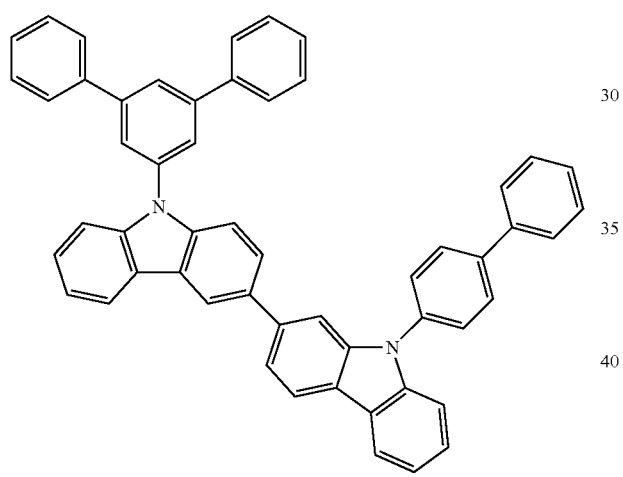
A59
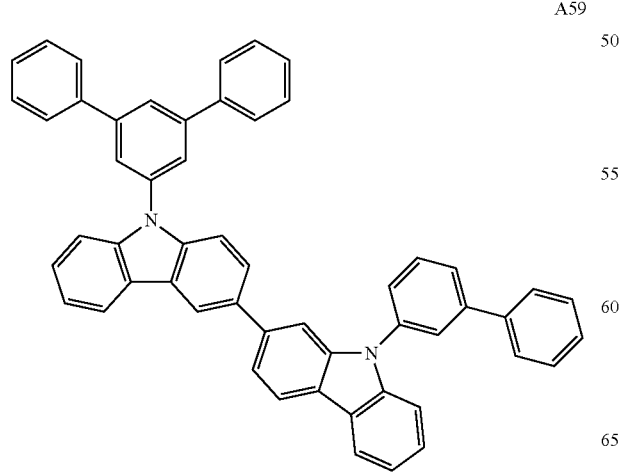
A60
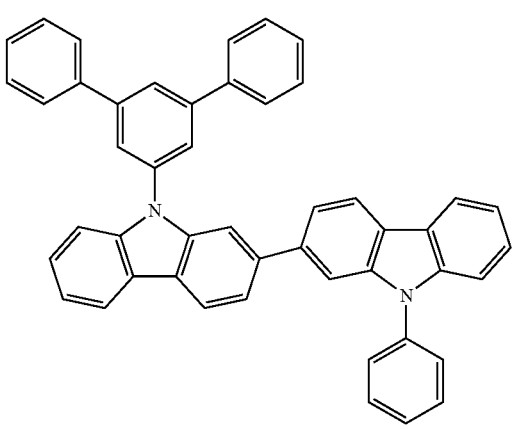
A61
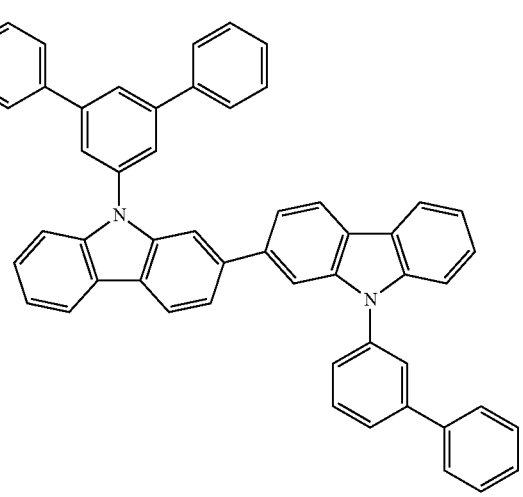
A62

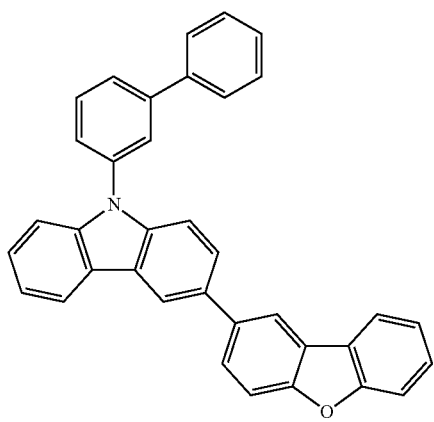
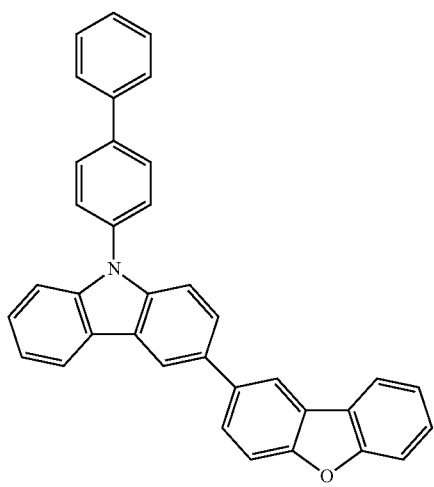
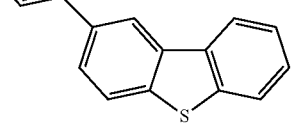
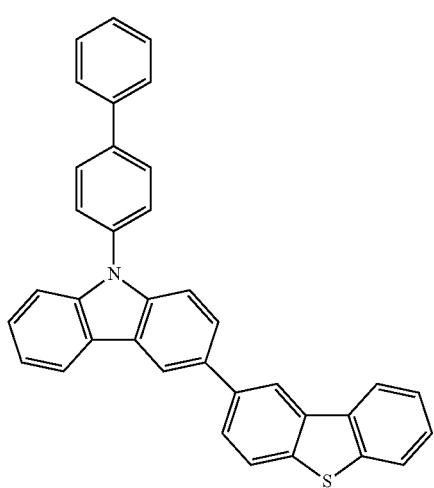
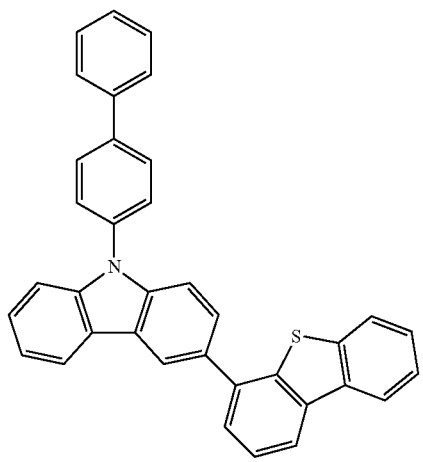

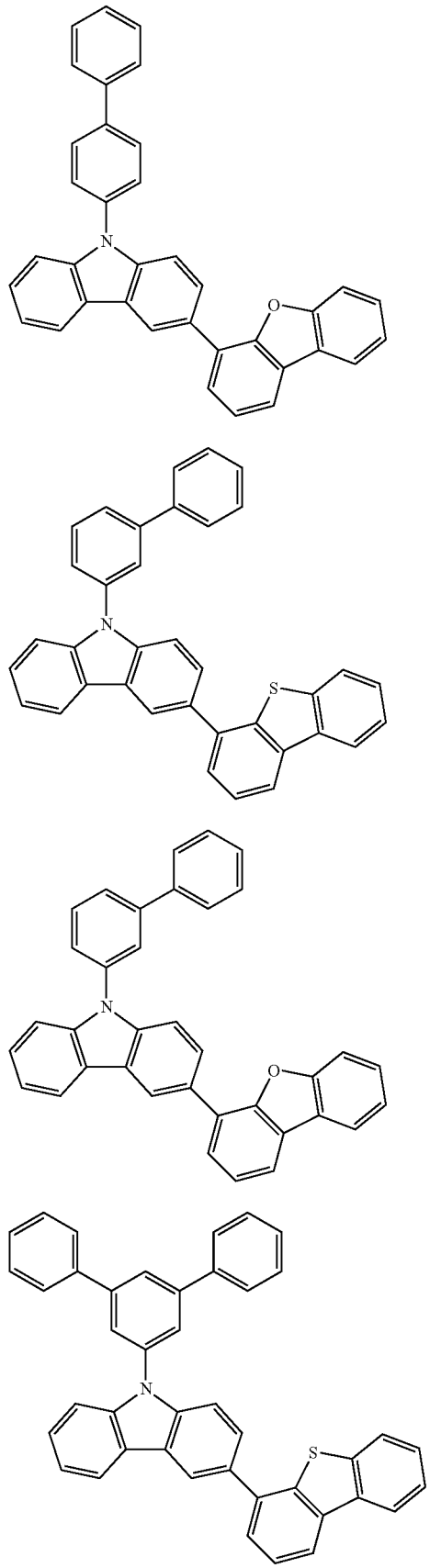
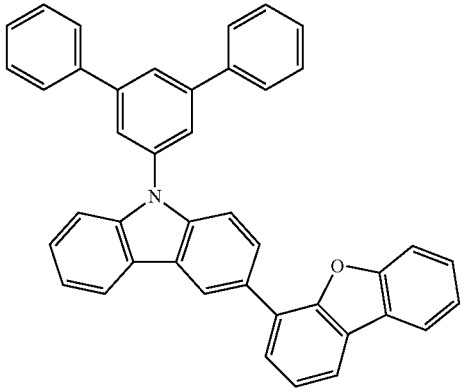
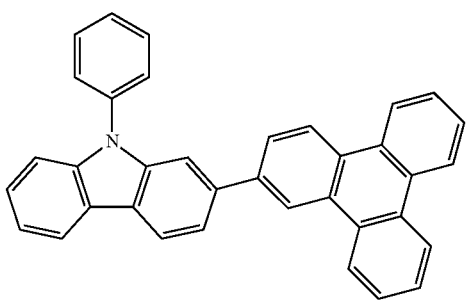
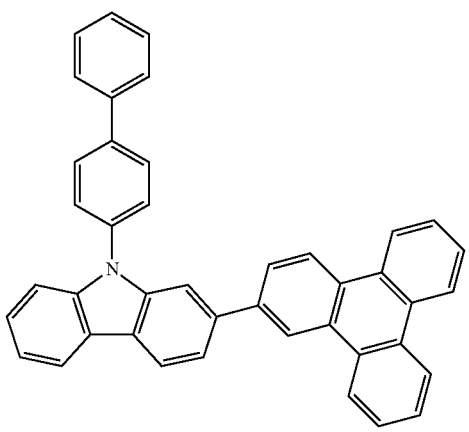

A76 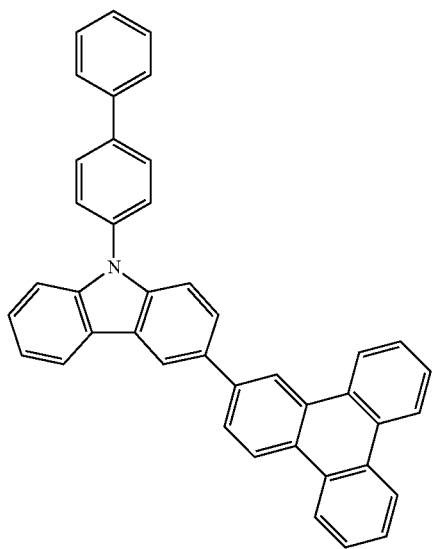
A77 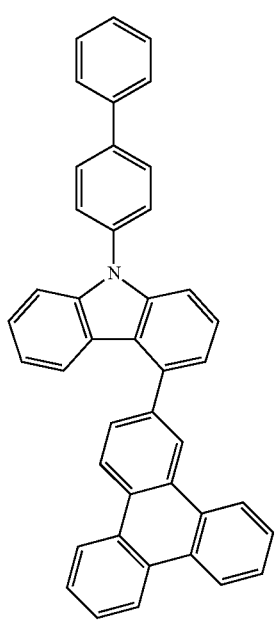
A78 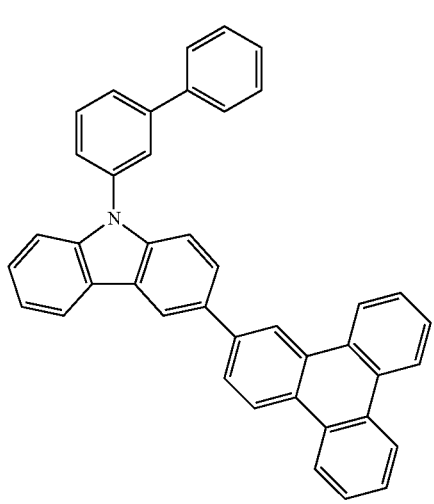
A79 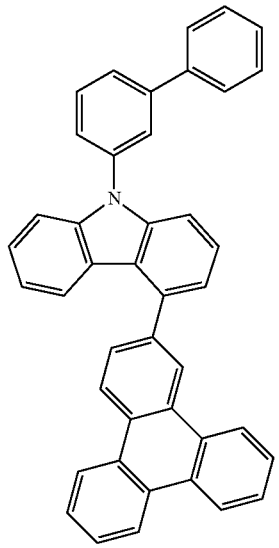
A80 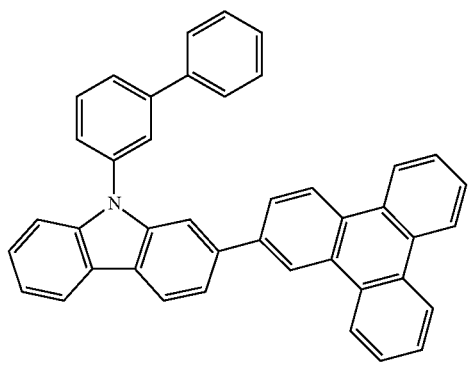
A81 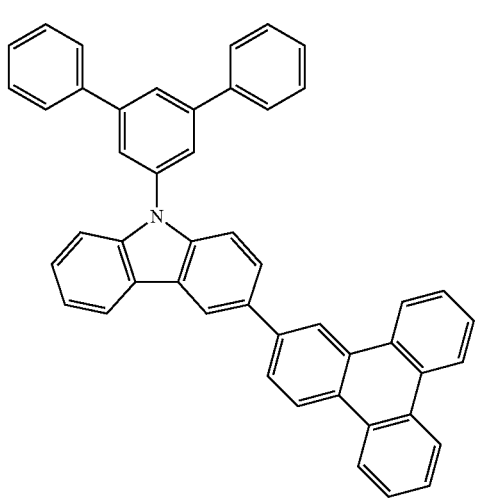

A82
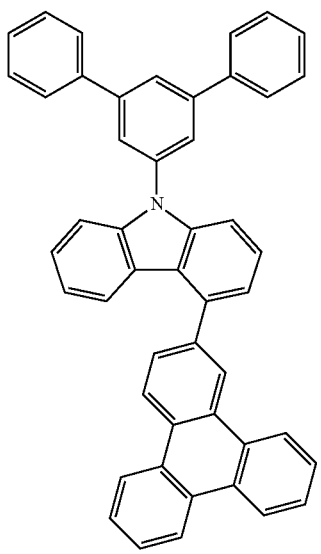
A83
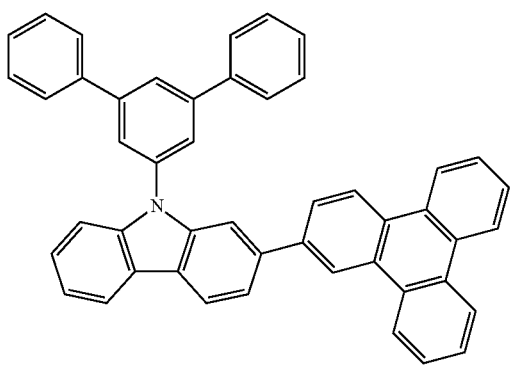
B1
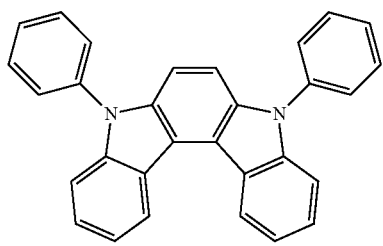
B2
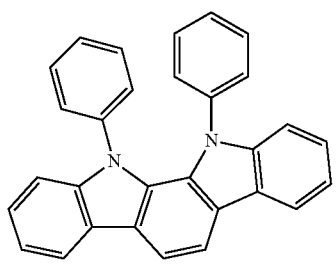
B3
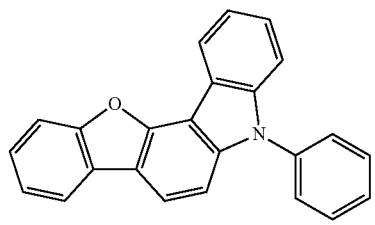
B4
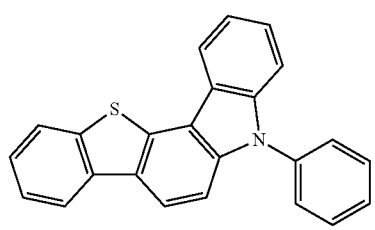
B5
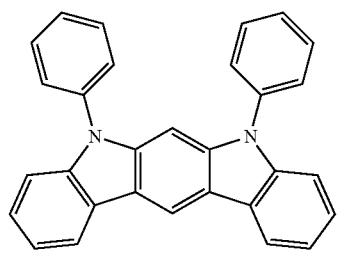
B6
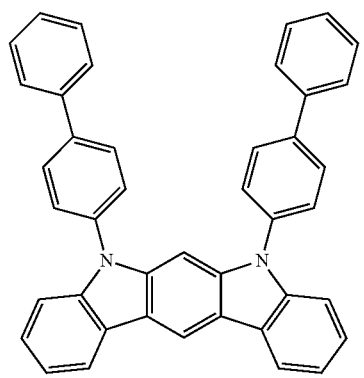
B7
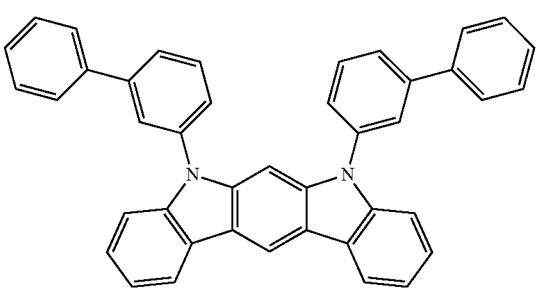

B8
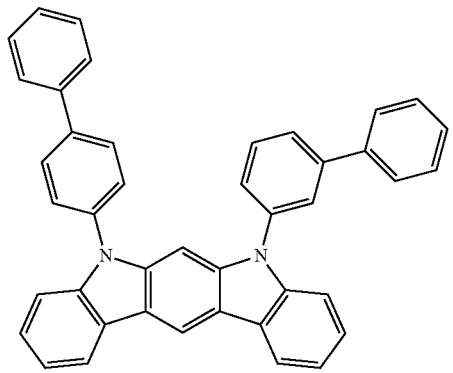
B9
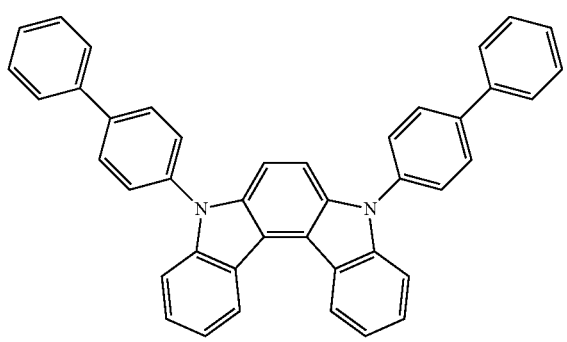
B10
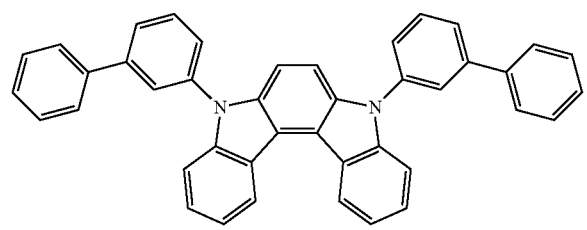
B11
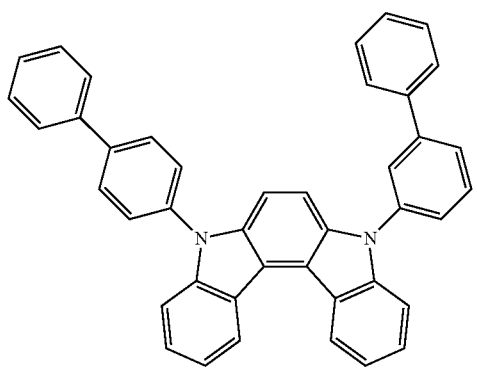
B12
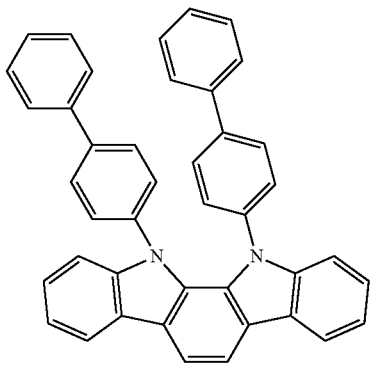
B13
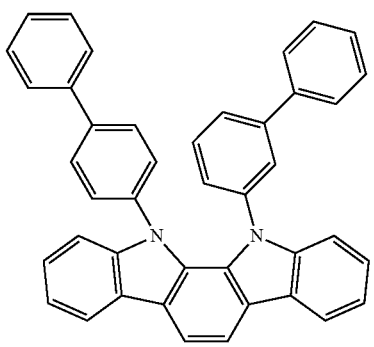
B14
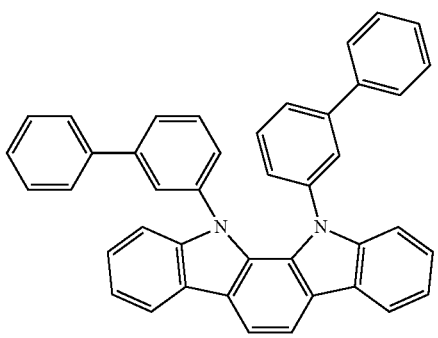
B15
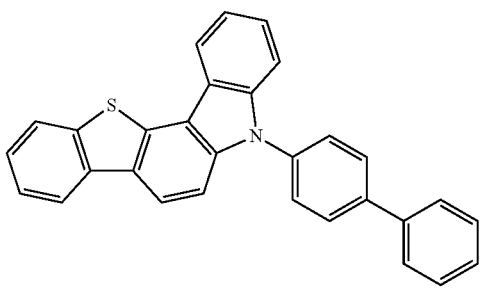
B16
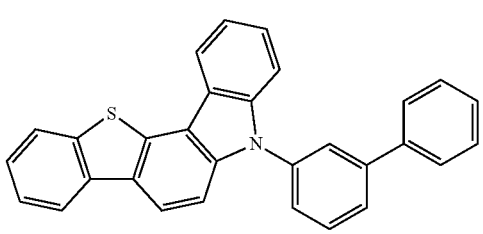

-continued

B17
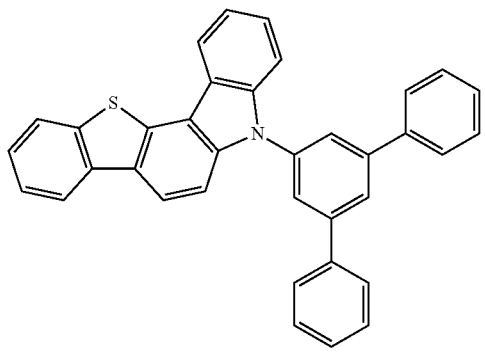

B18
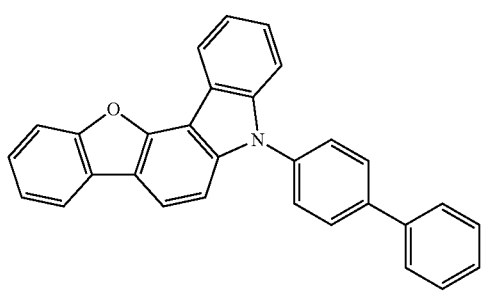

B19
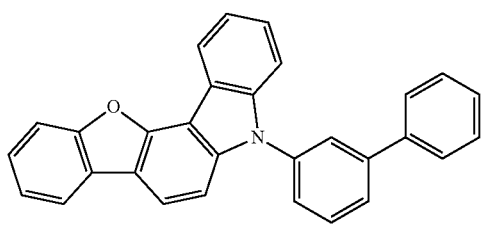

B20
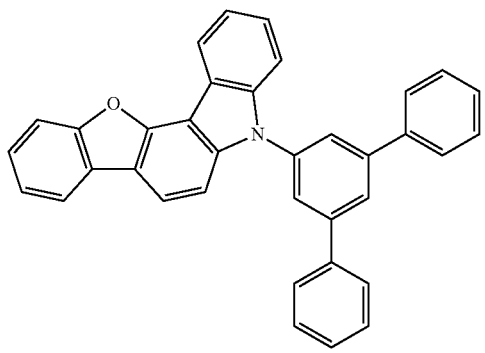

In some embodiments, the emission layer may include at least one selected from Compounds 1 to 12 at Host 1 and at least one selected from Compounds A1 to A83 and B1 to B20 as Host 2, but they are not limited thereto.

When the emission layer includes both Host 1 and Host 2, injection balance of holes and electrons into the emission layer may be effectively controlled, thereby improving light-emitting efficiency and lifespan of an organic light-emitting device.

A weight ratio of the first host and the second host in the emission layer and a weight ratio of Host 1 and Host 2 in the emission layer may be each independently selected from in a range of about 1:99 to about 99:1, for example, in a range of about 10:90 to about 90:10. When the weight ratio of the first host and the second host and the weight ratio of Host 1 and Host 2 satisfy the above described range, injection balance of holes and electrons into the emission layer may be effectively controlled.

The dopant in the emission layer may include a fluorescent dopant which emits light according to a fluorescent emission mechanism, or a phosphorescent dopant which emits light according to a phosphorescent emission mechanism.

According to an embodiment, the dopant in the emission layer may be a phosphorescent dopant, and the phosphorescent dopant may include an organometallic compound represented by Formula 81:

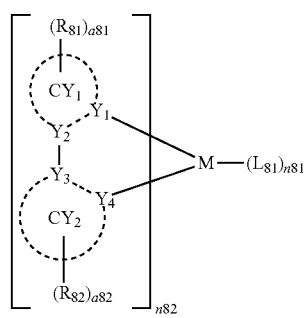

Formula 81 wherein in Formula 81,

M is iridium (Ir), platinum (Pt), osmium (Os), titanium (Ti), zirconium (Zr), hafnium (Hf), europium (Eu), terbium (Tb), or thulium (Tm);

$Y_1$ to $Y_4$ are each independently carbon (C) or nitrogen (N);

$Y_1$ and $Y_2$ are linked to each other via a single bond or a double bond, and $Y_3$ and $Y_4$ are linked to each other via a single bond or a double bond;

$CY_1$ and $CY_2$ may be each independently selected from a benzene, a naphthalene, a fluorene, a spiro-fluorene, an indene, a pyrrole, a thiophene, a furan, an imidazole, a pyrazole, a thiazole, an isothiazole, an oxazole, an isoxazole, a pyridine, a pyrazine, a pyrimidine, a pyridazine, a quinoline, an isoquinoline, a benzoquinoline, a quinoxaline, a quinazoline, a carbazole, a benzoimidazole, a benzofuran, a benzothiophene, an isobenzothiophene, a benzoxazole, an isobenzoxazole, a triazole, a tetrazole, an oxadiazole, a triazine, a dibenzofuran, and a dibenzothiophene, and $CY_1$ and $CY_2$ may be optionally linked to each other via a single bond or an organic linking group;

$R_{81}$ and $R_{82}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, —SF$_5$, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —N(Q₁)(Q₂), —Si(Q₃)(Q₄)(Q₅), and —B(Q₆)(Q₇);

a81 and a82 may be each independently an integer selected from 1 to 5, n81 may be an integer selected from 0 to 4, n82 may be an integer selected from 1, 2, and 3; and L₈₁ may be a monovalent organic ligand, a divalent organic ligand or a trivalent organic ligand.

R₈₁ and R₈₂ may be the same in connection with R₄₁.

The phosphorescent dopant may include at least one selected from Compounds PD1 to PD78, but it is not limited thereto:

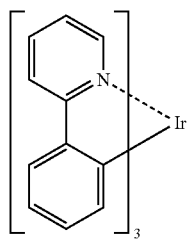

PD1

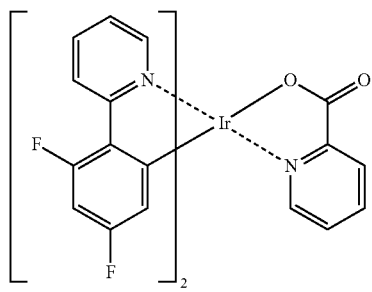

PD2

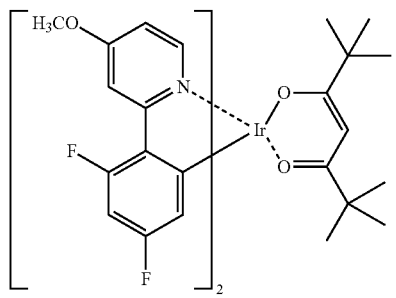

PD3

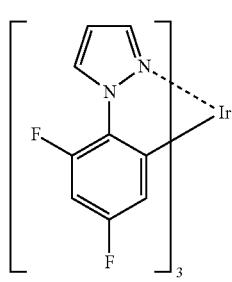

PD4

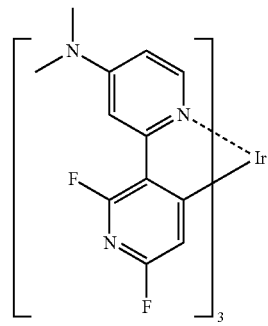

PD5

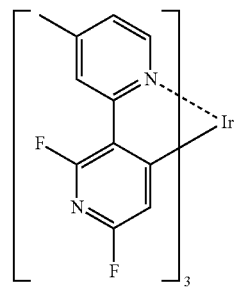

PD6

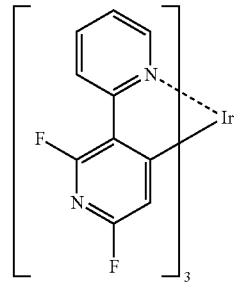

PD7

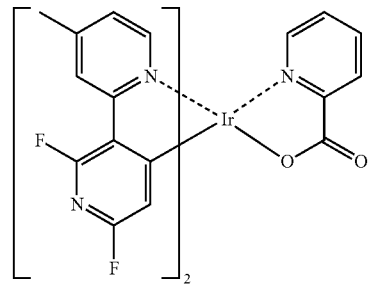

PD8

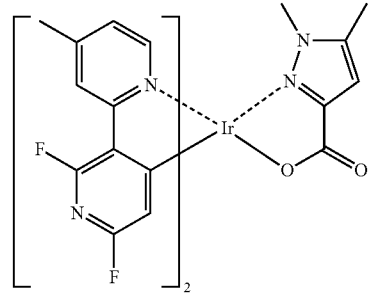

PD9

PD10 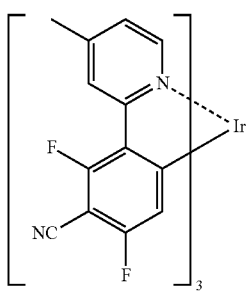
PD11 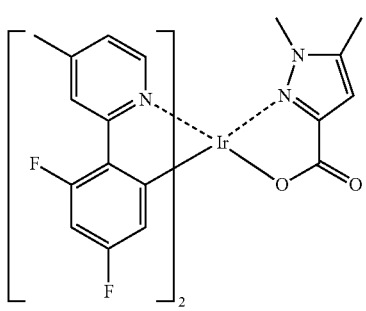
PD12 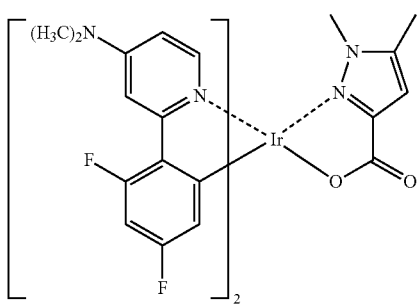
PD13 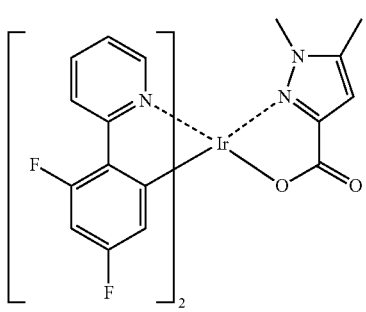
PD14 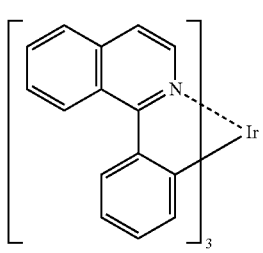
PD15 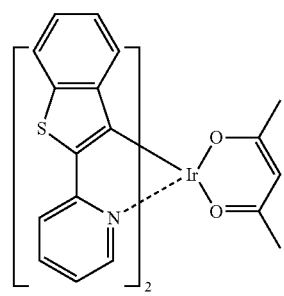
PD16 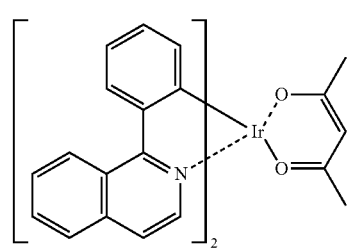
PD17 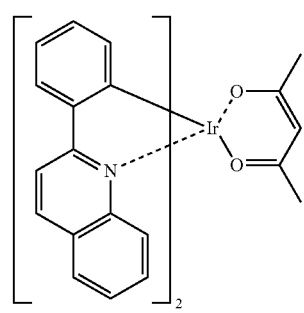
PD18 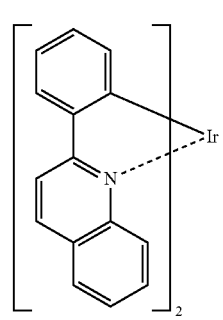
PD19 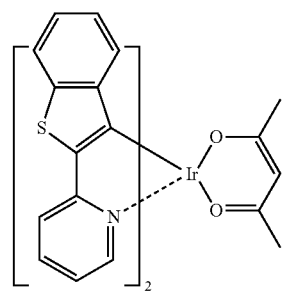

PD20 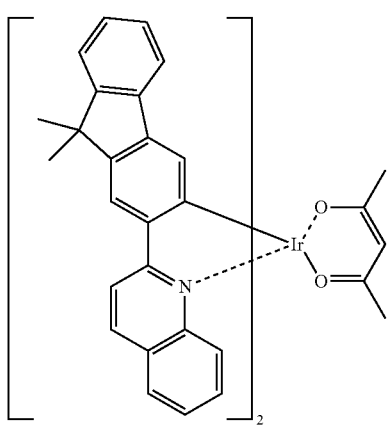
PD21 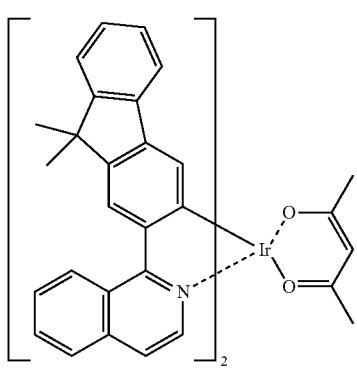
PD22 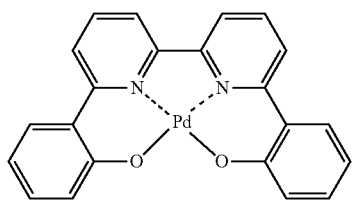
PD23 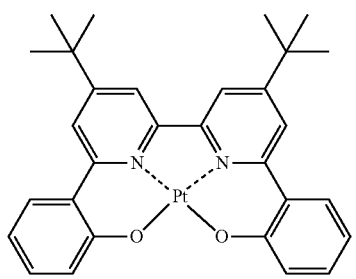
PD24 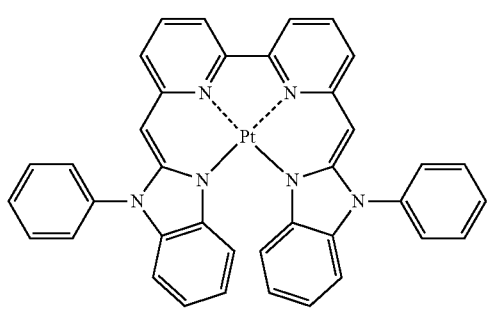
PD25 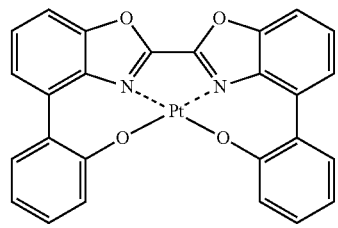
PD26 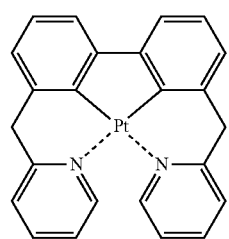
PD27 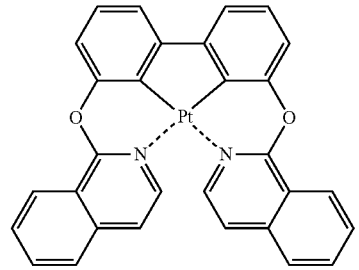
PD28 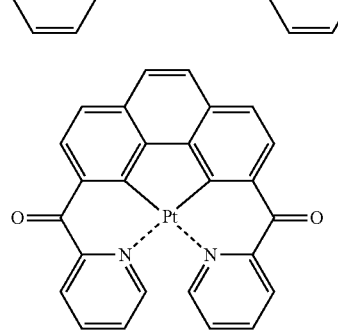
PD29 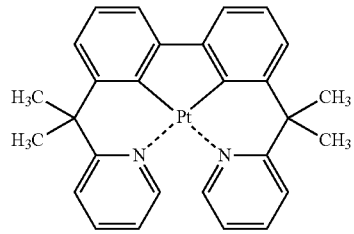
PD30 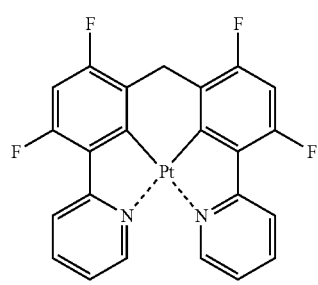

PD31 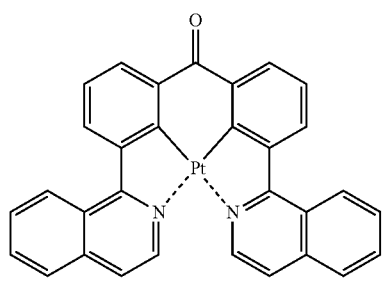
PD32 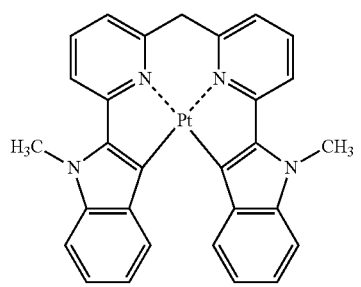
PD33 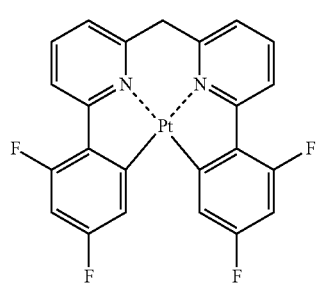
PD34 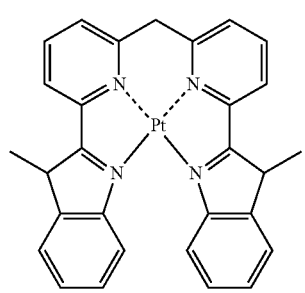
PD35 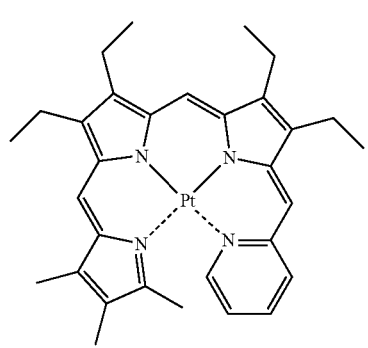
PD36 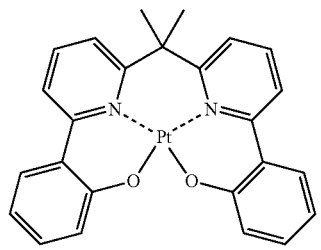
PD37 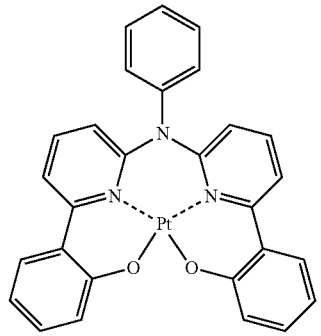
PD38 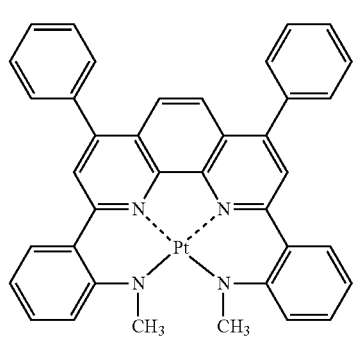
PD39 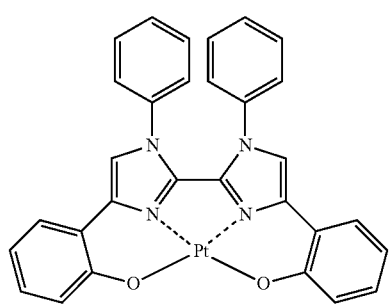
PD40 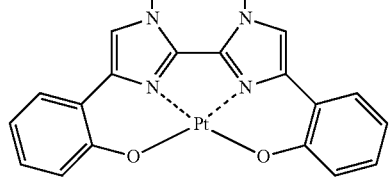
PD41 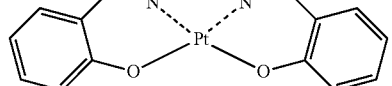

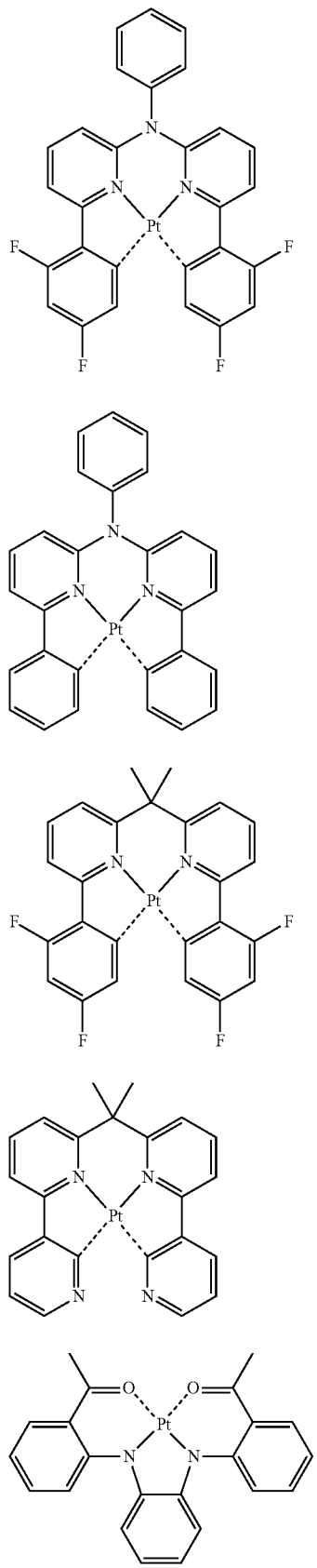
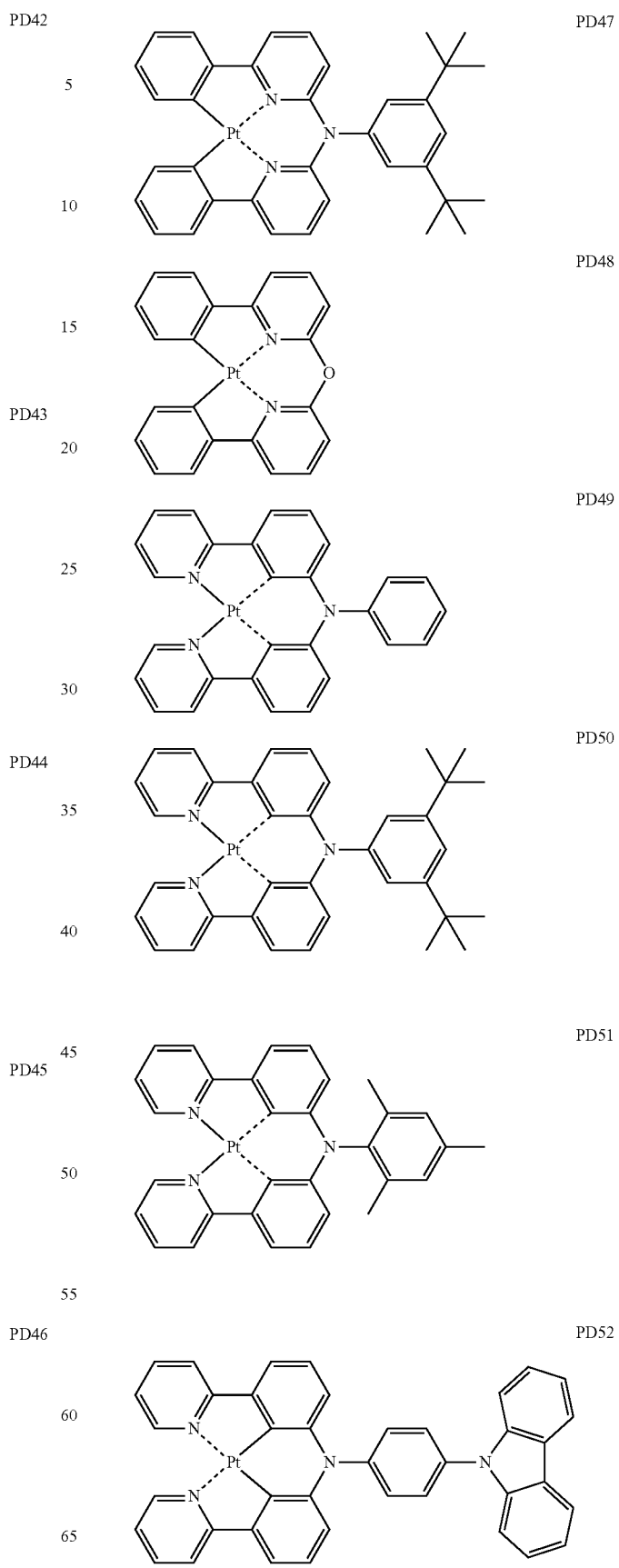

-continued
PD53
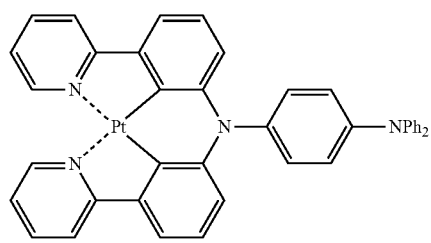
PD54
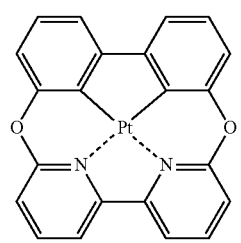
PD55
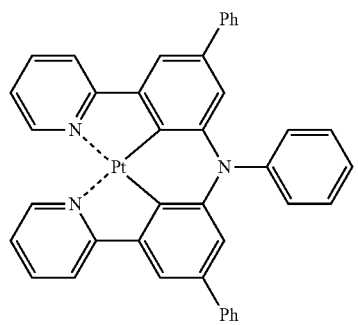
PD56
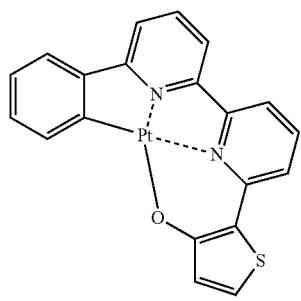
PD57
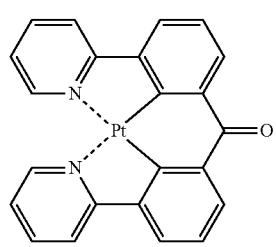
-continued
PD58
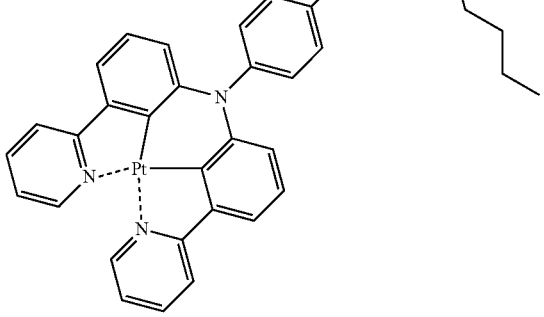
PD59
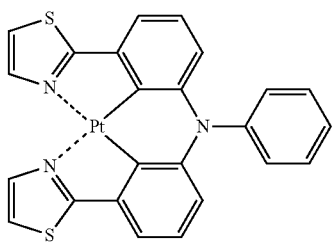
PD60
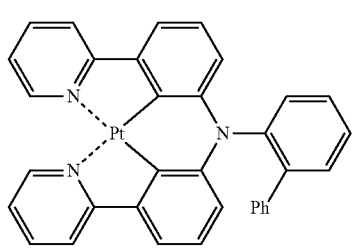
PD61
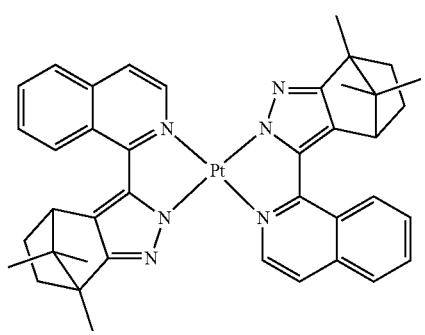
PD62
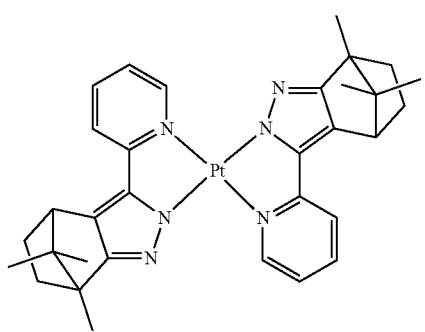

-continued
PD63 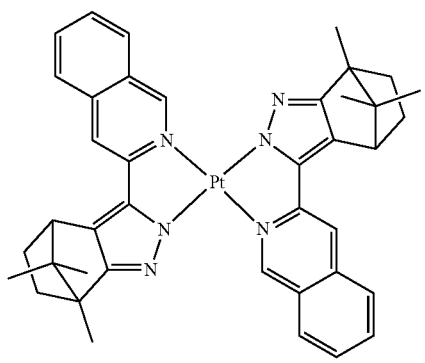
PD64 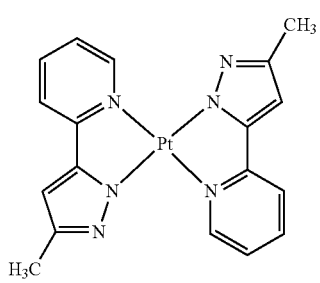
PD65 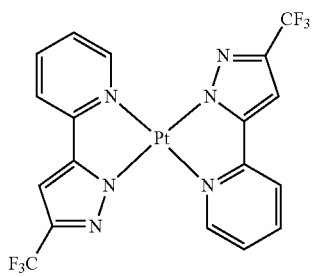
PD66 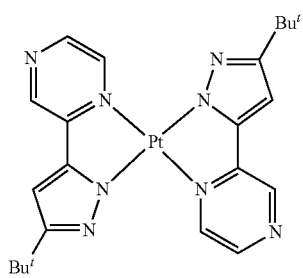
PD67 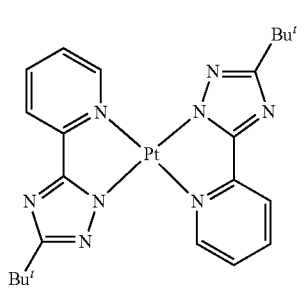
-continued
PD68 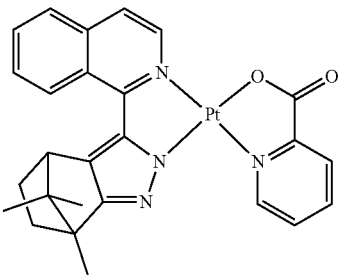
PD69 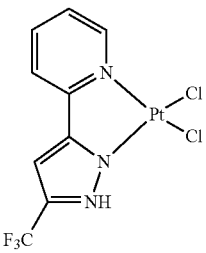
PD70 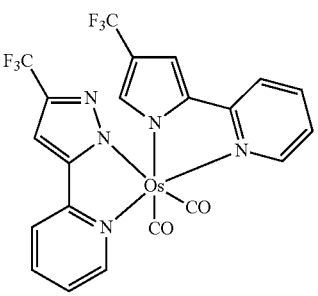
PD71 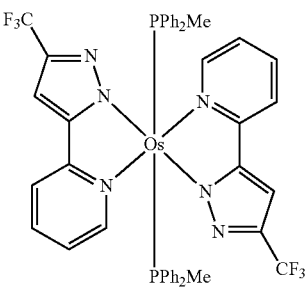
PD72 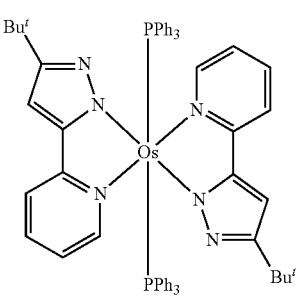

-continued
PD73
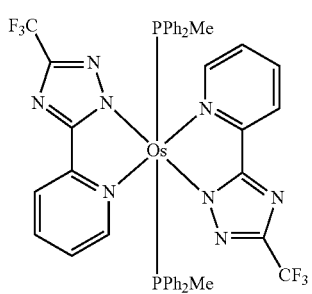
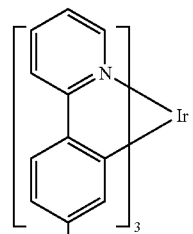 PD77
PD74
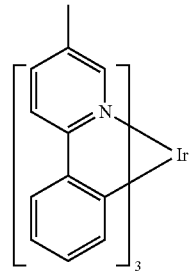 PD78
PD75
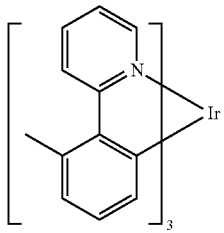
Alternatively, the phosphorescent dopant may include PtOEP below:
PD76
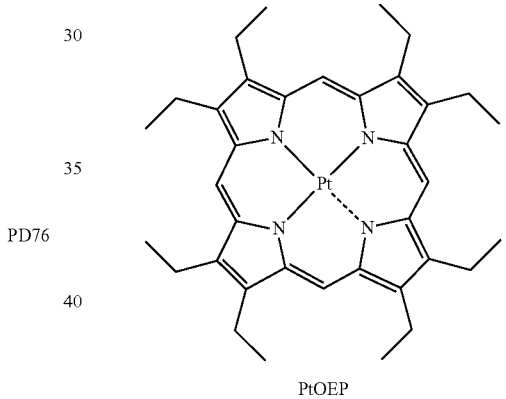
PtOEP
The fluorescent dopant may include at least one selected from DPAVBi, BDAVBi, TBPe, DCM, DCJTB, Coumarin 6, and C545T.
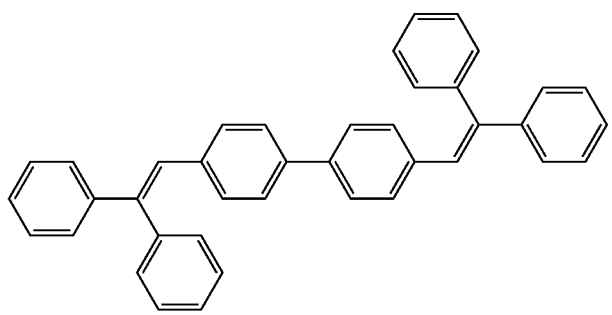
DPVBi -continued

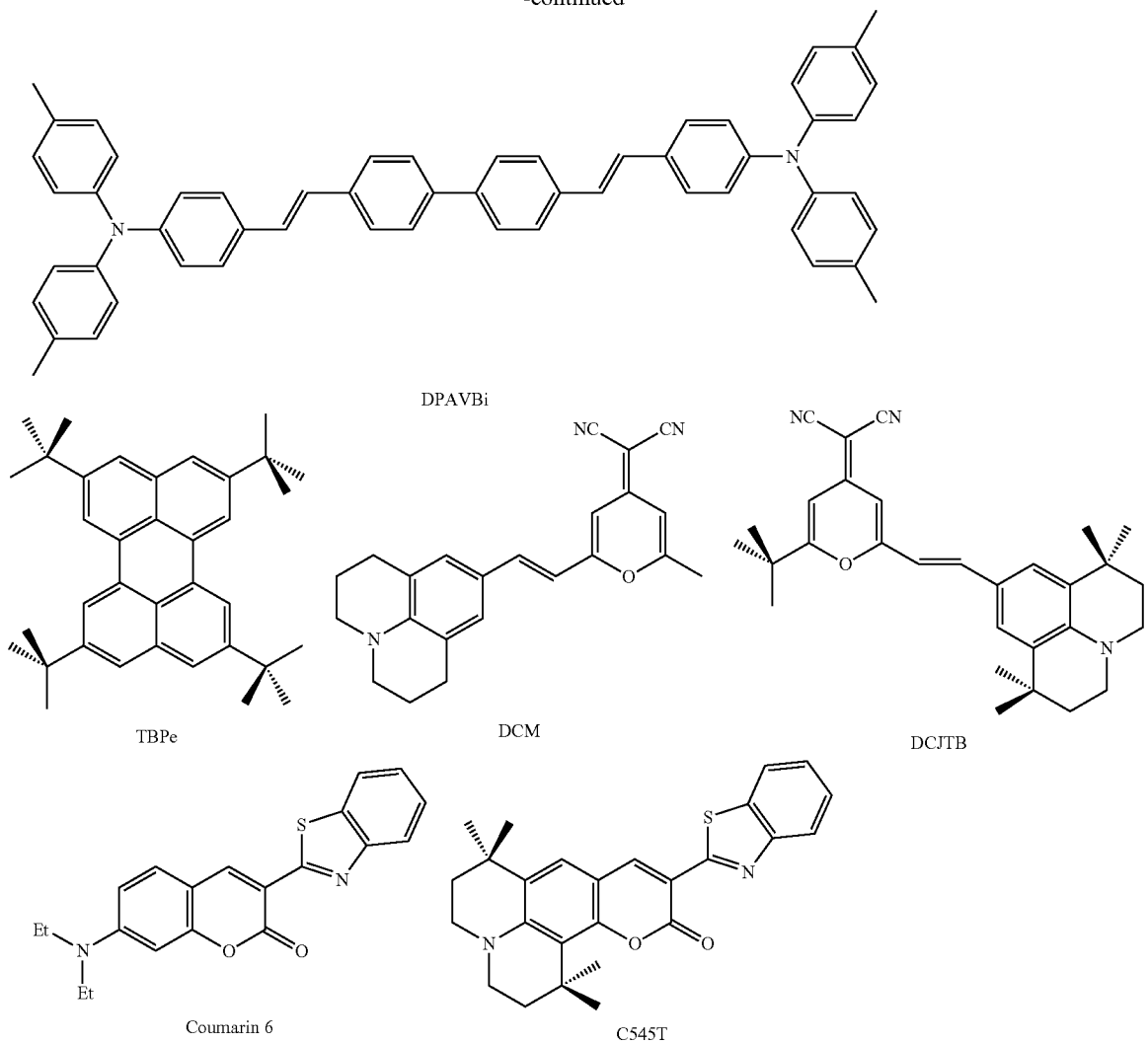

When the emission layer includes the host and the dopant, an amount of the dopant may be selected from in a range of about 0.01 to about 20 parts by weight based on about 100 parts by weight of the host, but the amount is not limited thereto.

A thickness of the emission layer may be in a range of about 100 Å to about 1,000 Å, for example, about 200 Å to about 600 Å. When the thickness of the emission layer is within this range, excellent light-emission characteristics may be obtained without a substantial increase in driving voltage.

Then, an electron transport region may be disposed on the emission layer.

The electron transport region may include at least one selected from a hole blocking layer, an electron transport layer, and an electron injection layer, but is not limited thereto.

For example, the electron transport region may have a structure of a hole blocking layer/an electron transport layer/an electron injection layer or an electron transport layer/an electron injection layer, but it is not limited thereto.

The electron transport layer may have a single layer structure or a multi-layer structure including two or more different materials.

The conditions for forming a hole blocking layer, an electron transport layer, and an electron injection layer may be inferred based on the conditions for forming the hole injection layer.

When the electron transport region includes a hole blocking layer, the hole blocking layer may, for example, include at least one of BCP and Bphen, but is not limited thereto.

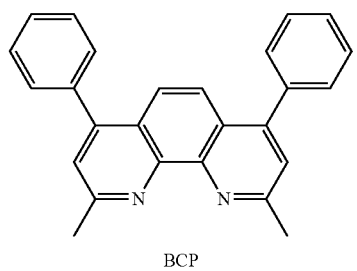

-continued

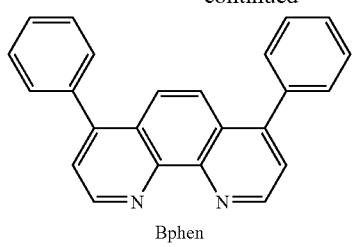
Bphen

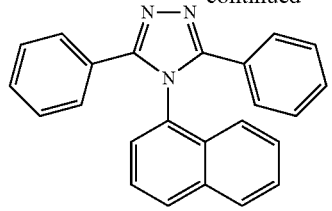
NTAZ

A thickness of the hole blocking layer may be in a range of about 20 Å to about 1,000 Å, for example, about 30 Å to about 300 Å. When the thickness of the hole blocking layer is within this range, excellent hole blocking characteristics may be obtained without a substantial increase in driving voltage.

The electron transport layer may further include at least one selected from BCP, Bphen, Alq$_3$, BAlq, TAZ, and NTAZ.

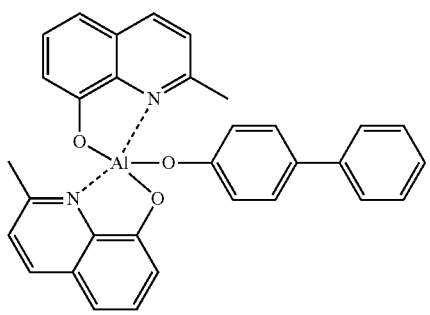
Alq$_3$

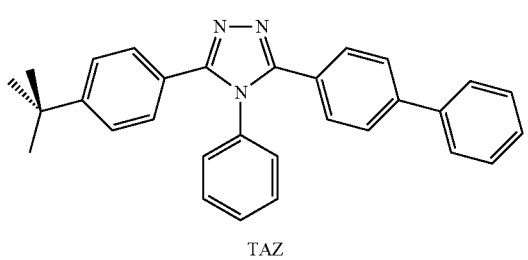
BAlq

Alternatively, the electron transport layer may include at least one selected from Compounds ET1 and ET2, but is not limited thereto.

ET1

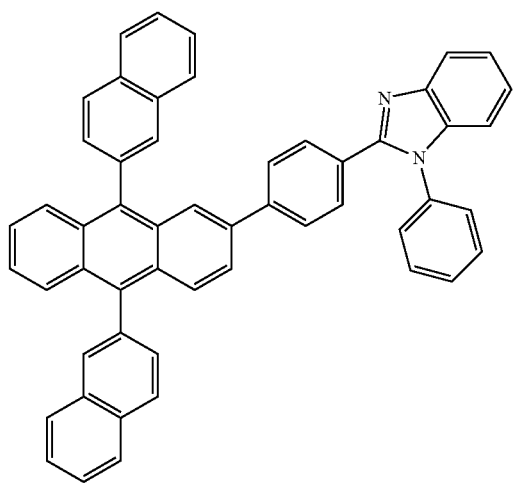

ET2

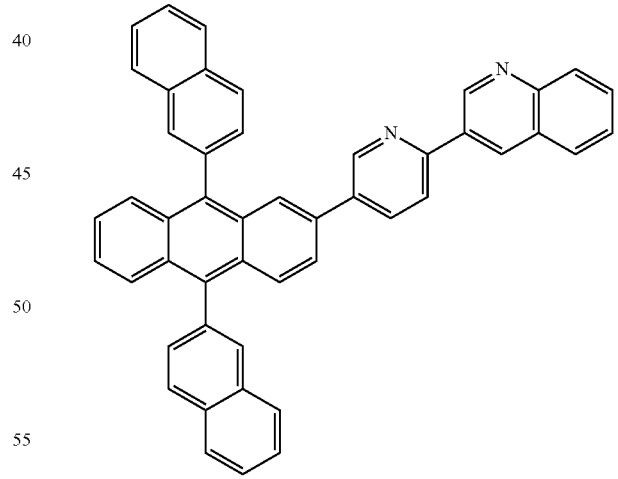

A thickness of the electron transport layer may be in a range of about 100 Å to about 1,000 Å, for example, about 150 Å to about 500 Å. When the thickness of the electron transport layer is within this range, excellent electron transport characteristics may be obtained without a substantial increase in driving voltage.

The electron transport layer may further include a metal-containing material in addition to the materials described above.

TAZ

The metal-containing material may include a Li complex. The Li complex may include, for example, Compound ET-D1 (lithium quinolate, LiQ) or ET-D2.

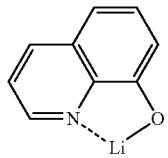

ET-D1

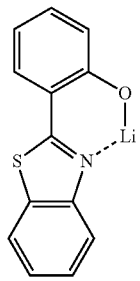

ET-D2

The electron transport region may include an electron injection layer (EIL) that facilitates electron injection from the second electrode 19.

The electron injection layer may include at least one selected from, LiF, NaCl, CsF, Li$_2$O, and BaO.

A thickness of the electron injection layer may be in a range of about 1 Å to about 100 Å, for example, about 3 Å to about 90 Å. When the thickness of the electron injection layer is within this range, excellent electron injection characteristics may be obtained without a substantial increase in driving voltage.

The second electrode 19 is disposed on the organic layer 15. The second electrode 19 may be a cathode. A material for the second electrode 19 may be a material having a relatively low work function, such as a metal, an alloy, an electrically conductive compound, and a mixture thereof. Detailed examples of the material for forming the second electrode 19 are lithium (Li), magnesium (Mg), aluminum (Al), aluminum-lithium (Al—Li), calcium (Ca), magnesium-indium (Mg—In), and magnesium-silver (Mg—Ag). Alternatively, ITO or IZO may be used to form a transmissive second electrode 19 to manufacture a top emission light-emitting device, and such a variation may be possible.

Hereinbefore, the organic light-emitting device has been described with reference to FIG. 1, but it is not limited thereto.

A $C_1$-$C_{60}$ alkyl group as used herein refers to a linear or branched aliphatic hydrocarbon monovalent group having 1 to 60 carbon atoms. Detailed examples thereof are a methyl group, an ethyl group, a propyl group, an isobutyl group, a sec-butyl group, a tert-butyl group, a pentyl group, an iso-amyl group, and a hexyl group. A $C_1$-$C_{60}$ alkylene group as used herein refers to a divalent group having the same structure as the $C_1$-$C_{60}$ alkyl group.

A $C_1$-$C_{60}$ alkoxy group as used herein refers to a monovalent group represented by —OA$_{101}$ (wherein A$_{101}$ is the $C_1$-$C_{60}$ alkyl group). Detailed examples thereof are a methoxy group, an ethoxy group, and an isopropyloxy group.

A $C_2$-$C_{60}$ alkenyl group as used herein refers to a group formed by substituting at least one carbon double bond in the middle or at the terminal of the $C_2$-$C_{60}$ alkyl group. Detailed examples thereof are an ethenyl group, a propenyl group, and a butenyl group. A $C_2$-$C_{60}$ alkenylene group as used herein refers to a divalent group having the same structure as a $C_2$-$C_{60}$ alkenyl group.

A $C_2$-$C_{60}$ alkynyl group as used herein refers to a group formed by substituting at least one carbon triple bond in the middle or at the terminal of the $C_2$-$C_{60}$ alkyl group. Detailed examples thereof are an ethenyl group and a propenyl group. A $C_2$-$C_{60}$ alkynylene group as used herein refers to a divalent group having the same structure as a $C_2$-$C_{60}$ alkynyl group.

A $C_3$-$C_{10}$ cycloalkyl group as used herein refers to a monovalent monocyclic saturated hydrocarbon group including 3 to 10 carbon atoms. Detailed examples thereof are a cyclopropyl group, a cyclobutyl group, a cyclopentyl group, a cyclohexyl group, and a cycloheptyl group. A $C_3$-$C_{10}$ cycloalkylene group as used herein refers to a divalent group having the same structure as a $C_3$-$C_{10}$ cycloalkyl group.

A $C_1$-$C_{10}$ heterocycloalkyl group as used herein refers to a monovalent monocyclic group including at least one hetero atom selected from N, O, P, and S as a ring-forming atom and 1 to 10 carbon atoms. Detailed examples thereof are a tetrahydrofuranyl group and a tetrahydrothiophenyl group. A $C_1$-$C_{10}$ heterocycloalkylene group as used herein refers to a divalent group having the same structure as a $C_1$-$C_{10}$ heterocycloalkyl group.

A $C_3$-$C_{10}$ cycloalkenyl group as used herein refers to a monovalent monocyclic group including 3 to 10 carbon atoms and at least one double bond in the ring thereof, which is not aromatic. Detailed examples thereof are a cyclopentenyl group, a cyclohexenyl group, or a cycloheptenyl group. A $C_3$-$C_{10}$ cycloalkenylene group as used herein refers to a divalent group having the same structure as a $C_3$-$C_{10}$ cycloalkenyl group.

A $C_1$-$C_{10}$ heterocycloalkenyl group as used herein refers to a monovalent monocyclic group including at least one hetero atom selected from N, O, P, and S as a ring-forming atom, 1 to 10 carbon atoms, and at least one double bond in its ring. Detailed examples of the $C_1$-$C_{10}$ heterocycloalkenyl group are a 2,3-dihydrofuranyl group and a 2,3-dihydrothiophenyl group. A $C_1$-$C_{10}$ heterocycloalkenylene group as used herein refers to a divalent group having the same structure as a $C_1$-$C_{10}$ heterocycloalkenyl group.

A $C_6$-$C_{60}$ aryl group as used herein refers to a monovalent group having a carbocyclic aromatic system having 6 to 60 carbon atoms, and a $C_6$-$C_{60}$ arylene group as used herein refers to a divalent group having a carbocyclic aromatic system having 6 to 60 carbon atoms. Detailed examples of the $C_6$-$C_{60}$ aryl group are a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include two or more rings, wherein the rings may be fused to each other.

A $C_1$-$C_{60}$ heteroaryl group as used herein refers to a monovalent group having a carbocyclic aromatic system having at least one hetero atom selected from N, O, P, and S as a ring-forming atom and 1 to 60 carbon atoms. A $C_1$-$C_{60}$ heteroarylene group as used herein refers to a divalent group having a carbocyclic aromatic system having at least one hetero atom selected from N, O, P, and S as a ring-forming atom and 1 to 60 carbon atoms. Detailed examples of the $C_1$-$C_{60}$ heteroaryl group are a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each include two or more rings, the rings may be fused to each other.

A $C_6$-$C_{60}$ aryloxy group as used herein indicates —$OA_{102}$ (wherein $A_{102}$ is the $C_6$-$C_{60}$ aryl group), and a $C_6$-$C_{60}$ arylthio group as used herein indicates —$SA_{103}$ (wherein $A_{103}$ is the $C_6$-$C_{60}$ aryl group).

A monovalent non-aromatic condensed polycyclic group as used herein refers to a monovalent group that has two or more rings condensed to each other, only carbon atoms (for example, the number of carbon atoms may be in a range of 8 to 60) as ring forming atoms, wherein the molecular structure as a whole is non-aromatic. Detailed examples of the non-aromatic condensed polycyclic group includes a fluorenyl group. A divalent non-aromatic condensed polycyclic group as used herein refers to a divalent group having the same structure as the monovalent non-aromatic condensed polycyclic group.

A monovalent non-aromatic condensed hetero-polycyclic group as used herein refers to a monovalent group that has two or more rings condensed to each other, has a heteroatom selected from N, O, P, and S, other than carbon atoms (for example, the number of carbon atoms may be in a range of 2 to 60), as ring-forming atoms, wherein the molecular structure as a whole is non-aromatic. Detailed example of the monovalent non-aromatic condensed heteropolycyclic group includes a carbazolyl group. A divalent non-aromatic condensed hetero-polycyclic group as used herein refers to a divalent group having the same structure as the monovalent non-aromatic condensed hetero-polycyclic group.

"A phenyl group-substituted with a phenyl group" as used herein refers to "a phenyl group substituted with at least one phenyl group".

"A phenyl group-substituted with a $C_1$-$C_{20}$ alkyl group" as used herein refers to "a phenyl group-substituted with at least one $C_1$-$C_{20}$ alkyl group".

Hereinafter, an organic light-emitting device according to an embodiment will be described in detail with reference to Synthesis Examples and Examples, however, the inventive concept is not limited thereto. The wording "B was used instead of A" used in describing Synthesis Examples means that an amount of B used was identical to an amount of A used based on molar equivalence.

EXAMPLE

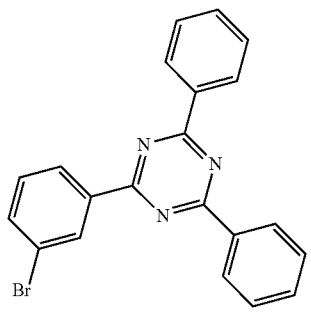

E-1

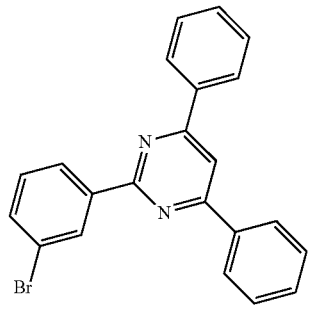

E-2

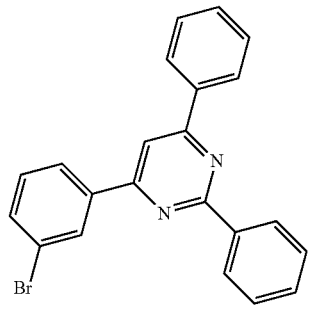

E-3

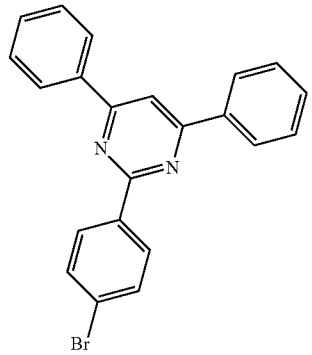

E-4

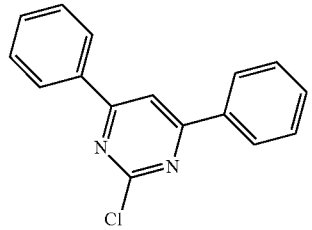

E-5

E-6

E-7

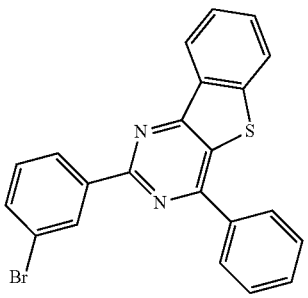

E-8

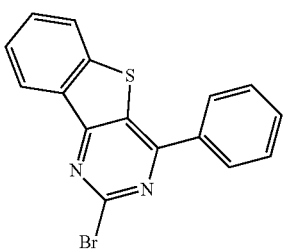

E-9

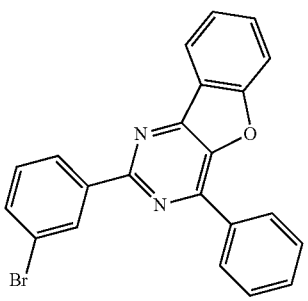

E-10

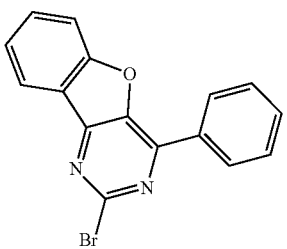

Synthesis Example 1: Synthesis of Compound 1

1) Synthesis of Intermediate A

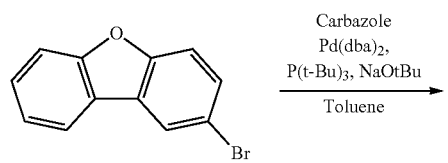

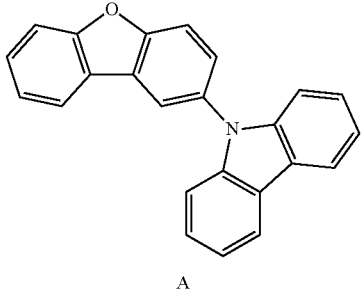

A 10.0 grams (g) (40.0 millimoles (mmol)) of 2-bromodibenzofuran, 8.121 g (49.0 mmol) of carbazole, 1.85 g (2.0 mmol) of $Pd_2(dba)_3$, 0.57 g (3.00 mmol) of tri-tert-butylphosphine, and 9.72 g (101 mmol) of sodium-tert-butoxide were dissolved in 120 mL of toluene. The mixture was stirred under reflux at the heating temperature of 110° C. for 18 hours under a nitrogen atmosphere. The mixture was allowed to come to room temperature, and the organic layer was extracted with 200 mL of water and 800 mL of dichloromethane. The organic layer was dried using magnesium sulfate ($MgSO_4$), and the solvent removed by evaporation. The residue was separated and purified by a silica gel chromatography to obtain 11.5 g of Intermediate A (yield: 85%). The product was confirmed by liquid chromatography-mass spectrometry (LC-MS) and high-performance liquid chromatography (HPLC).

LC-MS (m/z)=$C_{24}H_{15}NO$ ($M^+$) 333.

2) Synthesis of Intermediate B

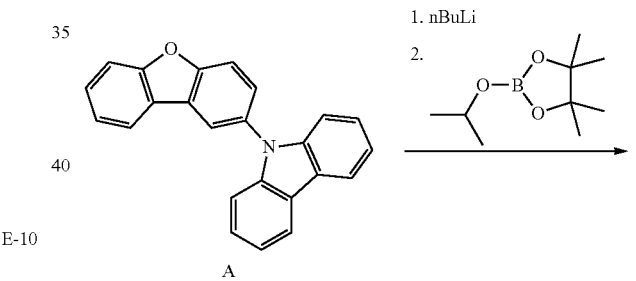

A

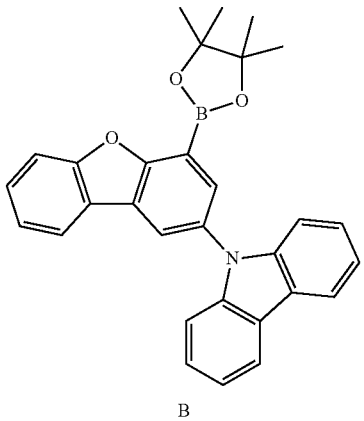

B 11.5 g (34.5 mmol) of Intermediate A was dissolved in 80 mL of tetrahydrofuran (THF), and stirred at −78° C. for 10 minutes. 20.7 mL (51.7 mmol) of 1.6 molar (M) n-butyl-lithium solution in hexanes was slowly added dropwise for 30 minutes, and the resulting mixture was stirred at −78° C. for 4 hours. 10.6 mL (51.7 mmol) of 2-isopropoxy-4,4,5,5- tetramethyl-1,3,2-dioxaborolane was added thereto. After 15 minutes of stirring, the mixture was allowed to warm to room temperature and was stirred at room temperature for 5 hours. 100 mL of water was added, and the mixture was stirred. The organic layer was extracted with three 150 mL portions of dichloromethane. The organic layer was dried with $MgSO_4$, and the solvent was removed by evaporation. The residue was recrystallized with dichloromethane and methanol to obtain 11.5 g of Intermediate B (yield: 75%). The obtained compound was confirmed by using LC-MS and HPLC.

LC-MS (m/z)=$C_{30}H_{26}BNO_3$ ($M^+$) 459.

3) Synthesis of Compound 1

4.28 g (31.0 mmol) of $K_2CO_3$ were dissolved in 100 mL of THF and 50 mL of distilled water, and stirred under reflux at 80° C. for 18 hours. The resulting mixture was allowed to cool to room temperature. 100 mL of distilled water was added, and the mixture was stirred. The organic layer was extracted with three 150 mL portions of dichloromethane. The organic layer was dried with $MgSO_4$, and the solvent was removed by evaporation. The residue was separated and purified by a silica gel chromatography to obtain 7.80 g of Compound 1 (yield: 78%). The product was confirmed by using LC-MS and HPLC.

LC-MS (m/z)=$C_{45}H_{28}N_4O$ ($M^+$) 640.

Synthesis Example 2: Synthesis of Compound 2

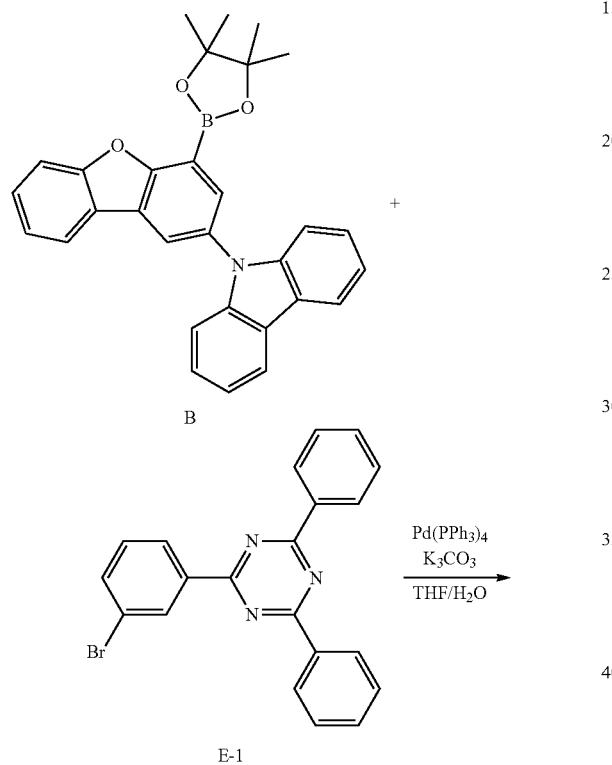

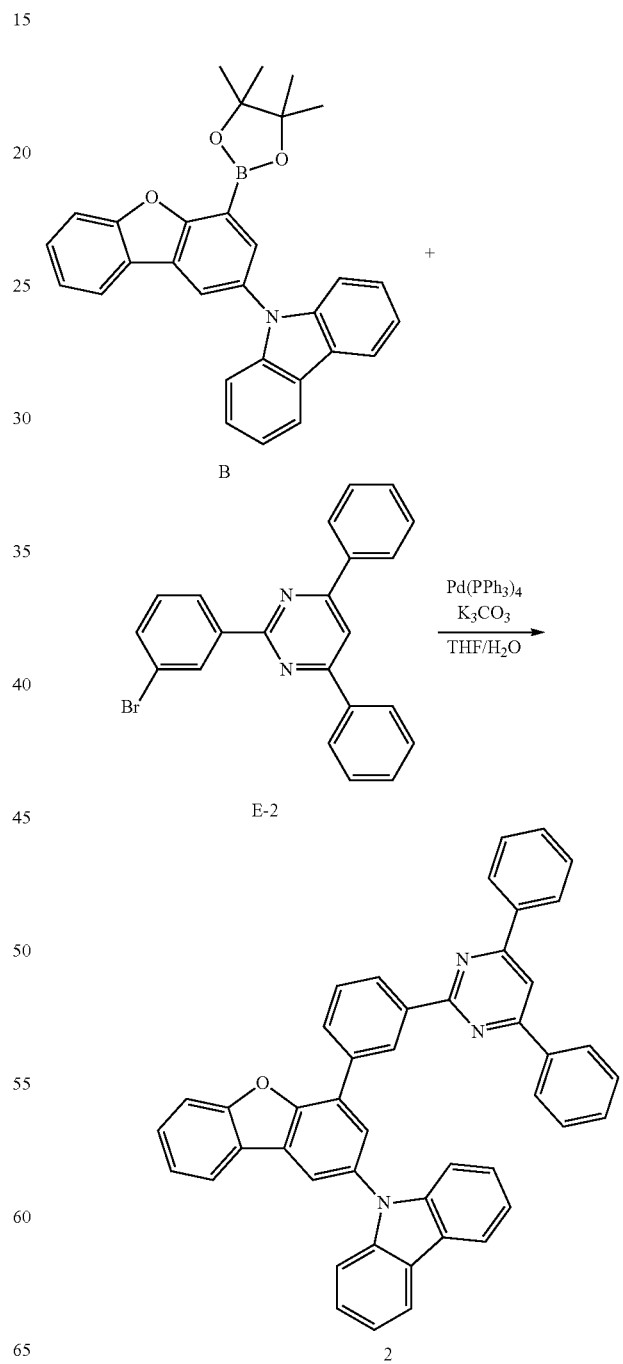

7.55 g (17.0 mmol) of Intermediate B, 6.01 g (15.5 mmol) of Compound E-1, 0.94 g (0.31 mmol) of $Pd(PPh_3)_4$, and 4.33 g of Compound 2 (yield: 63%) was obtained in the same manner as in Synthesis Example 1 except that 4.07 g (10.5 mmol) of Compound E-2 was used instead of 4.07 g (10.5 mmol) of Compound E-1. The product was confirmed by using LC-MS and HPLC.

LC-MS (m/z)=$C_{46}H_{29}N_3O$ (M$^+$) 639.

Synthesis Example 3: Synthesis of Compound 3

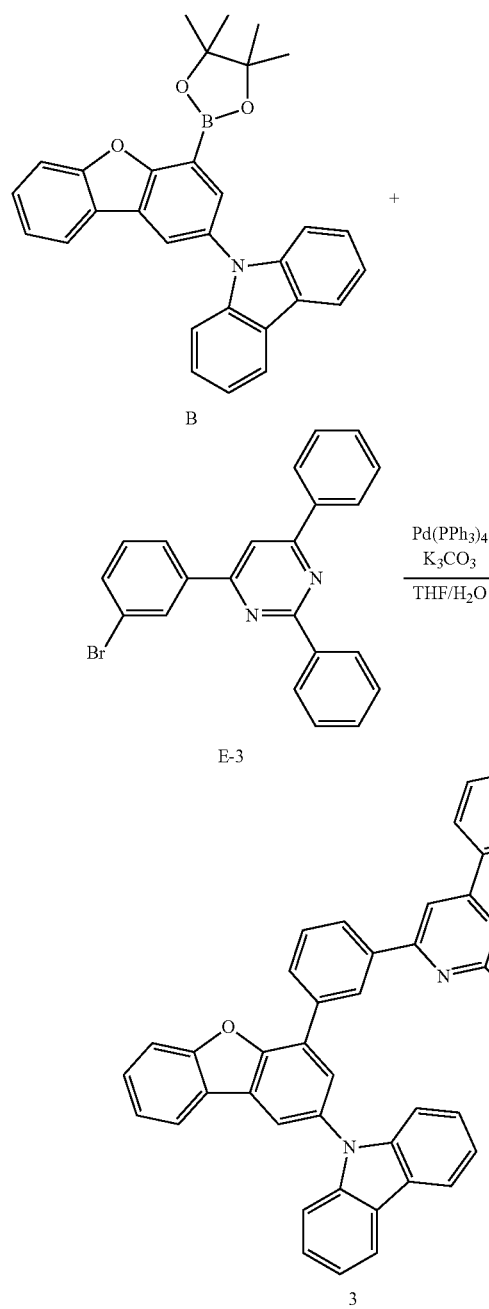

Synthesis Example 4: Synthesis of Compound 4

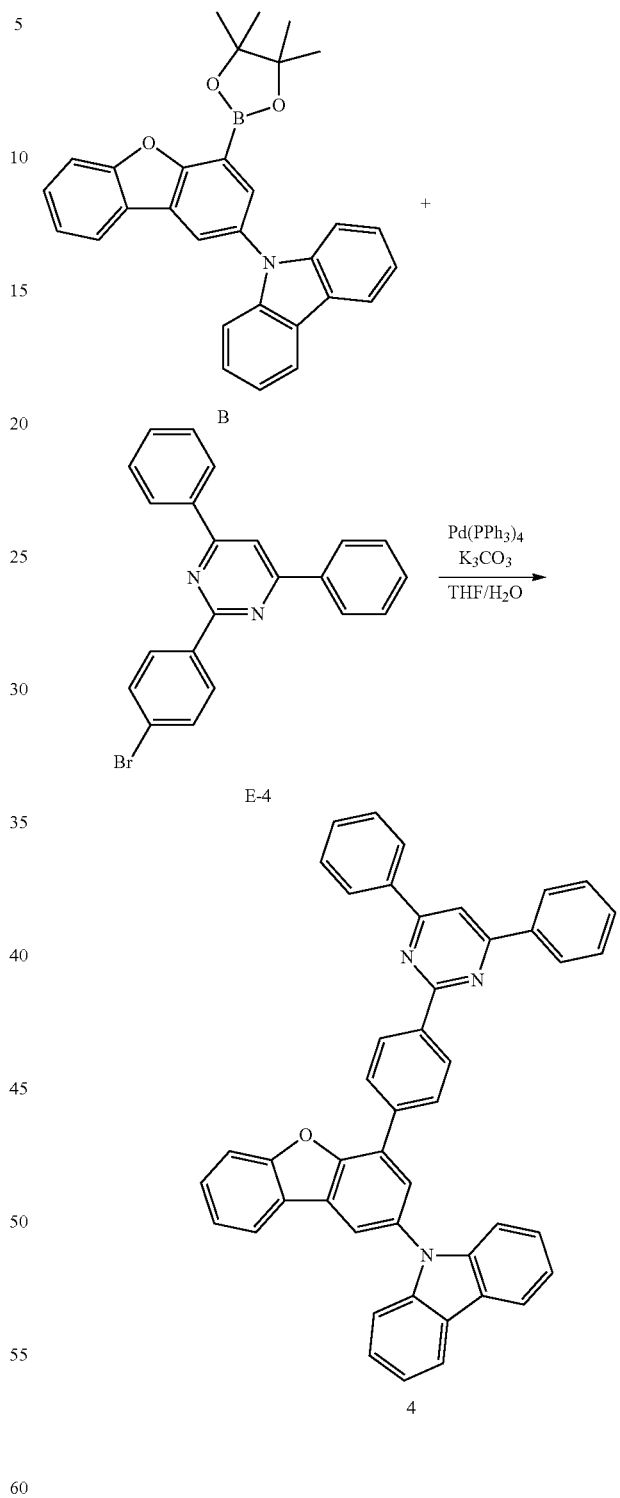

4.10 g of Compound 3 (yield: 61%) was obtained in the same manner as in Synthesis Example 1 except that 4.07 g (10.5 mmol) of Compound E-3 was used instead of 4.07 g (10.5 mmol) of Compound E-1. The product was confirmed by using LC-MS and HPLC.

LC-MS (m/z)=$C_{46}H_{29}N_3O$ (M$^+$) 639.

4.84 g of Compound 4 (yield: 72%) was obtained in the same manner as in Synthesis Example 1 except that 4.07 g (10.5 mmol) of Compound E-4 was used instead of 4.07 g (10.5 mmol) of Compound E-1. The product was confirmed by using LC-MS and HPLC.

LC-MS (m/z)=$C_{46}H_{29}N_3O$ (M$^+$) 639.

Synthesis Example 5: Synthesis of Compound 5

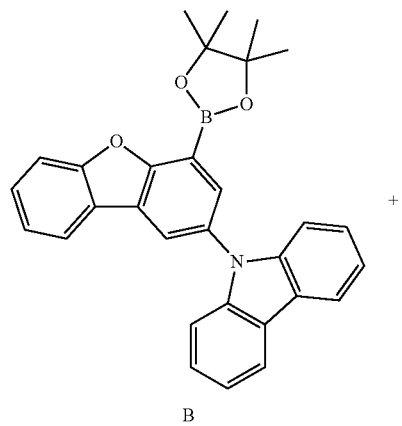

Synthesis Example 6: Synthesis of Compound 6

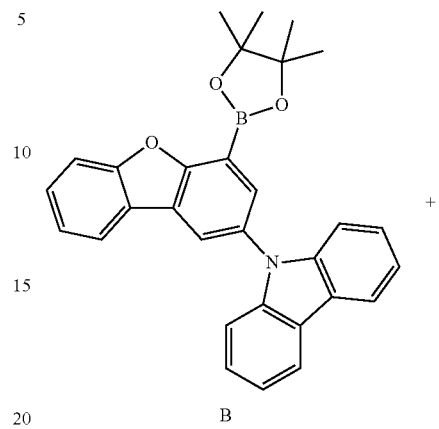

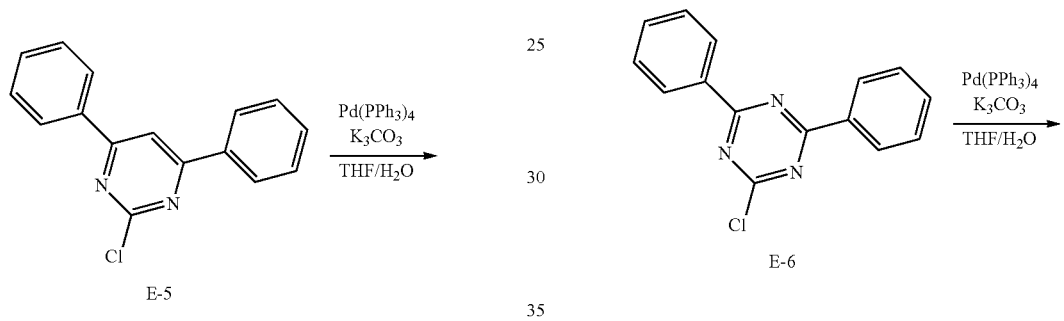

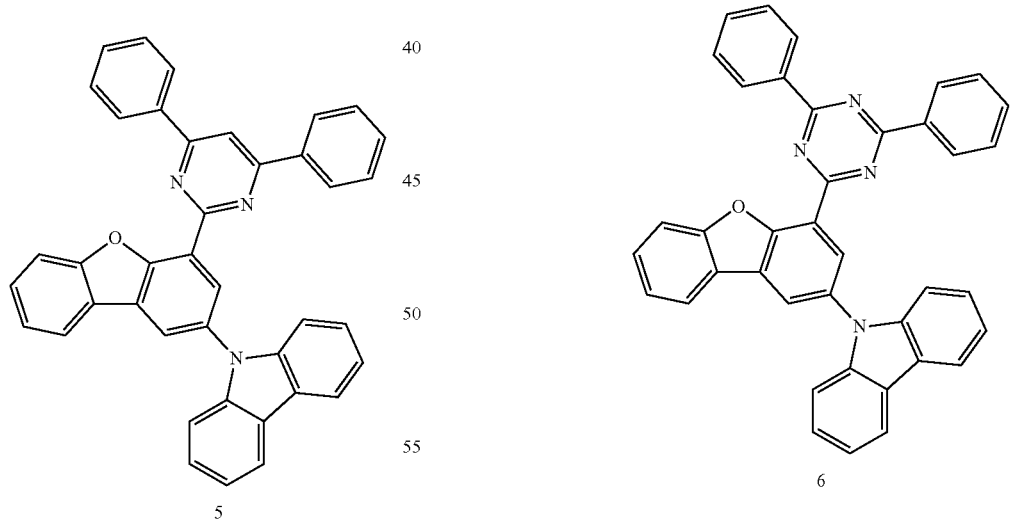

5.45 g of Compound 5 (yield: 92%) was obtained in the same manner as in Synthesis Example 1 except that 2.80 g (10.5 mmol) of Compound E-2 was used instead of 4.07 g (10.5 mmol) of Compound E-1. The product was confirmed by using LC-MS and HPLC.

LC-MS (m/z)=$C_{40}H_{25}N_3O$ (M+) 564.

4.51 g of Compound 6 (yield: 77%) was obtained in the same manner as in Synthesis Example 1 except that 2.81 g (10.5 mmol) of Compound E-6 was used instead of 4.07 g (10.5 mmol) of Compound E-1. The product was confirmed by using LC-MS and HPLC.

LC-MS (m/z)=$C_{39}H_{24}N_4O$ (M+) 563.

Synthesis Example 7: Synthesis of Compound 7

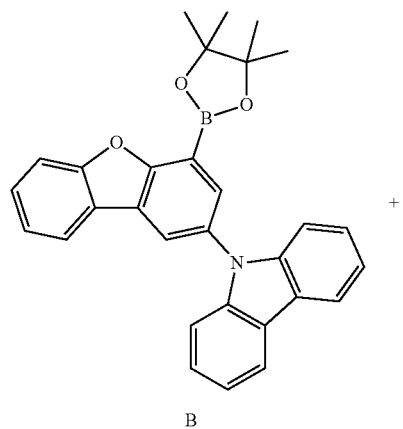

B

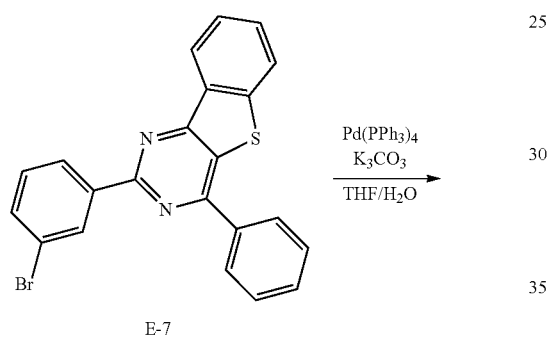

E-7

7

5.56 g of Compound 7 (yield: 79%) was obtained in the same manner as in Synthesis Example 1 except that 4.38 g (10.5 mmol) of Compound E-7 was used instead of 4.07 g (10.5 mmol) of Compound E-1. The product was confirmed by using LC-MS and HPLC.

LC-MS (m/z)=$C_{45}H_{27}N_3OS$ (M$^+$) 669.

Synthesis Example 8: Synthesis of Compound 8

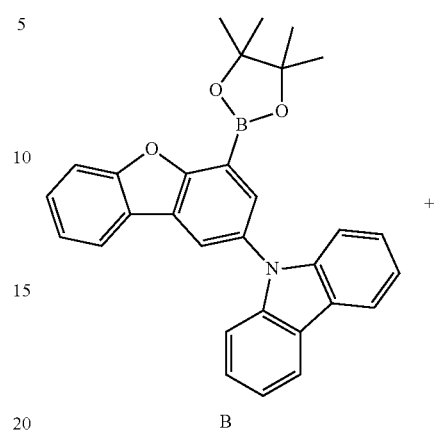

B

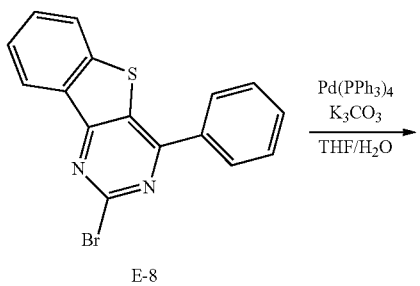

E-8

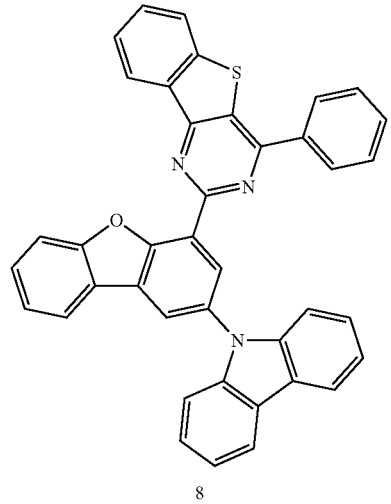

8

5.49 g of Compound 8 (yield: 88%) was obtained in the same manner as in Synthesis Example 1 except that 3.58 g (10.5 mmol) of Compound E-8 was used instead of 4.07 g (10.5 mmol) of Compound E-1. The product was confirmed by using LC-MS and HPLC.

LC-MS (m/z)=$C_{40}H_{23}N_3OS$ (M$^+$) 593.

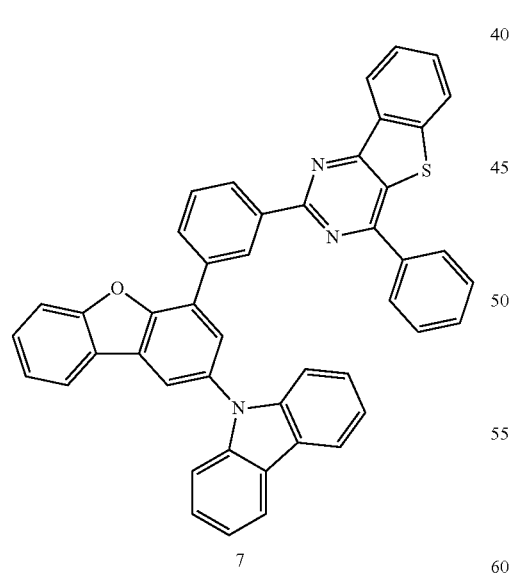

Synthesis Example 9: Synthesis of Compound 9

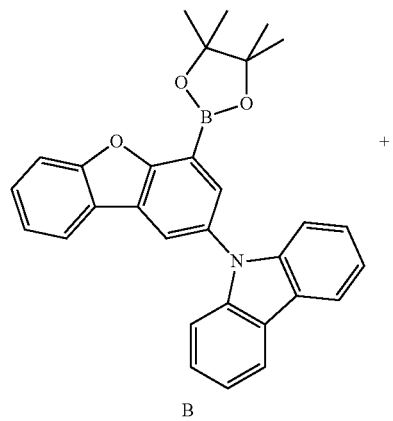

+

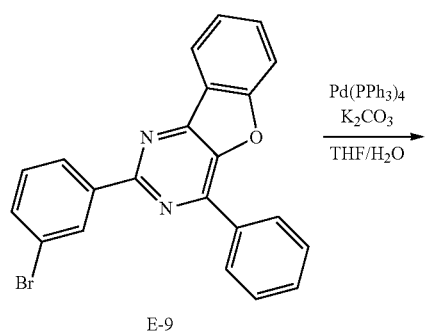

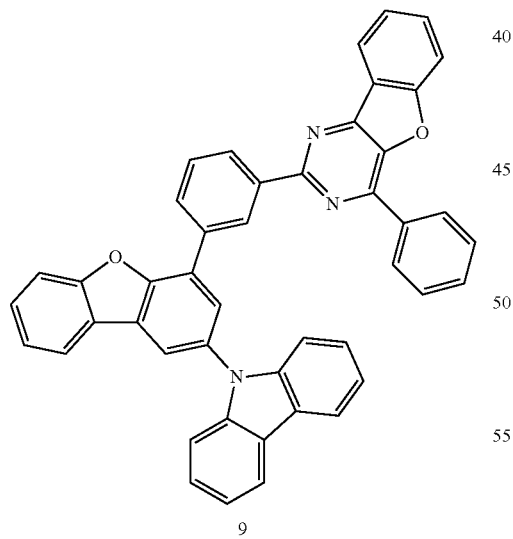

4.81 g of Compound 9 (yield: 70%) was obtained in the same manner as in Synthesis Example 1 except that 4.21 g (10.5 mmol) of Compound E-9 was used instead of 4.07 g (10.5 mmol) of Compound E-1. The product was confirmed by using LC-MS and HPLC.

LC-MS (m/z)=$C_{46}H_{27}N_3C_2$ (M$^+$) 653.

Synthesis Example 10: Synthesis of Compound 10

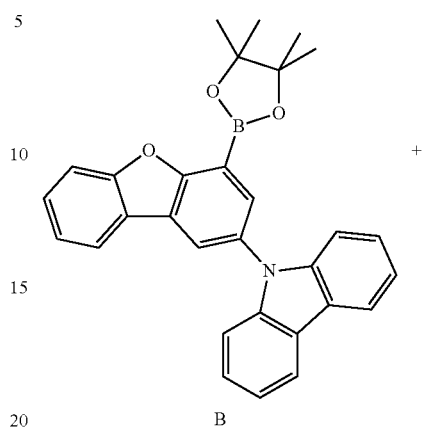

+

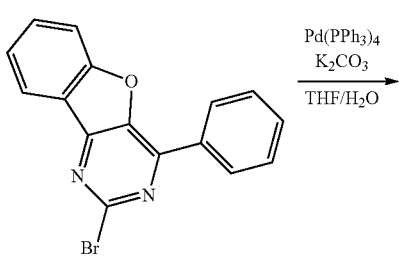

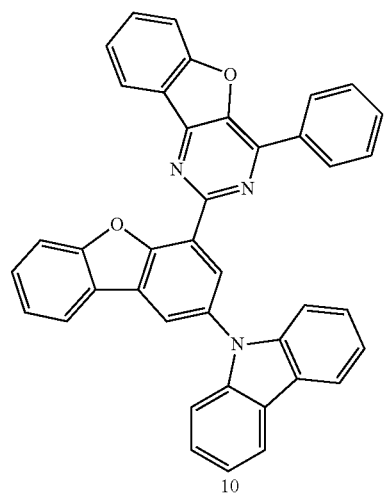

3.88 g of Compound 10 (yield: 64%) was obtained in the same manner as in Synthesis Example 1 except that 3.41 g (10.5 mmol) of Compound E-10 was used instead of 4.07 g (10.5 mmol) of Compound E-1. The product was confirmed by using LC-MS and HPLC.

LC-MS (m/z)=$C_{40}H_{23}N_3C_2$ (M$^+$) 564.

Synthesis Example 11: Synthesis of Compound 11

1) Synthesis of Intermediate C

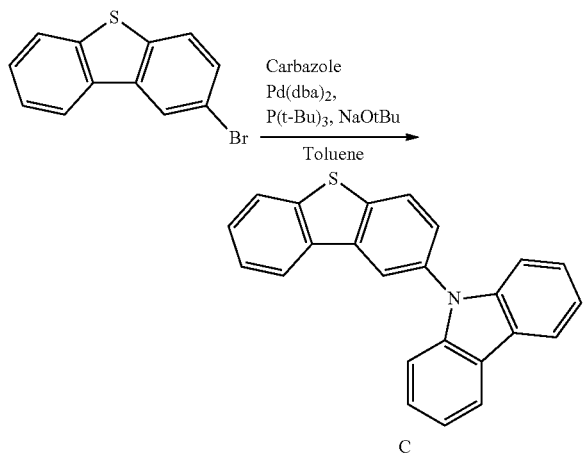

30.0 g (114 mmol) of 2-bromodibenzothiophene, 21.0 g (125 mmol) of carbazole, 0.65 g (1.14 mmol) of Pd(dba)$_2$, 0.69 g (3.42 mmol) of tri-tert-butylphosphine, and 12.1 g (125 mmol) of sodium-tert-butoxide were dissolved in 360 mL of toluene. The mixture was stirred under reflux at the heating temperature of 110° C. for 18 hours under a nitrogen atmosphere. The mixture was allowed to cool to room temperature, and the organic layer was extracted with 300 mL of water and 1,000 mL of dichloromethane. The organic layer was dried using MgSO$_4$, and the solvent removed by evaporation. The residue was recrystallized with toluene and methanol to obtain 33.4 g of Intermediate C (yield: 84%). The product was confirmed by using LC-MS and HPLC.

LC-MS (m/z)=C$_{24}$H$_{15}$NS (M$^+$) 349.

2) Synthesis of Compound D

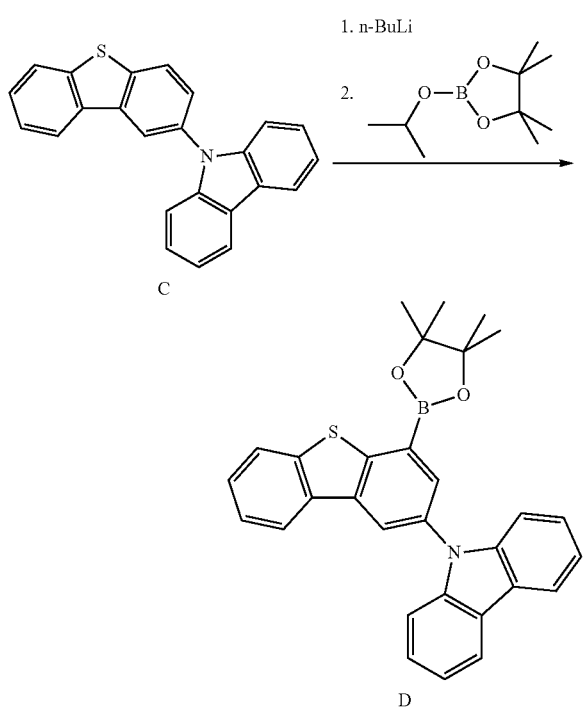

15.0 g (42.9 mmol) of Intermediate C was dissolved in 210 mL of THF, and stirred at −78° C. for 10 minutes. 26.0 mL (64.4 mmol) of 2.5 M n-butyllithium solution in hexanes was slowly added dropwise for 30 minutes, and the resulting mixture was stirred at −78° C. for 4 hours. 16.0 mL (64.4 mmol) of 2-isopropoxy-4,4,5,5-tetramethyl-1,3,2-dioxaborolane was added thereto. After 15 minutes of stirring, the mixture was allowed to warm to room temperature and stirred for 5 hours. 100 mL of water was added to the mixture, and the mixture was further stirred. The organic layer was extracted three times with three 150 mL portions of dichloromethane. The organic layer was dried with MgSO$_4$, and the solvent was removed by evaporation. The residue was recrystallized with dichloromethane and methanol to obtain 15.3 g of Intermediate D (yield: 75%). The product was confirmed by using LC-MS and HPLC.

LC-MS (m/z)=C$_{30}$H$_{26}$BNO$_2$S (M$^+$) 475.

3) Synthesis of Compound 11

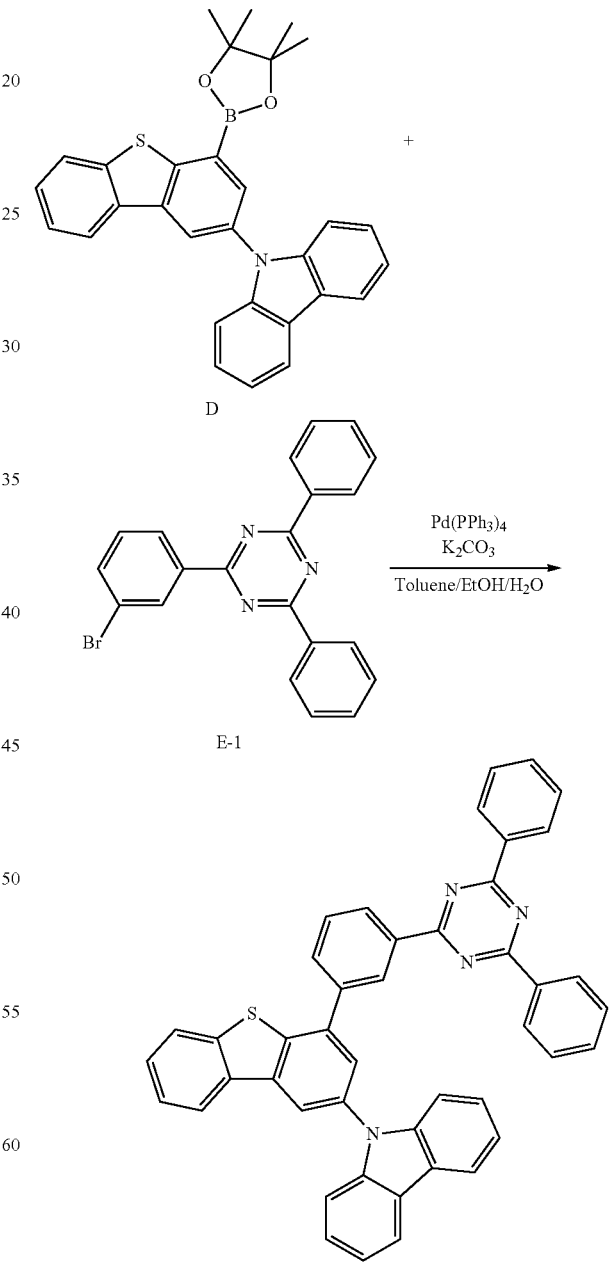

5.00 g (10.5 mmol) of Intermediate D, 4.07 g (10.5 mmol) of Compound E-1, 0.61 g (0.53 mmol) of Pd(PPh$_3$)$_4$, and 7.26 g (52.6 mmol) of K$_2$CO$_3$ were dissolved in 200 mL of toluene, 40 mL of ethanol, and 60 mL of distilled water, and stirred under reflux at 120° C. for 18 hours. The result was allowed to come to room temperature. 100 mL of distilled water was added, and the mixture was stirred. A solid was formed and the solid was filtered. The residue was recrystallized with toluene and methanol to obtain 5.34 g of Compound 11 (yield: 77%). The product was confirmed by using LC-MS and HPLC.

LC-MS (m/z)=C$_{45}$H$_{28}$N$_4$S (M$^+$) 656.

Synthesis Example 12: Synthesis of Compound 12

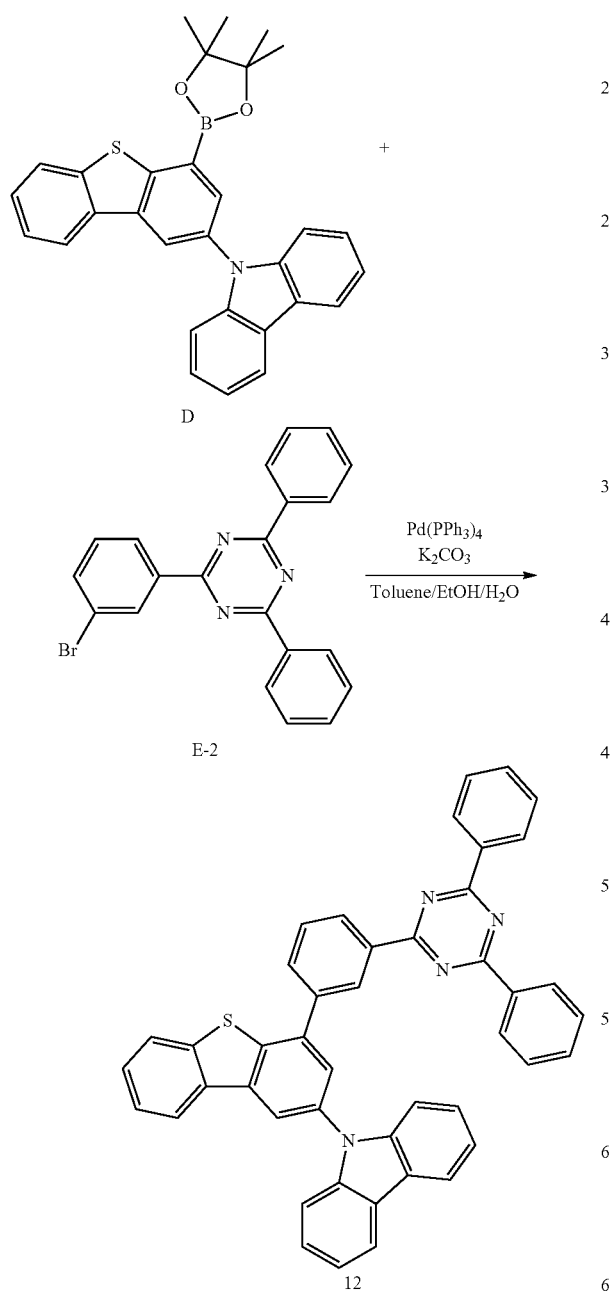

5.30 g of Compound 12 (yield: 77%) was obtained in the same manner as in Synthesis Example 11 except that 4.07 g (10.5 mmol) of Compound E-2 was used instead of 4.07 g (10.5 mmol) of Compound E-1. The product was confirmed by LC-MS and HPLC.

LC-MS (m/z)=C$_{46}$H$_{29}$N$_3$S (M$^+$) 655.

Synthesis Example 13: Synthesis of Compound 13

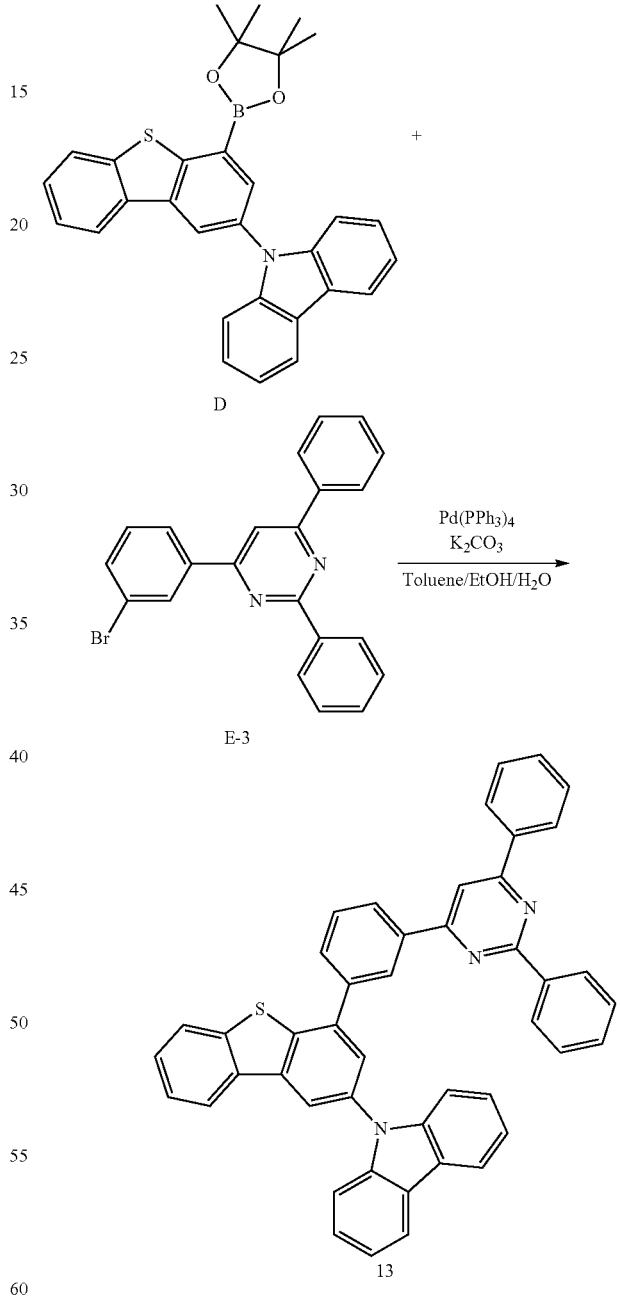

4.86 g of Compound 13 (yield: 64%) was obtained in the same manner as in Synthesis Example 11 except that 4.07 g (10.5 mmol) of Compound E-3 was used instead of 4.07 g (10.5 mmol) of Compound E-1. The product was confirmed by using LC-MS and HPLC.

LC-MS (m/z)=C$_{46}$H$_{29}$N$_3$S (M$^+$) 655.

Synthesis Example 14: Synthesis of Compound 14

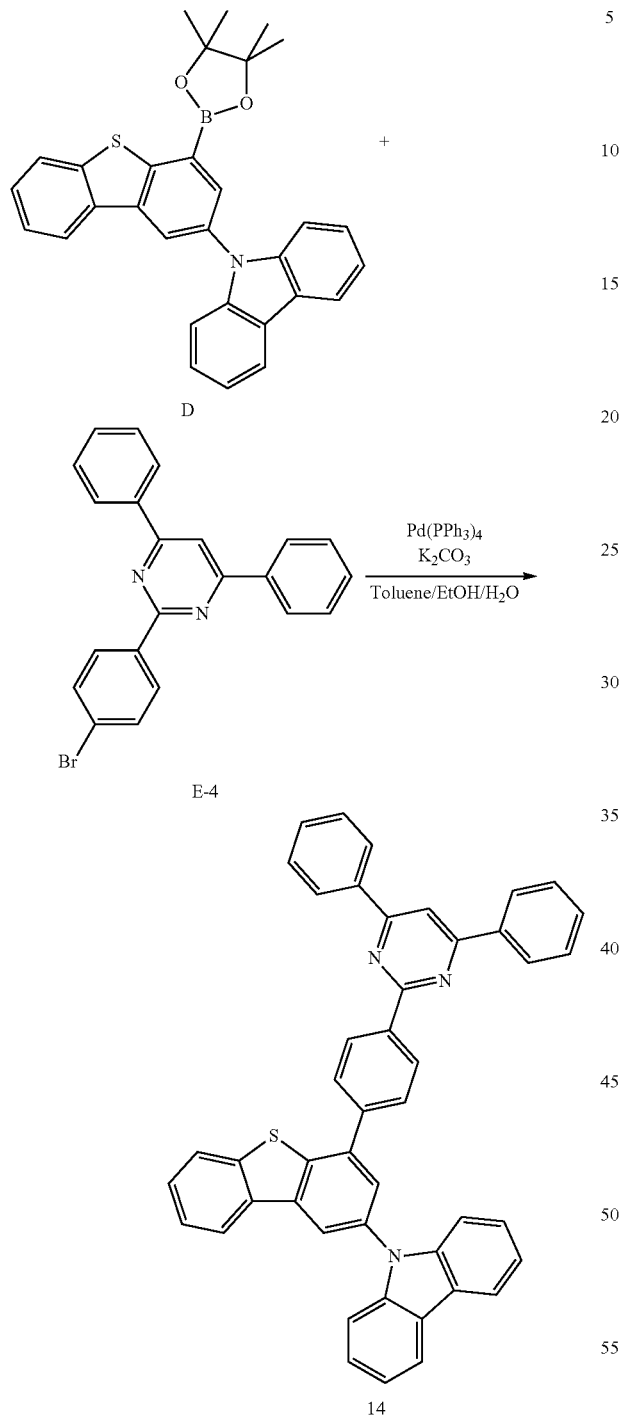

Synthesis Example 15: Synthesis of Compound 15

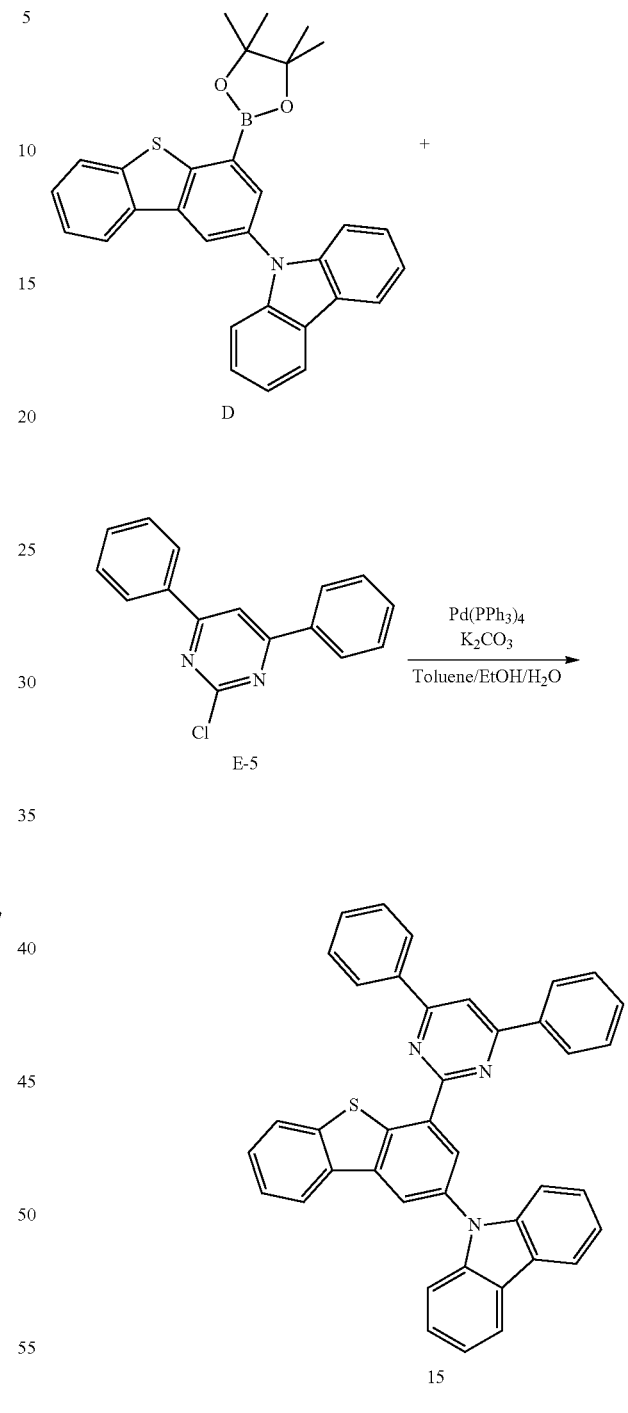

5.16 g of Compound 14 (yield: 75%) was obtained in the same manner as in Synthesis Example 11 except that 4.07 g (10.5 mmol) of Compound E-4 was used instead of 4.07 g (10.5 mmol) of Compound E-1. The product was confirmed by using LC-MS and HPLC.

LC-MS (m/z)=$C_{46}H_{29}N_3S$ (M+) 655.

4.44 g of Compound 15 (yield: 73%) was obtained in the same manner as in Synthesis Example 11 except that 2.80 g (10.5 mmol) of Compound E-5 was used instead of 4.07 g (10.5 mmol) of Compound E-1. The product was confirmed by using LC-MS and HPLC.

LC-MS (m/z)=$C_{40}H_{25}N_3S$ (M+) 579.

Synthesis Example 16: Synthesis of Compound 16

Synthesis Example 17: Synthesis of Compound 17

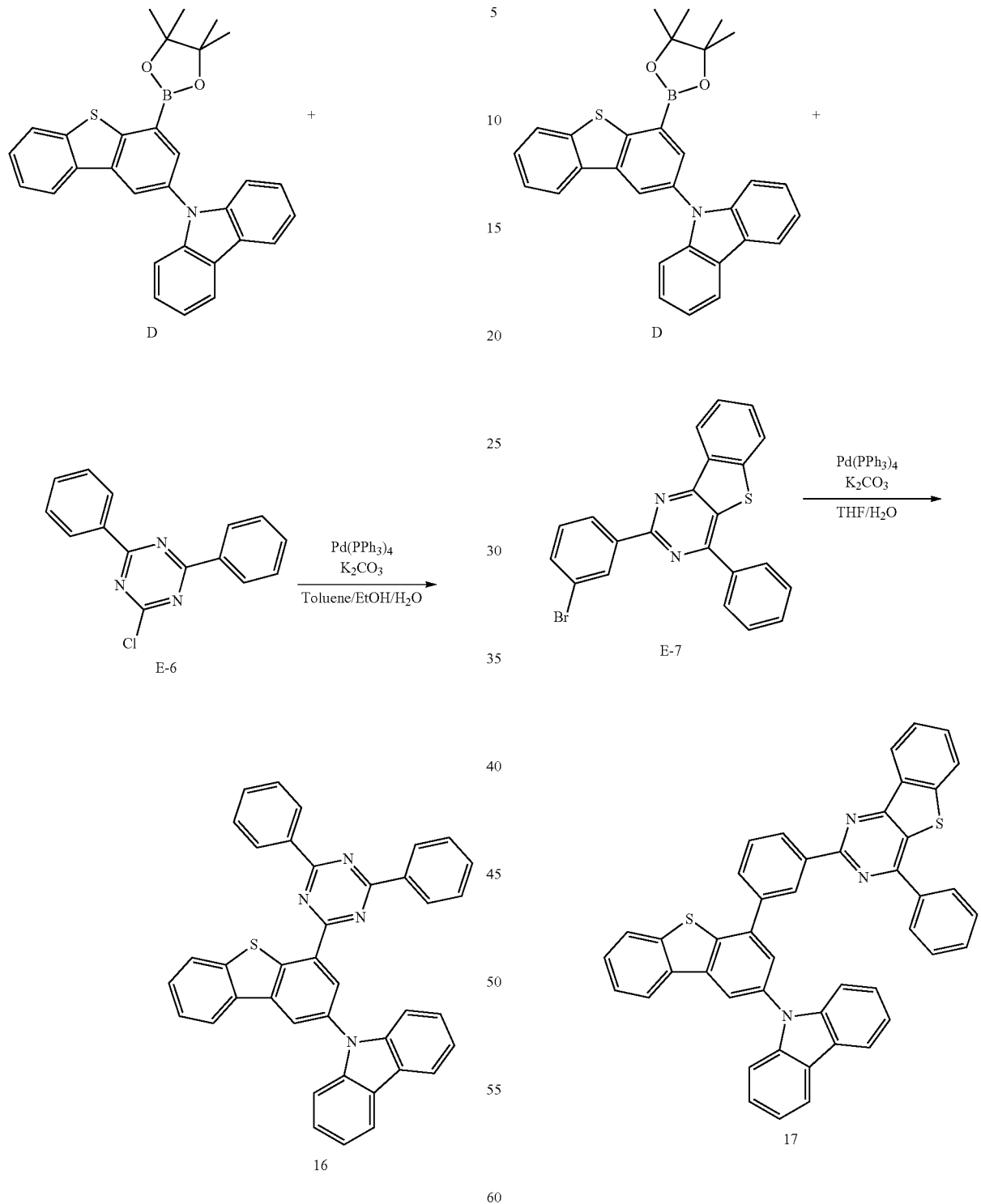

4.15 g of Compound 16 (yield: 68%) was obtained in the same manner as in Synthesis Example 11 except that 2.81 g (10.5 mmol) of Compound E-6 was used instead of 4.07 g (10.5 mmol) of Compound E-1. The product was confirmed by using LC-MS and HPLC.

LC-MS (m/z)=$C_{39}H_{24}N_4S$ ($M^+$) 580.

5.76 g of Compound 17 (yield: 80%) was obtained in the same manner as in Synthesis Example 11 except that 4.38 g (10.5 mmol) of Compound E-7 was used instead of 4.07 g (10.5 mmol) of Compound E-1. The product was confirmed by using LC-MS and HPLC.

LC-MS (m/z)=$C_{46}H_{27}N_3S$ ($M^+$) 685.

Synthesis Example 18: Synthesis of Compound 18

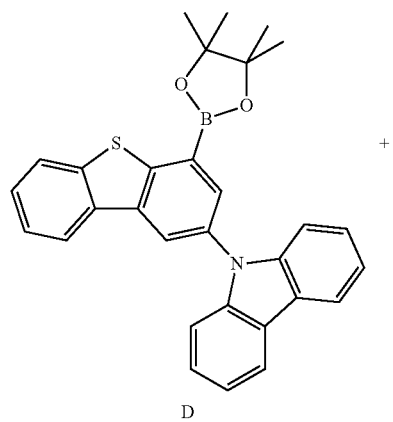

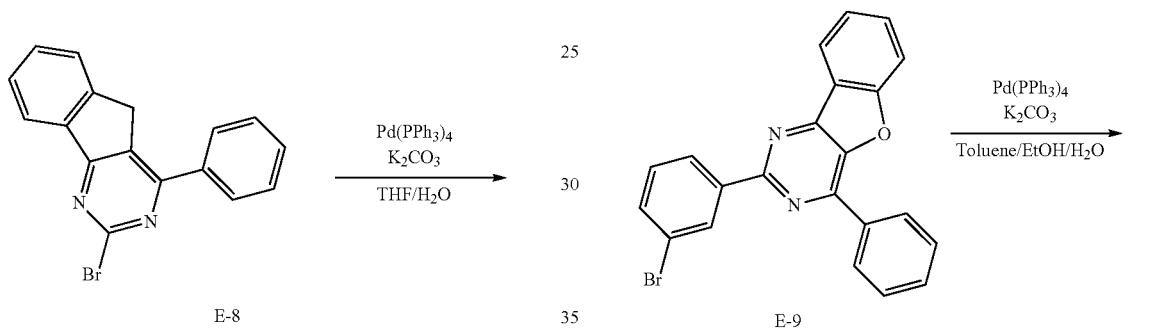

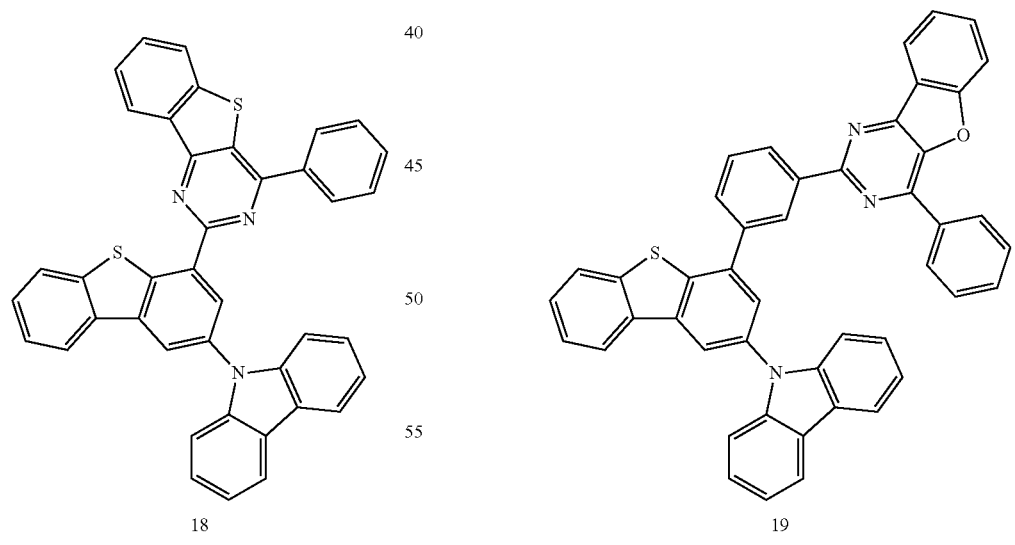

Synthesis Example 19: Synthesis of Compound 19

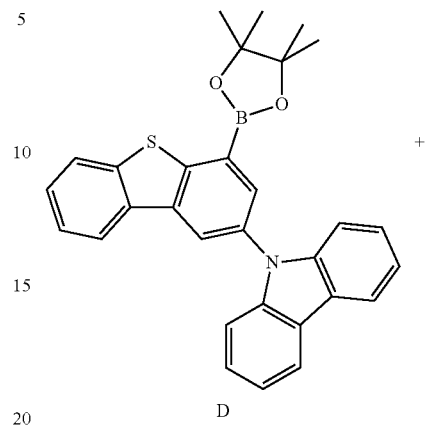

4.74 g of Compound 18 (yield: 74%) was obtained in the same manner as in Synthesis Example 11 except that 3.58 g (10.5 mmol) of Compound E-8 was used instead of 4.07 g (10.5 mmol) of Compound E-1. The product was confirmed by using LC-MS and HPLC.

LC-MS (m/z)=$C_{40}H_{23}N_3S_2$ (M$^+$) 609.

4.99 g of Compound 19 (yield: 71%) was obtained in the same manner as in Synthesis Example 11 except that 4.21 g (10.5 mmol) of Compound E-9 was used instead of 4.07 g (10.5 mmol) of Compound E-1. The product was confirmed by using LC-MS and HPLC.

LC-MS (m/z)=$C_{46}H_{27}N_3S$ (M$^+$) 669.

Synthesis Example 20: Synthesis of Compound 20

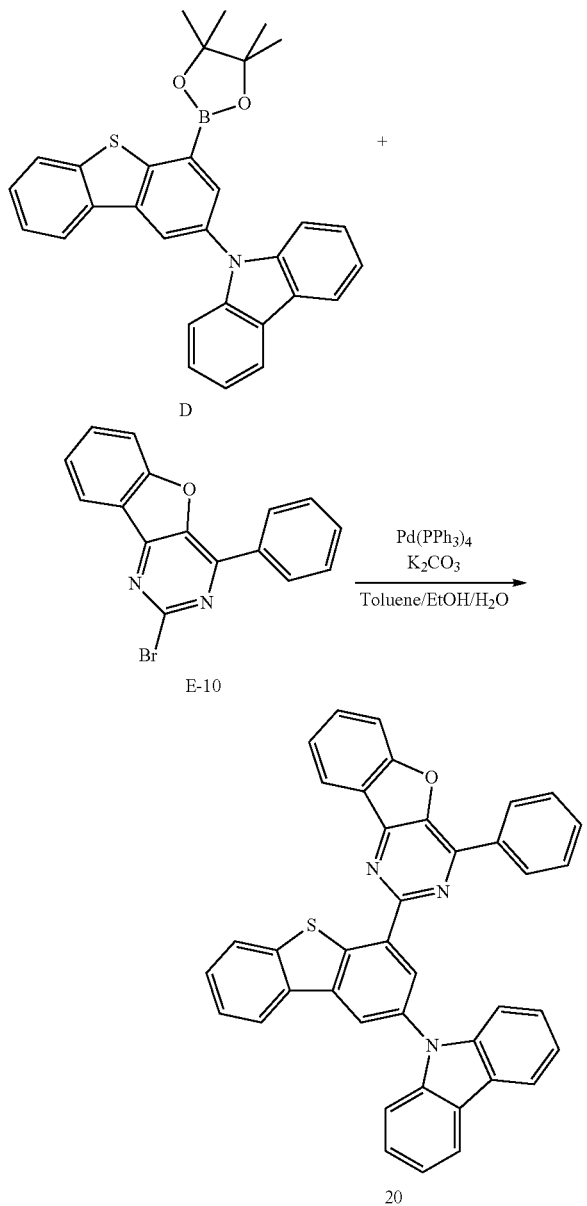

4.18 g of Compound 20 (yield: 67%) was obtained in the same manner as in Synthesis Example 11 except that 3.41 g (10.5 mmol) of Compound E-10 was used instead of 4.07 g (10.5 mmol) of Compound E-1. The product was confirmed by using LC-MS and HPLC.

LC-MS (m/z)=$C_{40}H_{23}N_3OS$ (M$^+$) 593.

Evaluation Example 1: Evaluation on HOMO, LUMO and Triplets (T1) Energy Levels HOMO, LUMO, and T1 energy levels of Compounds 1, 2, 5 to 8, and 11 to 15 were evaluated according to the method indicated in Table 2, and results thereof are shown in Table 3.

TABLE 2

| | |
|---|---|
| HOMO energy level evaluation method | A potential (Volts, V)-current (Amperes, A) graph of each compound was obtained by using cyclic voltammetry (CV) (electrolyte: 0.1M Bu$_4$NClO$_4$/solvent: CH$_2$Cl$_2$/electrode: 3 electrode system (working electrode: GC, reference electrode: Ag/AgCl, auxiliary electrode: Pt)). From reduction onset of the graph, a HOMO energy level of the compound was calculated. |
| LUMO energy level evaluation method | Each compound was diluted at a concentration of 1 × 10$^{-5}$ M in CHCl$_3$, and an UV absorption spectrum thereof was measured at room temperature by using a Shimadzu UV-350 spectrometer. The LUMO energy level thereof was calculated by using an optical band gap (Eg) from an edge of the absorption spectrum. |
| T1 energy level evaluation method | A mixture (each compound was dissolved in an amount of 1 milligram (mg) in 3 cubic centimeters (cc) of toluene) of toluene and each compound was loaded into a quartz cell. The resultant quartz cell was loaded into liquid nitrogen (77 Kelvins (K)) and a photoluminescence spectrum thereof was measured by using a device for measuring photoluminescence. The obtained spectrum was compared with a photoluminescence spectrum measured at room temperature. The peaks observed only at low temperature were analyzed to calculate T1 energy levels. |

TABLE 3

| Compound No. | HOMO (eV) (calc.) | LUMO (eV) (calc.) | T1 energy level (eV) |
|---|---|---|---|
| 1 | −5.68 | −2.30 | 2.81 |
| 2 | −5.60 | −2.14 | 2.83 |
| 5 | −5.66 | −2.41 | 2.74 |
| 6 | −5.66 | −2.61 | 2.62 |
| 7 | −5.65 | −2.31 | 2.68 |
| 8 | −5.64 | −2.38 | 2.63 |
| 11 | −5.65 | −2.19 | 2.60 |
| 12 | −5.62 | −2.16 | 2.66 |
| 13 | −5.60 | −2.44 | 2.66 |

From Table 3, it is confirmed that the Compounds 1, 2, 5 to 8, and 11 to 15 have electric characteristics that are suitable for use as a material for forming an organic light-emitting device.

Evaluation Example 2: Thermal Characteristics Evaluation

Thermal analysis (N$_2$ atmosphere, temperature range: from room temperature to 800° C. (10° C./min)-TGA, from room temperature to 400° C.-DSC, Pan Type: Pt Pan in disposable Al Pan(TGA), and disposable Al pan(DSC)) was performed on Compounds 1, 2, 5 to 8, and 11 to 15 by using thermogravimetric analysis (TGA) and differential scanning calorimetry (DSC). The evaluation results are shown in Table 4. As shown in Table 4, it was confirmed that the compounds had excellent thermal stability.

TABLE 4

| Compound No. | Tg (° C.) | Tm (° C.) | Tc (° C.) | Td (1%/5%, ° C.) |
|---|---|---|---|---|
| 1 | 142.98 | 285.79 | n/a | 409.56/444.65 |
| 2 | 138.18 | 280.71 | n/a | 410.67/445.37 |
| 5 | 117.14 | 283.97 | n/a | 375.88/409.68 |
| 6 | 120.13 | 328.07 | n/a | 366.20/403.62 |
| 7 | 153.20 | 287.12 | n/a | 432.83/465.97 |
| 8 | 136.66 | 311.78 | n/a | 394.21/433.56 |
| 11 | 151.10 | 294.16 | n/a | 409.91/449.60 |
| 12 | 146.10 | 243.26 | n/a | 421.37/457.01 |

TABLE 4-continued

| Compound No. | Tg (° C.) | Tm (° C.) | Tc (° C.) | Td (1%/5%, ° C.) |
|---|---|---|---|---|
| 13 | 144.75 | 251.05 | n/a | 431.07/471.64 |
| 14 | 155.73 | n/a | n/a | 433.87/472.40 |
| 15 | 131.31 | 296.57 | n/a | 393.04/428.96 |

Evaluation Example 3: Emission Spectrum Evaluation

Photoluminescence (PL) spectrum of Compounds 1, 2, 5 to 8, and 11 to 15 were measured to evaluate emission characteristics of each compound. Compound 1 was dissolved at a concentration of 10 millimolar (mM). ISC PC1 spectrofluorometer in which a Xenon lamp was mounted was used to measure a PL spectrum (@ 298 K) of Compound 1. The same process was repeated for Compounds 2, 5 to 8, and 11 to 15.

Maximum wavelength of PL spectra of Compound 1, 2, 5 to 8, and 11 to 15 are shown in Table 5.

TABLE 5

| Compound No. | λmax (nm) |
|---|---|
| 1 | 392 |
| 2 | 385 |
| 5 | 412 |
| 6 | 445 |
| 7 | 392 |
| 8 | 415 |
| 11 | 403 |
| 12 | 385 |
| 13 | 391 |
| 14 | 406 |
| 15 | 422 |

From Table 5, it is confirmed that the Compounds 1, 2, 5 to 8, and 11 to 15 have excellent emission characteristics.

Example 1

As a first electrode (an anode), a glass substrate having indium tin oxide (ITO) electrode deposited thereon at a thickness of 1,500 Å was washed with distilled water under sonication with ultrasound waves. When the washing with distilled water was completed, ultrasound wave washing was performed on the substrate by using a solute such as isopropyl alcohol, acetone, or methanol. The substrate was then dried, transferred to a plasma washer to wash for 5 minutes using an oxygen plasma, and then mounted in a vacuum depositor.

Then, 4,4'-bis[N-(1-naphthyl)-N-phenylamino]biphenyl (NPB) was vacuum deposited on the ITO electrode on the glass substrate to form a hole transport layer having a thickness of 1,200 Å, thereby forming a hole transport region.

Compound 1 (a host) and 10 percent by weight (wt %) Ir(ppy)$_3$ (a dopant) (referred to as Compound PD1 herein) were co-deposited on the hole transport region to form an emission layer having a thickness of 300 Å.

BAlq was vacuum deposited on the emission layer to form a first electron transport layer having a thickness of 50 Å, Alq3 was deposited on the first electron transport layer to form a second electron transport layer having a thickness of 250 Å, LiF was vacuum-deposited on the second electron transport layer to form an electron injection layer having a thickness of 5 Å, and an Al second electrode (a cathode) having a thickness of 1,000 Å was formed on the electron injection layer, thereby completing manufacturing of an organic light-emitting device.

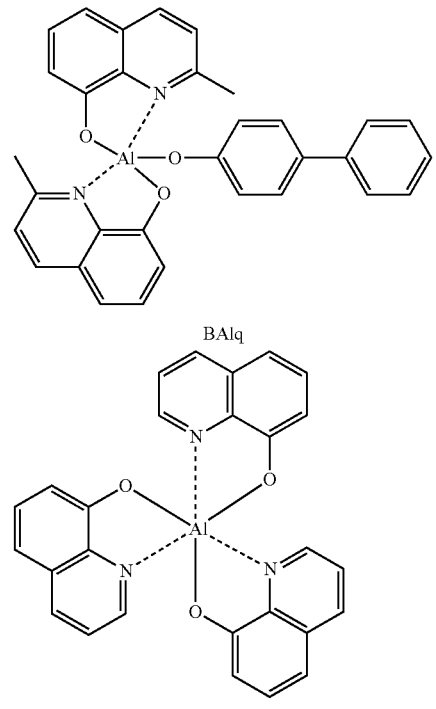

Example 2

An organic light-emitting device was manufactured in the same manner as in Example 1, except that Compound 2 was used instead of Compound 1 as a host in the formation of the emission layer.

Example 3

An organic light-emitting device was manufactured in the same manner as in Example 1, except that Compound 5 was used instead of Compound 1 as a host in the formation of the emission layer.

Example 4

An organic light-emitting device was manufactured in the same manner as in Example 1, except that Compound 6 was used instead of Compound 1 as a host in the formation of the emission layer.

Example 5

An organic light-emitting device was manufactured in the same manner as in Example 1, except that Compound 7 was used instead of Compound 1 as a host in the formation of the emission layer.

Example 6

An organic light-emitting device was manufactured in the same manner as in Example 1, except that Compound 8 was used instead of Compound 1 as a host in the formation of the emission layer.

Example 7

An organic light-emitting device was manufactured in the same manner as in Example 1, except that Compound 11 was used instead of Compound 1 as a host in the formation of the emission layer.

Example 8

An organic light-emitting device was manufactured in the same manner as in Example 1, except that Compound 12 was used instead of Compound 1 as a host in the formation of the emission layer.

Example 9

An organic light-emitting device was manufactured in the same manner as in Example 1, except that Compound 13 was used instead of Compound 1 as a host in the formation of the emission layer.

Example 10

An organic light-emitting device was manufactured in the same manner as in Example 1, except that Compound 14 was used instead of Compound 1 as a host in the formation of the emission layer.

Example 11

An organic light-emitting device was manufactured in the same manner as in Example 1, except that Compound 15 was used instead of Compound 1 as a host in the formation of the emission layer.

Comparative Example 1

An organic light-emitting device was manufactured in the same manner as in Example 1, except that Compound A was used instead of Compound 1 as a host in the formation of the emission layer.

Compound A

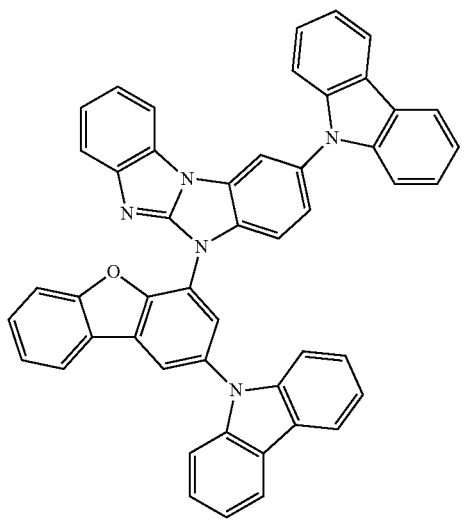

Comparative Example 2

An organic light-emitting device was manufactured in the same manner as in Example 1, except that Compound B was used instead of Compound 1 as a host in the formation of the emission layer.

Compound B

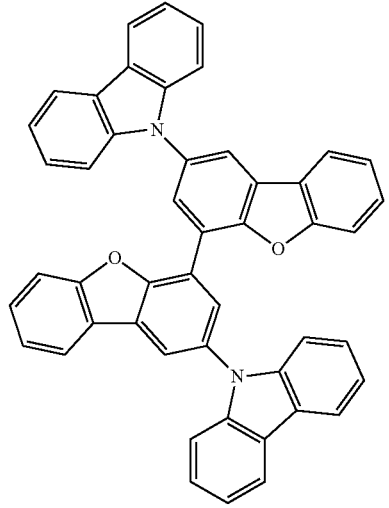

Comparative Example 3

An organic light-emitting device was manufactured in the same manner as in Example 1, except that CBP was used instead of Compound 1 as a host in the formation of the emission layer.

Evaluation Example 4: Evaluation of Characteristics of Organic Light-Emitting Device Current density changes, luminance changes, and emission efficiencies of the organic light-emitting device prepared in Examples 1 to 11 and Comparative Examples 1 and 2 were measured by various applied voltages. Detailed measurement method is as described below, and the result thereof are shown in Table 6:

(1) Measurement of Current Density Changes According to Applied Voltages

Current values of the organic light-emitting devices prepared in Examples 1 to 11 and Comparative Examples 1 and 2 were measured by measuring values of current in a unit device thereof using a current voltmeter (Keithley 2400) while increasing the applied voltage from about 0 Volts (V) to about 10 V. The result was obtained by dividing a current value by an area.

(2) Measurement of Luminance Changes Depending on Changes of Applied Voltages

Luminance values of the organic light-emitting devices prepared in Examples 1 to 11 and Comparative Examples 1 and 2 were measured by using a luminance meter (Minolta Cs-1000A) while increasing the applied voltage from about 0 V to about 10 V.

(3) Measurement of Emission Efficiencies

The luminance values measured from (2) and current density values measured from (1), and applied voltages were used in calculating current efficiencies (candelas per Ampere (cd/A)) in a condition of an identical current density (10 milliAmperes per square centimeter ($mA/cm^2$)).

TABLE 6

| | EML | | Driving voltage | Efficiency | Power | Emission |
|---|---|---|---|---|---|---|
| | Host | Dopant | (V) | (cd/A) | (lm/W) | color |
| Example 1 | Compound 1 | Ir(ppy)$_3$ | 5.4 | 50 | 29.1 | Green |
| Example 2 | Compound 2 | Ir(ppy)$_3$ | 5.5 | 53 | 30.3 | Green |
| Example 3 | Compound 5 | Ir(ppy)$_3$ | 5.0 | 60.5 | 38.0 | Green |
| Example 4 | Compound 6 | Ir(ppy)$_3$ | 5.3 | 53.3 | 31.6 | Green |
| Example 5 | Compound 7 | Ir(ppy)$_3$ | 5.5 | 52.4 | 29.9 | Green |
| Example 6 | Compound 8 | Ir(ppy)$_3$ | 5.5 | 57.3 | 32.7 | Green |
| Example 7 | Compound 11 | Ir(ppy)$_3$ | 5.5 | 34.1 | 19.5 | Green |
| Example 8 | Compound 12 | Ir(ppy)$_3$ | 5.9 | 35.3 | 18.8 | Green |
| Example 9 | Compound 13 | Ir(ppy)$_3$ | 6.4 | 43.4 | 21.3 | Green |
| Example 10 | Compound 14 | Ir(ppy)$_3$ | 5.9 | 47.7 | 25.4 | Green |
| Example 11 | Compound 15 | Ir(ppy)$_3$ | 4.5 | 51.1 | 35.7 | Green |
| Comparative Example 1 | Compound A | Ir(ppy)$_3$ | 5.2 | 44.5 | 26.9 | Green |
| Comparative Example 2 | Compound B | Ir(ppy)$_3$ | 5.1 | 46 | 28.3 | Green |
| Comparative Example 3 | CBP | Ir(ppy)$_3$ | 6.5 | 47.7 | 22.0 | Green |

According to Table 6, the organic light-emitting devices prepared in Examples 1 to 11 have low driving voltages and high efficiencies compared to the organic light-emitting devices prepared in Comparative Examples 1 to 3.

As described above, according to the one or more of the above exemplary embodiments, the carbazole compound has excellent electric characteristics and thermal stability. Accordingly, an organic light-emitting device including the carbazole compound may have excellent power consumption, efficiency, luminance, and lifespan characteristics.

It should be understood that the exemplary embodiments described therein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope as defined by the following claims.

What is claimed is:

1. A carbazole compound represented by Formula 1:

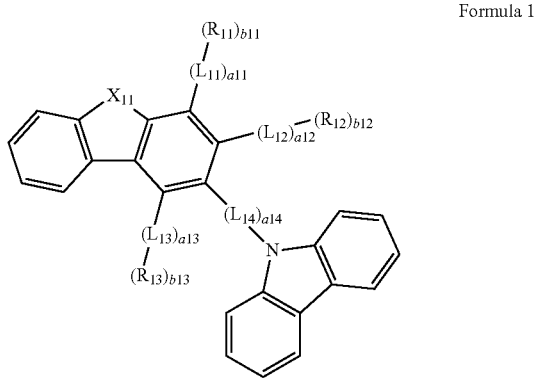

Formula 1 wherein in Formula 1, $X_{11}$ is selected from O and S;

$L_{11}$ to $L_{14}$ are each independently selected from a substituted or unsubstituted $C_1$-$C_{60}$ alkylene group, a substituted or unsubstituted $C_2$-$C_{60}$ alkenylene group, a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, and a substituted or unsubstituted $C_1$-$C_{60}$ heteroarylene group;

a11 to a14 are each independently selected from 0, 1, 2, 3, 4, and 5;

$R_{11}$ to $R_{13}$ are each independently selected from $R_{ET}$, a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof; and —Si($Q_3$)($Q_4$)($Q_5$);

wherein $Q_3$ to $Q_5$ are each independently selected from a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, and a quinoxalinyl group;

at least one selected from $R_{11}$ to $R_{13}$ is $R_{ET}$;

b11 to b13 are each independently selected from 1, 2, 3, and 4; and $R_{ET}$ is selected from Formulae 9-1 to 9-52:
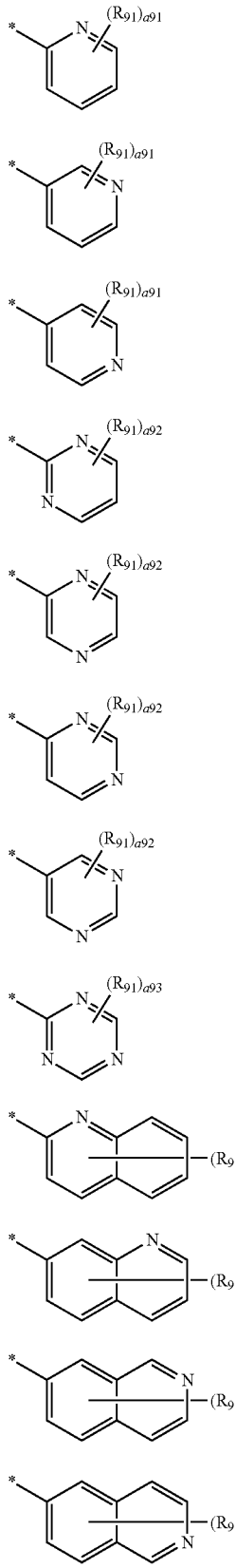
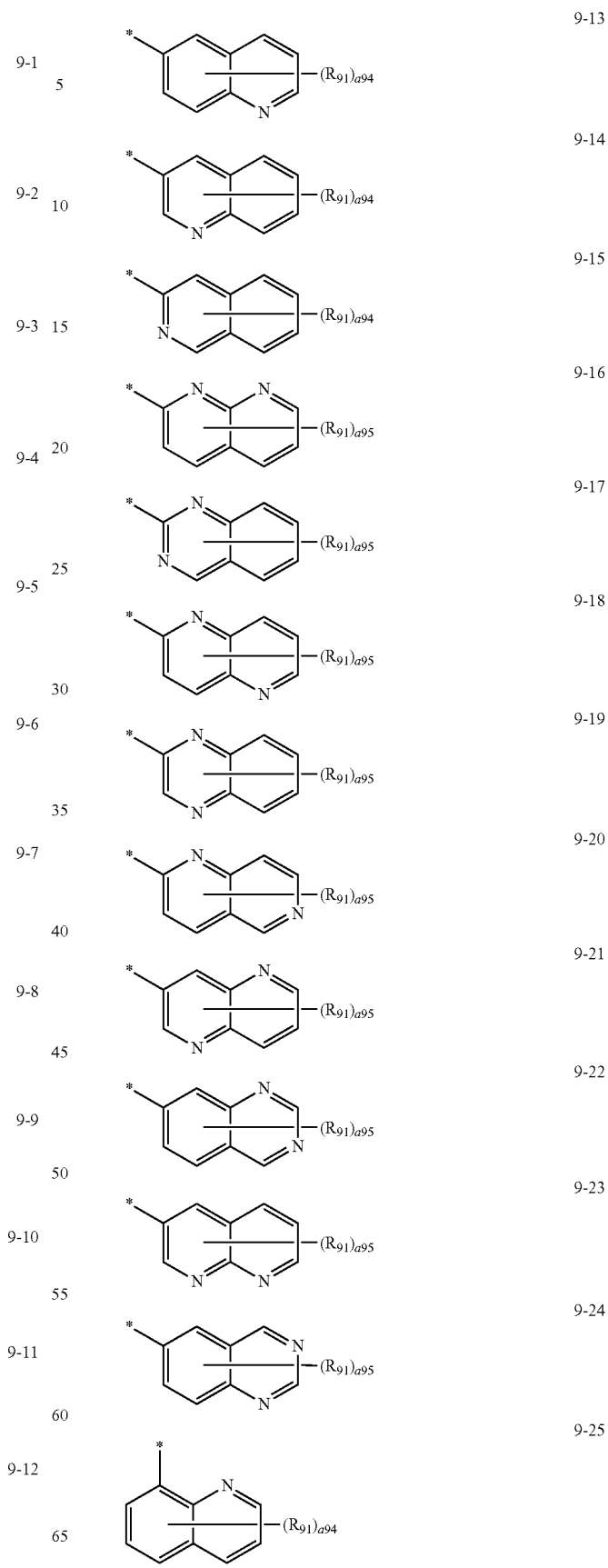

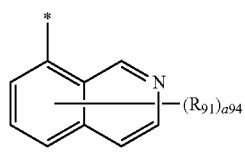
9-26
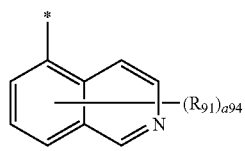
9-27
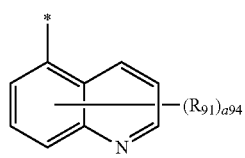
9-28
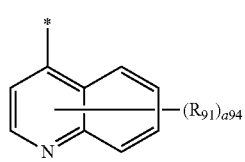
9-29
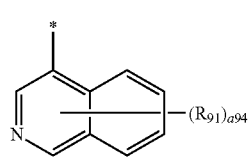
9-30
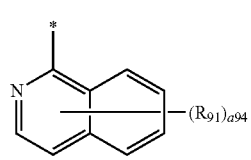
9-31
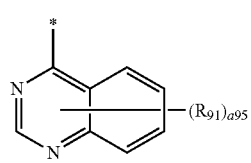
9-32
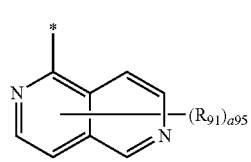
9-33
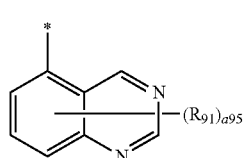
9-34
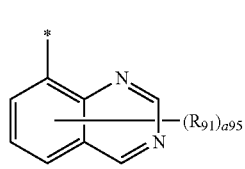
9-35
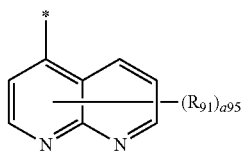
9-36
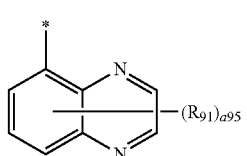
9-37
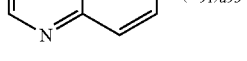
9-38
9-39
9-40
9-41
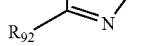
9-42
9-43
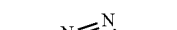
9-44
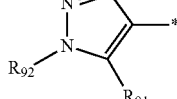
9-45

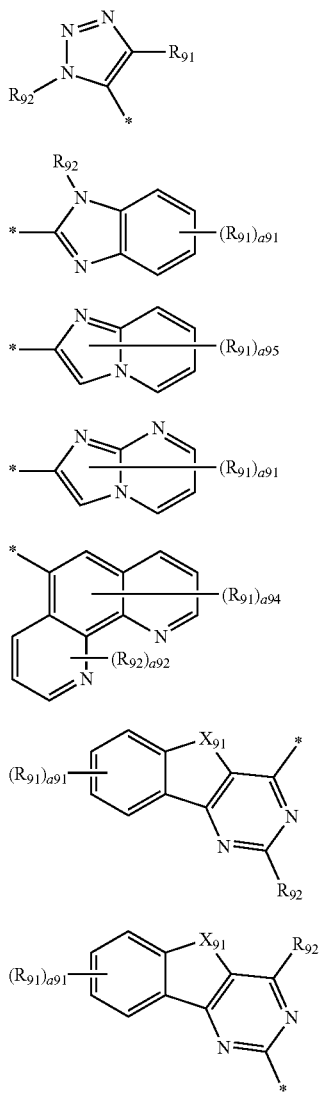

wherein in Formulae 9-1 to 9-52,
$X_{91}$ is selected from O and S;
$R_{91}$ and $R_{92}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_1$-$C_{60}$ alkoxy group, a $C_6$-$C_{60}$ aryl group, a $C_6$-$C_{60}$ aryloxy group, a $C_6$-$C_{60}$ arylthio group, and a $C_1$-$C_{60}$ heteroaryl group;
a91 is selected from 1, 2, 3, and 4;
a92 is selected from 1, 2, and 3;
a93 is selected from 1 and 2;
a94 is selected from 1, 2, 3, 4, 5, and 6; and
a95 is selected from 1, 2, 3, 4, and 5;
* indicates a binding site to a neighboring atom;
at least one substituent of the substituted $C_1$-$C_{60}$ alkylene group, substituted $C_2$-$C_{60}$ alkenylene group, substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group is selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;
a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), and —B($Q_{16}$)($Q_{17}$);
a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;
a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), and —B($Q_{26}$)($Q_{27}$); and
—N($Q_{31}$)($Q_{32}$), —Si($Q_{33}$)($Q_{34}$)($Q_{35}$), and —B($Q_{36}$)($Q_{37}$);
wherein $Q_{11}$ to $Q_{17}$, $Q_{21}$ to $Q_{27}$, and $Q_{31}$ to $Q_{37}$ are each independently selected from a hydrogen, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.
2. The carbazole compound of claim 1, wherein $L_{11}$ to $L_{14}$ are each independently selected from Formulae 2-1 to 2-28:
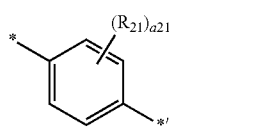
2-1
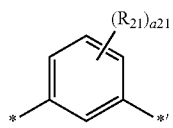
2-2
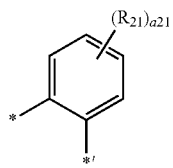
2-3
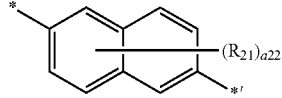
2-4
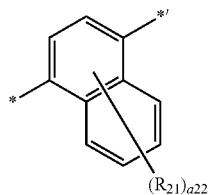
2-5
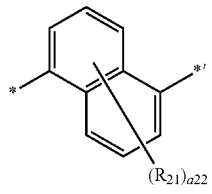
2-6
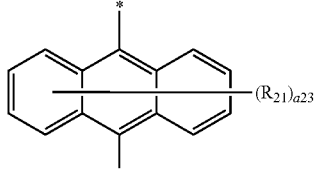
2-7
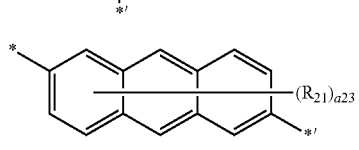
2-8
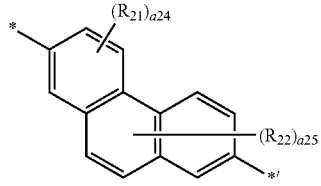
2-9
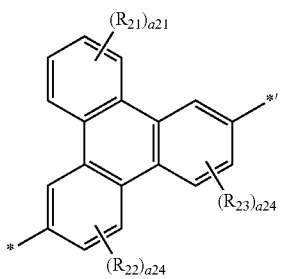
2-10
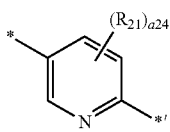
2-11
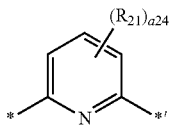
2-12
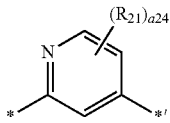
2-13
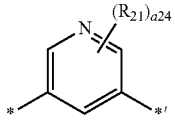
2-14
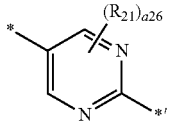
2-15
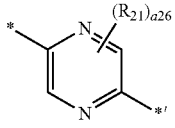
2-16
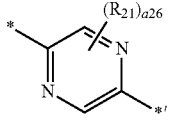
2-17
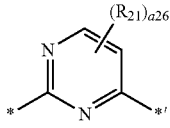
2-18
2-19

2-20 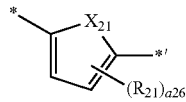

2-21 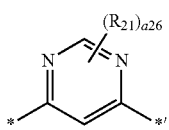

2-22 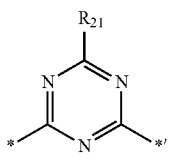

2-23 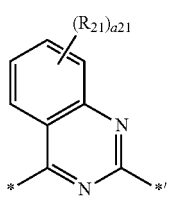

2-24 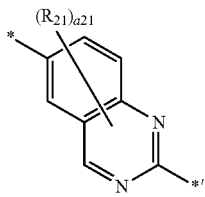

2-25 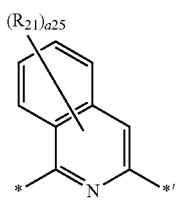

2-26 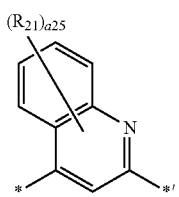

2-27 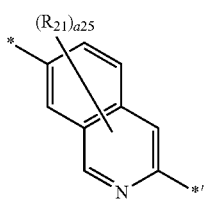

2-28 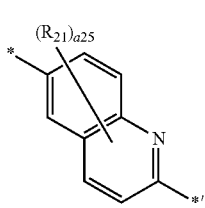

wherein in Formulae 2-1 to 2-28, $X_{21}$ is selected from O and S;

$R_{21}$ to $R_{23}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a phenyl group-substituted with a phenyl group, a naphthyl group, an anthracenyl group, a triphenylenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, a quinoxalinyl group, and —Si($Q_{33}$)($Q_{34}$)($Q_{45}$);

wherein $Q_{33}$ to $Q_{45}$ are each independently selected from a hydrogen, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group a phthalazinyl group, a quinoxalinyl group, a cinnolinyl group, and a quinazolinyl group;

a21 is selected from 1, 2, 3, and 4;

a22 is selected from 1, 2, 3, 4, 5, and 6;

a23 is selected from 1, 2, 3, 4, 5, 6, 7, and 8;

a24 is selected from 1, 2, and 3;

a25 is selected from 1, 2, 3, 4, and 5;

a26 is selected from 1 and 2; and

* and *' each independently indicates a binding site to a neighboring atom.

3. The carbazole compound of claim 1, wherein $L_{11}$ to $L_{14}$ are each independently selected from Formulae 3-1 to 3-14:

3-1 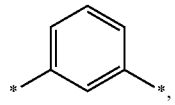

3-2 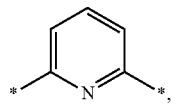

3-3 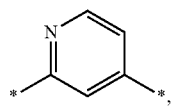

-continued 3-4
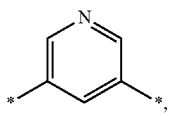

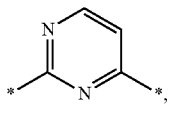
3-5

3-6
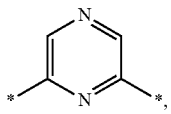

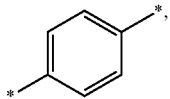
3-14 wherein in Formulae 3-1 to 3-14,
* and *' each independently indicates a binding site to a neighboring atom.

4. The carbazole compound of claim 1, wherein a11 to a13 are each independently selected from 0 and 1.

5. The carbazole compound of claim 1, wherein a 14 is 0.

6. The carbazole compound of claim 1, wherein
at least one selected from $R_{11}$ to $R_{13}$ are each independently selected from Formulae 9-1 to 9-52:

3-7
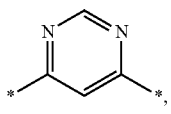

3-8
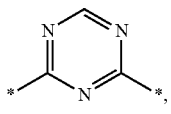

3-9
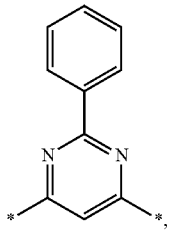

3-10
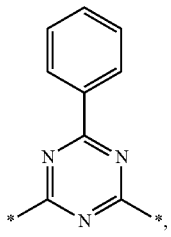

3-11
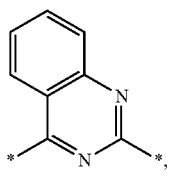

3-12
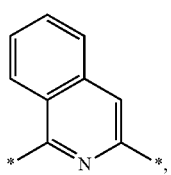

3-13
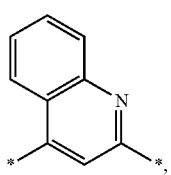

9-1
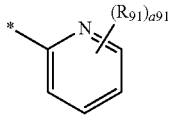

9-2
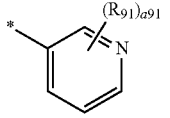

9-3
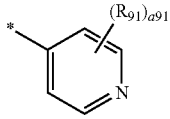

9-4
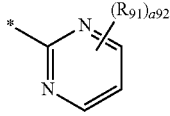

9-5
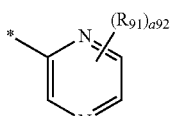

9-6
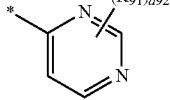

9-7
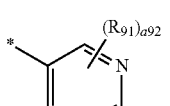

9-8
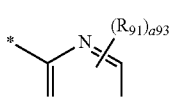

9-9
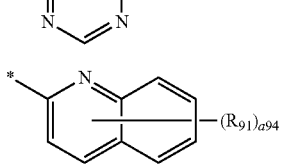

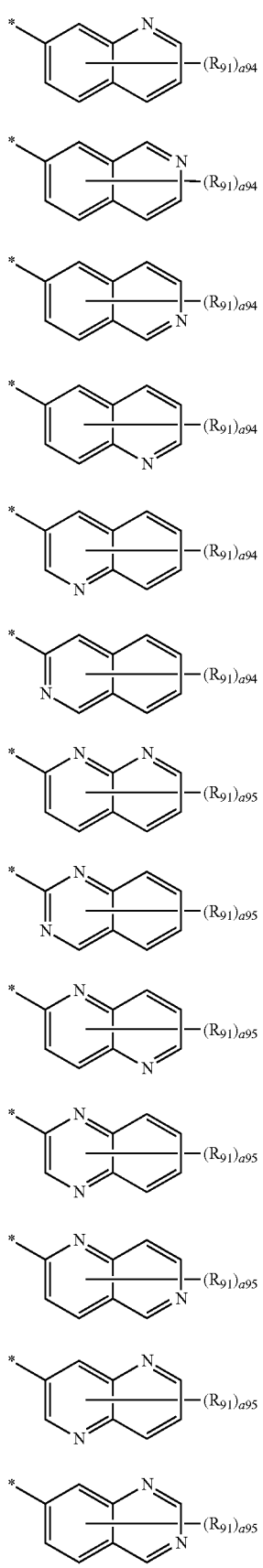
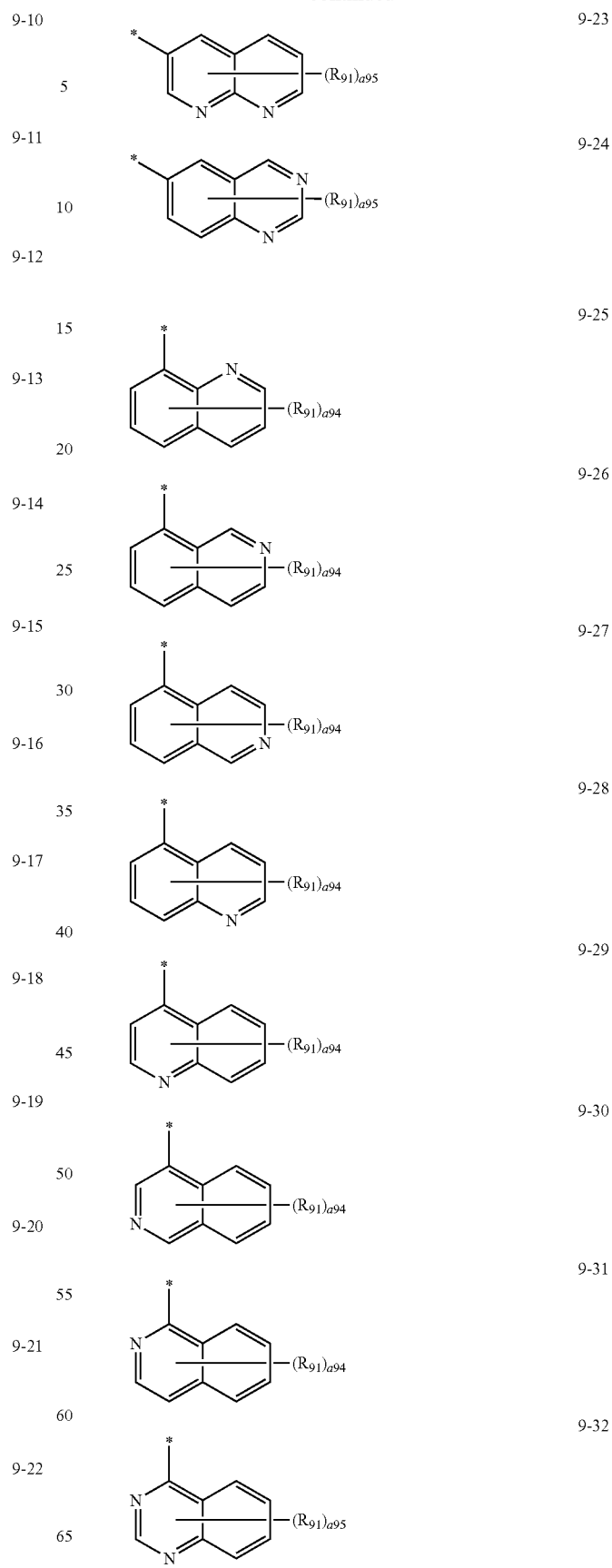

-continued
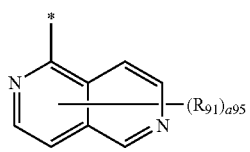 9-33
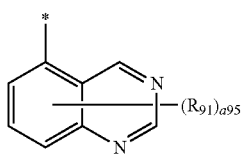 9-34
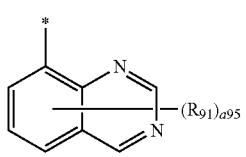 9-35
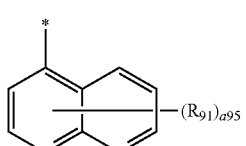 9-36
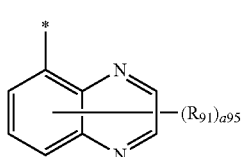 9-37
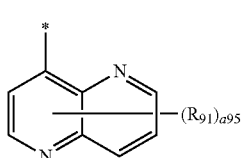 9-38
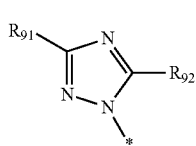 9-39
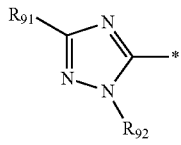 9-40
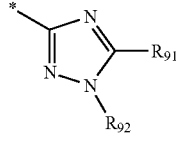 9-41
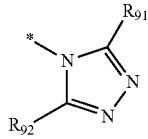 9-42
-continued
9-43
9-44
9-45
9-46
9-47
9-48
9-49
9-50
9-51
9-52
wherein in Formulae 9-1 to 9-52,
$X_{91}$ is selected from O and S;
$R_{91}$ and $R_{92}$ are each independently selected from a hydrogen, a deuterium, —F, —Cl, —Br, —I, a cyano group, a nitro group, a $C_1$-$C_{20}$ alkyl group, a $C_1$-$C_{20}$ alkoxy group, a phenyl group, a biphenyl group, a naphthyl group, an anthracenyl group, a pyrenyl group, a phenanthrenyl group, a pyridinyl group, a pyrimidinyl group, a triazinyl group, a quinolinyl group, an isoquinolinyl group, and a quinazolinyl group;
a91 is selected from 1, 2, 3, and 4;
a92 is selected from 1, 2, and 3;
a93 is selected from 1 and 2;
a94 is selected from 1, 2, 3, 4, 5, and 6;
a95 is selected from 1, 2, 3, 4, and 5; and
* indicates a binding site to a neighboring atom.

7. The carbazole compound of claim 1, wherein
at least one selected from $R_{11}$ to $R_{13}$ is each independently selected from Formulae 9-4 to 9-8, 9-51, and 9-52:

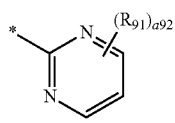

9-4

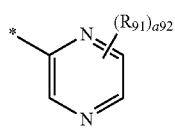

9-5

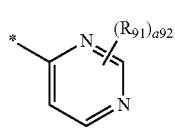

9-6

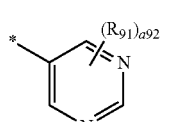

9-7

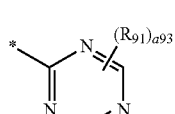

9-8

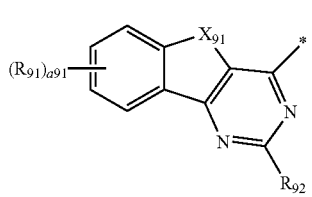

9-51

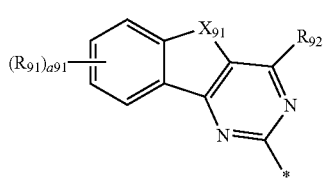

9-52 wherein in Formulae 9-4 to 9-8, 9-51, and 9-52,
$X_{91}$ is selected from O and S;
$R_{91}$ and $R_{92}$ are each independently selected from a hydrogen, a deuterium, F, —Cl, —Br, —I, a cyano group, a nitro group, a $C_1$-$C_{20}$ alkyl group, a $C_1$-$C_{20}$ alkoxy group, a phenyl group, a biphenyl group, a naphthyl group, an anthracenyl group, a pyrenyl group, a phenanthrenyl group, a pyridinyl group, a pyrimidinyl group, a triazinyl group, a quinolinyl group, an isoquinolinyl group, and a quinazolinyl group;

a91 is selected from 1, 2, 3, and 4;
a92 is selected from 1, 2, and 3;
a93 is selected from 1 and 2; and
* indicates a binding site to a neighboring atom.

8. The carbazole compound of claim 1, wherein
at least one selected from $R_{11}$ to $R_{13}$ are each independently selected from Formulae 10-1 to 10-7:

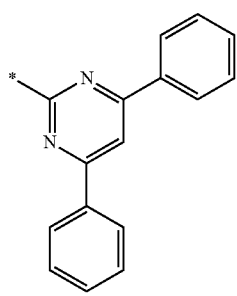

10-1

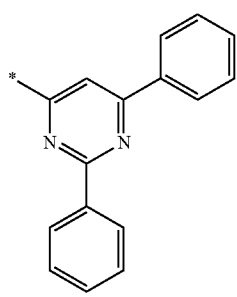

10-2

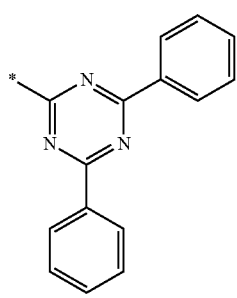

10-3

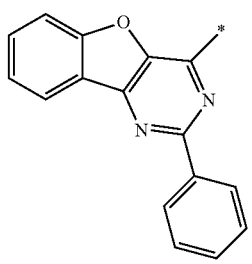

10-4

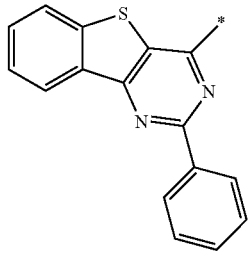

10-5

10-6

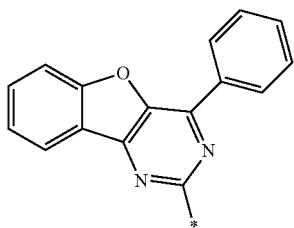

10-7

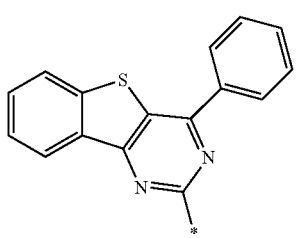

wherein in Formulae 10-1 to 10-7,
* indicates a binding site to a neighboring atom.

9. The carbazole compound of claim 1, wherein the carbazole compound is selected from a group represented by one of Formulae 1-1 to 1-3:

Formula 1-1

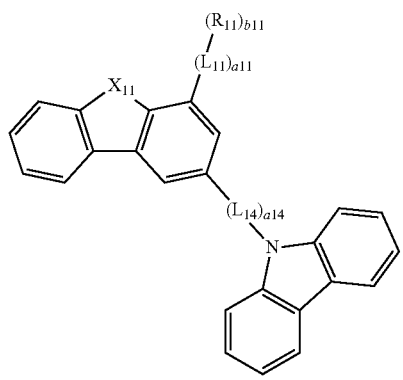

Formula 1-2

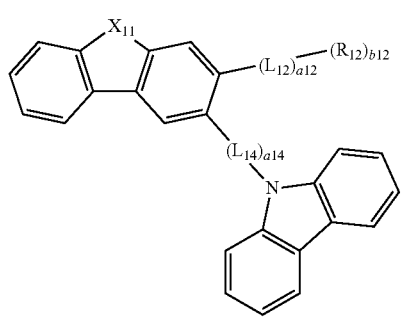

Formula 1-3

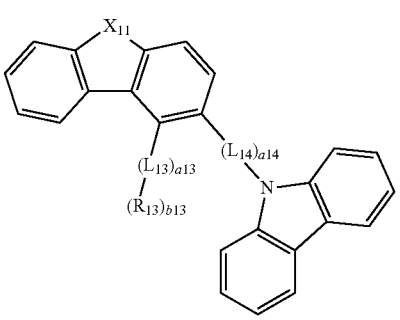

wherein in Formulae 1-1 to 1-3,
$X_{11}$, $L_{11}$ to $L_{14}$, a11 to a14, $R_{11}$ to $R_{13}$, and b11 to b13 are the same as in claim 1;
$R_{11}$ in Formula 1-1, $R_{12}$ in Formula 1-2, and $R_{13}$ in Formula 1-3 are each independently $R_{ET}$.

10. The carbazole compound of claim 1, wherein the carbazole compound is selected from a group represented by one of Formulae 1-1A, 1-2A, and 1-3A:

Formula 1-1A

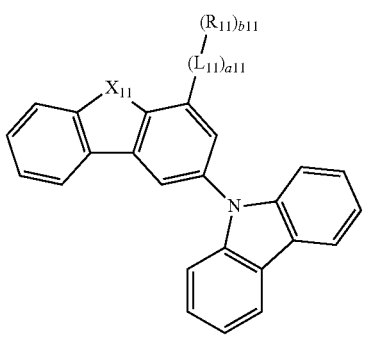

Formula 1-2A

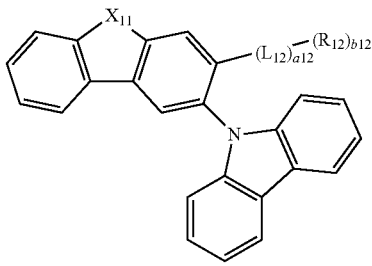

Formula 1-3A

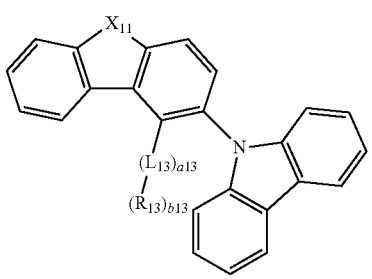

wherein in Formulae 1-1A, 1-2A, and 1-3A,
$X_{11}$, $L_{11}$ to $L_{13}$, a11 to a13, $R_{11}$ to $R_{13}$, and b11 to b13 are the same as in claim 1;
$R_{11}$ in Formula 1-1A, $R_{12}$ in Formula 1-2A, and $R_{13}$ in Formula 1-3A are each independently $R_{ET}$.

11. The carbazole compound of claim 1, represented by Formula 1-1B:

Formula 1-1B
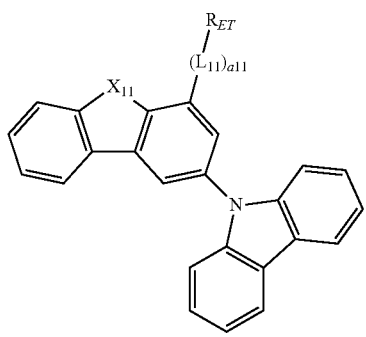
wherein in Formula 1-1B,
$X_{11}$, $L_{11}$, and all are the same as in claim 1,
$R_{ET}$ is selected from Formulae 10-1 to 10-7:
10-1
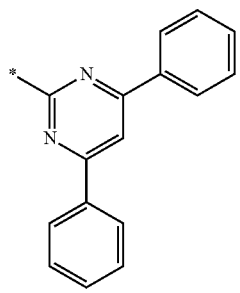
10-2
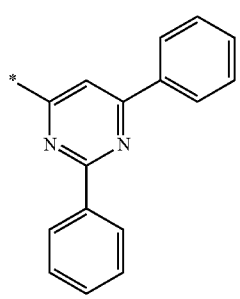
10-3
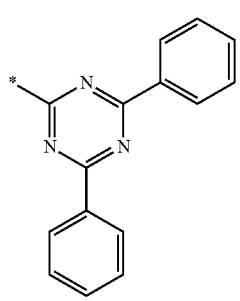
10-4
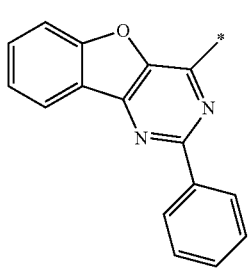
10-5
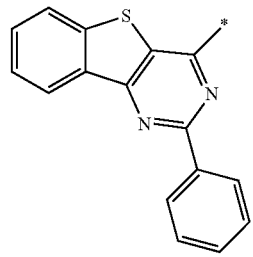
10-6
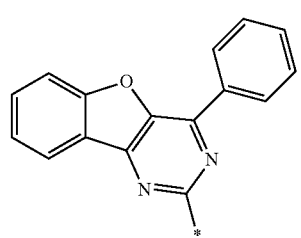
10-7
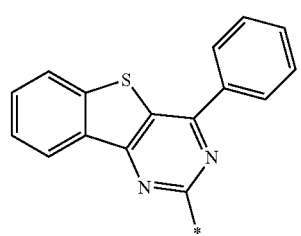
wherein in Formulae 10-1 to 10-7,
* indicates a binding site to a neighboring atom.
12. The carbazole compound of claim 1, wherein the carbazole compound is selected from Compounds 1 to 20:
1
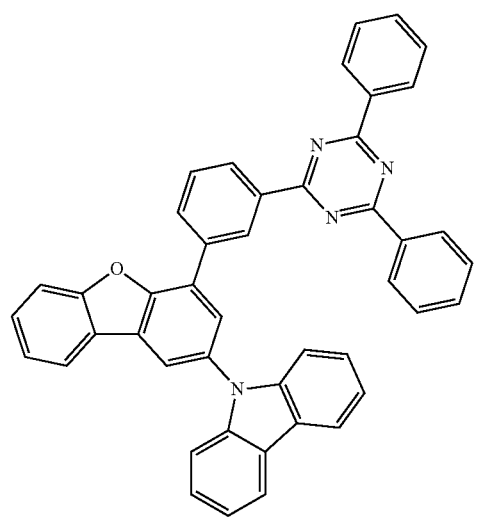

-continued
2
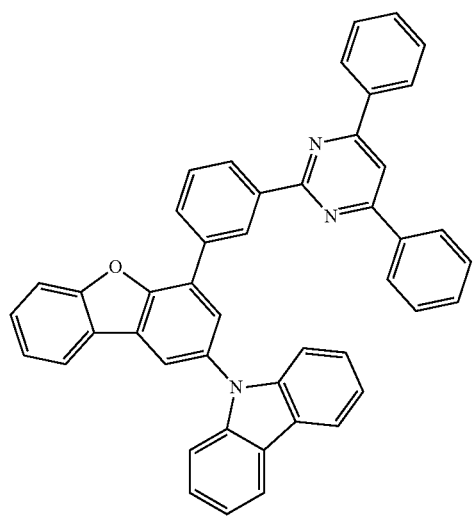
3
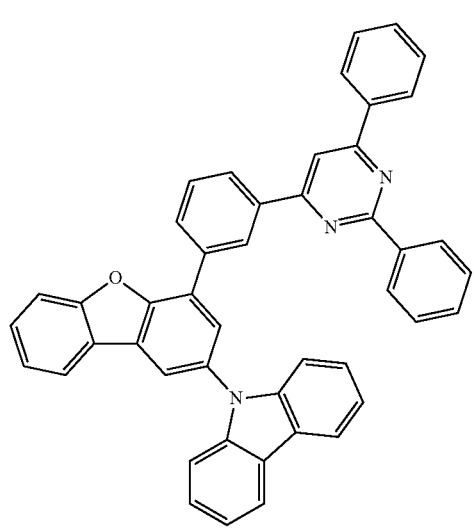
4
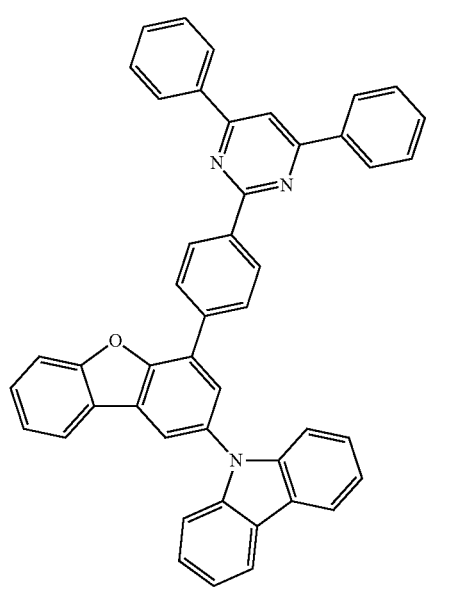
-continued
5
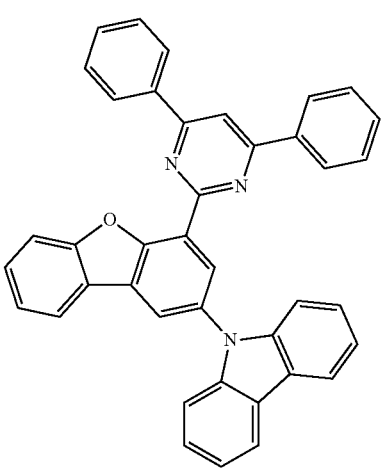
6
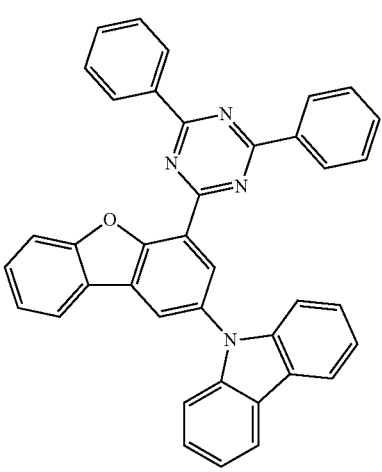
7
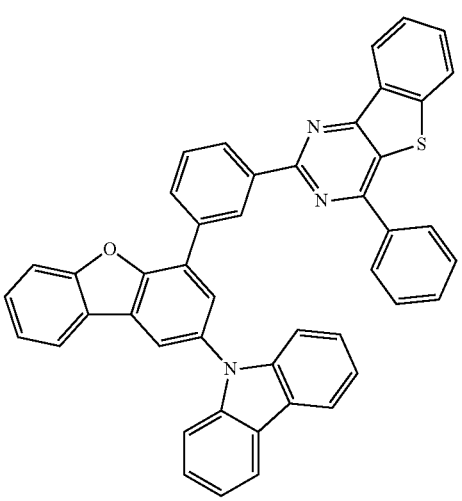

-continued
| 179 | 180 |
|---|---|
| 8 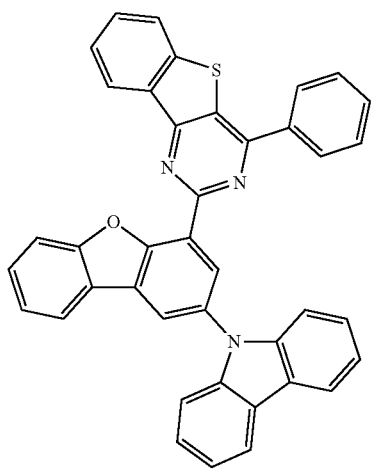 | 11 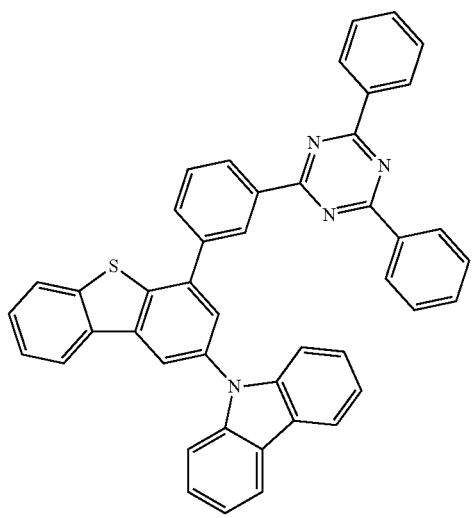 |
| 9 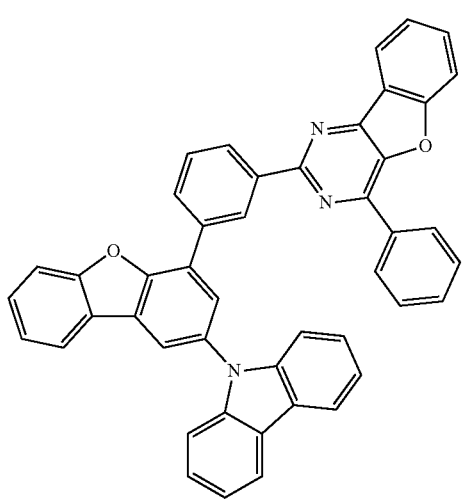 | 12 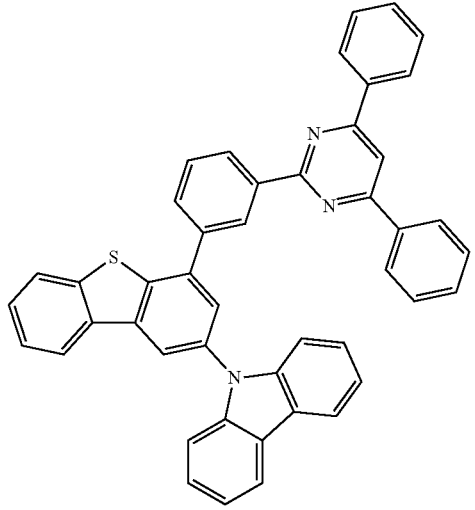 |
| 10 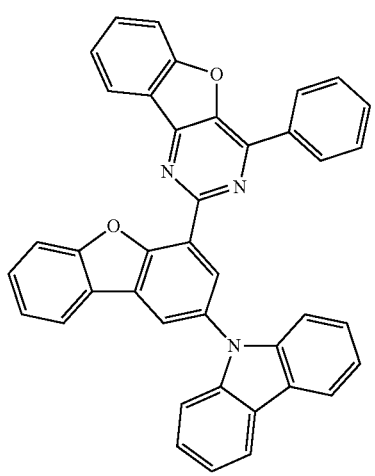 | 13 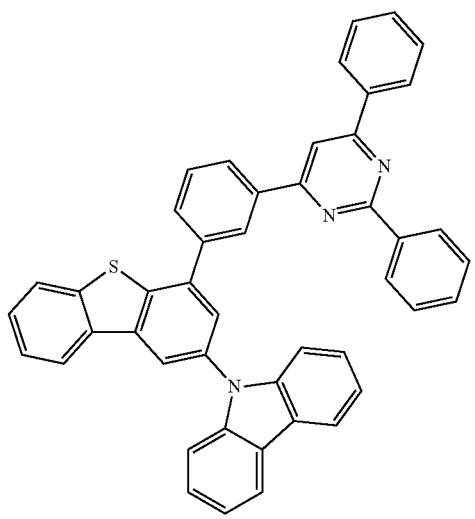 |

14
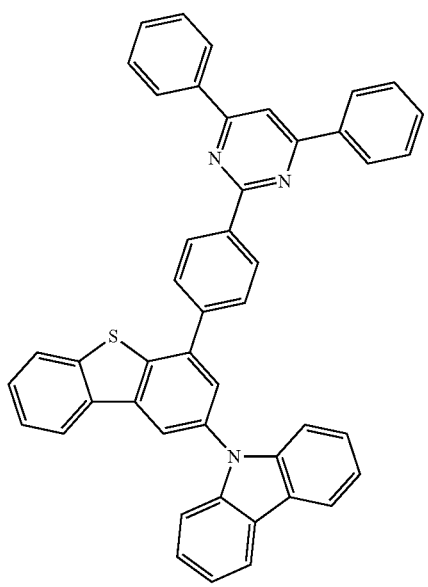
15
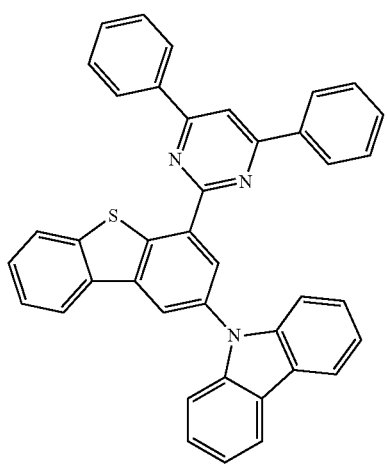
16
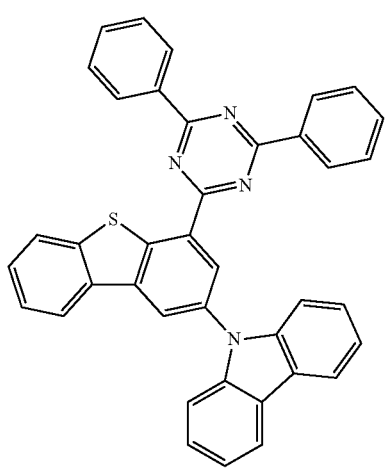
17
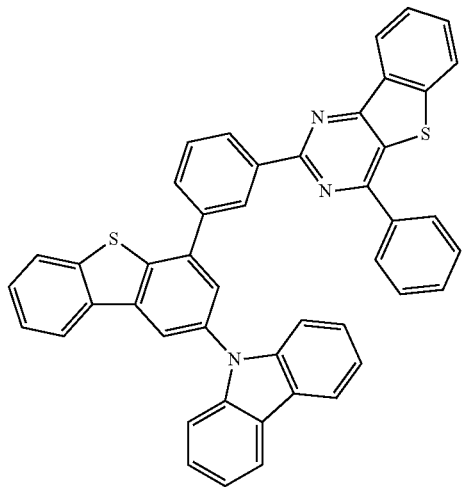
18
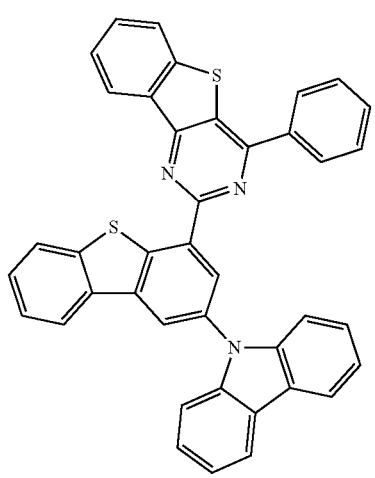
19
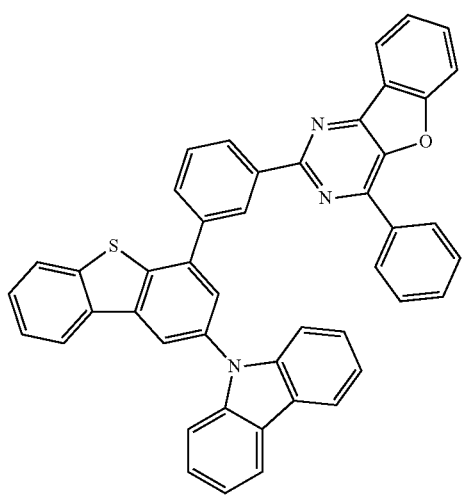

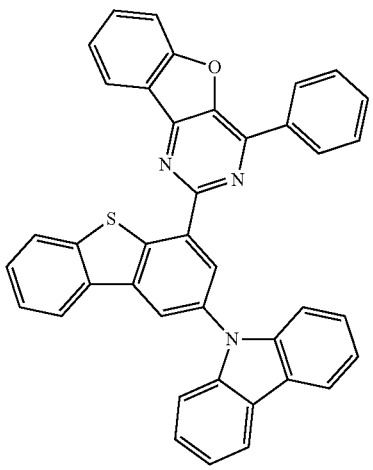

13. An organic light-emitting device comprising:
a first electrode;
a second electrode; and
an organic layer disposed between the first electrode and the second electrode, wherein the organic layer comprises an emission layer and at least one carbazole compound of claim 1.

14. The organic light-emitting device of claim 13, wherein
the first electrode is an anode,
the second electrode is a cathode,
and the organic layer comprises:
i) a hole transport region disposed between the first electrode and the emission layer, wherein the hole transport region comprises at least one selected from a hole injection layer, a hole transport layer, and an electron blocking layer, and
ii) an electron transport region disposed between the emission layer and the second electrode, wherein the electron transport region comprises at least one selected from a hole blocking layer, an electron transport layer, and an electron injection layer.

15. The organic light-emitting device of claim 13, wherein the emission layer comprises the carbazole compound represented by Formula 1.

16. The organic light-emitting device of claim 13, wherein
the emission layer comprise a first host and a second host,
the first host and the second host are different from each other, and
the first host and the second host are each independently selected from any of the carbazole compounds represented by Formula 1.

17. The organic light-emitting device of claim 13, wherein
the emission layer comprises Host 1 and Host 2,
Host 1 and Host 2 are different from each other, and
Host 1 is selected from any of the carbazole compounds represented by Formula 1;
Host 2 is selected from a first compound represented by Formula 4 and a second compound represented by Formula 5:

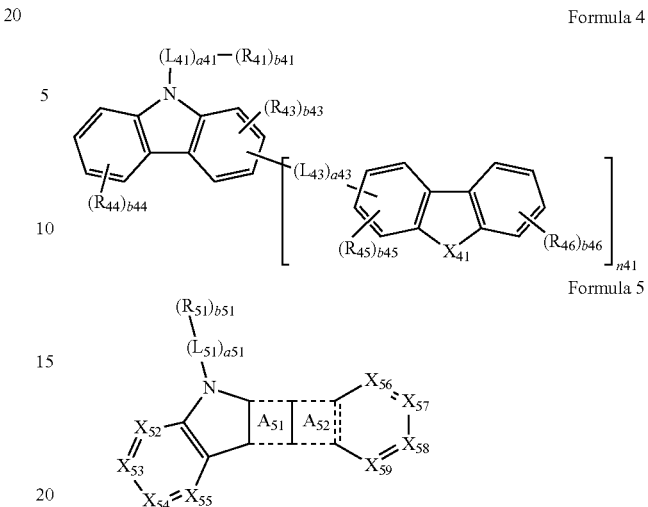

wherein in Formulae 4 to 7,
$X_{41}$ is selected from N-$[(L_{42})_{a42}$-$(R_{42})_{b42}]$, S, O, S(=O), S(=O)$_2$, C(=O), C($R_{47}$)($R_{48}$), Si($R_{47}$)($R_{48}$), P($R_{43}$), P(=O)($R_{47}$), and C=N($R_{47}$);
Ring $A_{51}$ in Formula 5 is represented by Formula 6;
Ring $A_{52}$ in Formula 5 is represented by Formula 7;
$X_{71}$ is selected from N-$[(L_{71})_{a71}$-$(R_{71})_{b71}]$, S, O, S(=O), S(=O)$_2$, C(=O), C($R_{72}$)($R_{73}$), Si($R_{72}$)($R_{73}$), P($R_{71}$), P(=O)($R_{71}$), and C=N($R_{71}$);
$X_{52}$ is C($R_{52}$) or N atom,
$X_{53}$ is C($R_{53}$) or N,
$X_{54}$ is C($R_{54}$) or N,
$X_{55}$ is C($R_{55}$) or N,
$X_{56}$ is C($R_{56}$) or N,
$X_{57}$ is C($R_{57}$) or N,
$X_{58}$ is C($R_{58}$) or N, and
$X_{59}$ is C($R_{59}$) or N;
$L_{41}$ to $L_{43}$, $L_{51}$, and $L_{71}$ are each independently selected from a substituted or unsubstituted $C_3$-$C_{10}$ cycloalkylene group, a substituted or unsubstituted $C_1$-$C_{10}$ heterocycloalkylene group, a substituted or unsubstituted $C_1$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group;
n41, a41 to a43, a51, and a71 are each independently selected from 0, 1, 2, and 3;
$R_{41}$ to $R_{48}$, $R_{51}$ to $R_{59}$, $R_{61}$, and $R_{71}$ to $R_{73}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —N($Q_1$)($Q_2$), —Si($Q_3$)($Q_4$)($Q_5$), and —B($Q_6$)($Q_7$);

b41 to b46, b51, and b71 are each independently an integer selected from 1 to 3;

at least one substituent of the substituted $C_1$-$C_{60}$ alkylene group, substituted $C_2$-$C_{60}$ alkenylene group, substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, substituted divalent non-aromatic condensed polycyclic group, substituted divalent non-aromatic condensed heteropolycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group is selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), and —B($Q_{16}$)($Q_{17}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), and —B($Q_{26}$)($Q_{27}$); and —N($Q_{31}$)($Q_{32}$), —Si($Q_{33}$)($Q_{34}$)($Q_{35}$), and —B($Q_{36}$)($Q_{37}$); wherein $Q_1$ to $Q_7$, $Q_{11}$ to $Q_{17}$, $Q_{21}$ to $Q_{27}$, and $Q_{31}$ to $Q_{37}$ are each independently selected from a hydrogen, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

18. The organic light-emitting device of claim 17, wherein at least one selected from $R_{41}$, $R_{42}$, and $R_{43}$ and at least one selected from $R_{51}$ and $R_{71}$ in Formula 5 are each independently selected from a thiophenyl group, a furanyl group, a carbazolyl group, an acridinyl group, a dibenzofuranyl group, a dibenzothiophenyl group, a benzocarbazolyl group, a dibenzocarbazolyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, and an ovalenyl group; and a thiophenyl group, a furanyl group, a carbazolyl group, an acridinyl group, a dibenzofuranyl group, a dibenzothiophenyl group, a benzocarbazolyl group, a dibenzocarbazolyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, and an ovalenyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a phenyl group-substituted with a $C_1$-$C_{20}$ alkyl group, a phenyl group-substituted with a phenyl group, a naphthyl group, a phenalenyl group, a phenanthrenyl group, an anthracenyl group, a triphenylenyl group, a pyrenyl group, a chrysenyl group, a pyridinyl group, a pyrazinyl group, a pyrimidinyl group, a pyridazinyl group, a naphthyridinyl group, a quinoxalinyl group, a quinazolinyl group, and —Si($Q_{33}$)($Q_{34}$)($Q_{35}$);

wherein $Q_{33}$ to $Q_{35}$ are each independently selected from a $C_1$-$C_{20}$ alkyl group, a alkoxy group, a phenyl group, a naphthyl group, an anthracenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, and a quinoxalinyl group.

\* \* \* \* \*